US012635684B2

(12) United States Patent

Trammell et al.

(10) Patent No.: US 12,635,684 B2

(45) Date of Patent: *May 26, 2026

(54) METHODS AND COMPOSITIONS FOR BIOPRESERVATION

(71) Applicant: THE UNIVERSITY OF NORTH CAROLINA AT CHARLOTTE, Charlotte, NC (US)

(72) Inventors: Susan Trammell, Charlotte, NC (US); Gloria Elliott, Charlotte, NC (US); Madison Young, Charlotte, NC (US)

(73) Assignee: THE UNIVERSITY OF NORTH CAROLINA AT CHARLOTTE, Charlotte, NC (US)

( * ) Notice: Subject to any disclaimer, the term of this patent is extended or adjusted under 35 U.S.C. 154(b) by 400 days.

This patent is subject to a terminal disclaimer.

(21) Appl. No.: 18/492,378

(22) Filed: Oct. 23, 2023

(65) Prior Publication Data

US 2024/0049702 A1 Feb. 15, 2024

Related U.S. Application Data

(60) Division of application No. 16/535,246, filed on Aug. 8, 2019, now Pat. No. 11,849,722, which is a continuation-in-part of application No. 15/420,252, filed on Jan. 31, 2017, now abandoned.

(60) Provisional application No. 62/290,097, filed on Feb. 2, 2016.

(51) Int. Cl.
| | |
|---|---|
| *A01N 1/128* | (2025.01) |
| *A01N 1/168* | (2025.01) |
| *C12N 9/36* | (2006.01) |
| *C12N 9/96* | (2006.01) |

(52) U.S. Cl.
CPC ............. *A01N 1/128* (2025.01); *A01N 1/168* (2025.01); *C12N 9/2462* (2013.01); *C12N 9/96* (2013.01); *C12Y 302/01017* (2013.01)

(58) Field of Classification Search
CPC ........ A01N 1/128; A01N 1/168; A01N 1/162; C12N 9/2462; C12N 9/96; C12Y 302/01017
See application file for complete search history.

(56) References Cited

U.S. PATENT DOCUMENTS

| | | | | |
|---|---|---|---|---|
| 11,849,722 | B2 * | 12/2023 | Trammell | ................ C12N 9/96 |
| 2024/0415112 | A1 * | 12/2024 | Trammell | .............. C12N 5/568 |

* cited by examiner

*Primary Examiner* — Aaron J Kosar

(74) *Attorney, Agent, or Firm* — J. Clinton Wimbish; Maynard Nexsen PC

(57) ABSTRACT

Methods and compositions of storing a biological material are described herein. In some embodiments, these methods provide one or more advantages over current methods. For example, methods described herein can be used to prepare and process biological materials for storage at elevated temperatures. In one aspect, a method of storing a biological material comprises providing a preservation composition and exposing the preservation composition to electromagnetic radiation to form an amorphous solid matrix containing the biological material. In some embodiments, the method further comprises monitoring temperature of the preservation composition during the exposure to the electromagnetic radiation.

20 Claims, 35 Drawing Sheets

White light source

Digital Camera

Polarizer

Analyzer

METHODS AND COMPOSITIONS FOR BIOPRESERVATION

RELATED APPLICATION DATA

The present application is a divisional of U.S. patent application Ser. No. 16/535,246 (pending), filed Aug. 8, 2019, which is a continuation-in-part of U.S. patent application Ser. No. 15/420,252, filed Jan. 31, 2017, which claims priority pursuant to 35 U.S.C. § 119(e) to U.S. Provisional Patent Application Ser. No. 62/290,097, filed Feb. 2, 2016.

FIELD

The present invention relates to methods and compositions for preserving biological compositions, including compositions comprising a biological component.

BACKGROUND

The use of proteins in therapeutics and diagnostics has increased dramatically since the introduction of the first recombinant protein therapeutic—human insulin—more than 30 years ago. Since then, advances in the biotechnology field have led to rapid growth in the discovery of protein-based targets. Protein based therapeutics have been developed to treat diseases ranging from arthritis and psoriasis to cancer. Innovation in protein-based diagnostic formats, such as lab on chip micro arrays, have been used in autoimmune profiling and cancer research. A challenge in the development of protein-based diagnostics and drugs is maintaining the protein in the folded state during processing and storage. The three-dimensional structure of the protein is often responsible for its functional activity.

Point-of-care (POC) testing allows inexpensive and rapid detection of infectious disease, cancer, contaminants and biowarfare agents. In particular, these POC tests are important for use in low-resource settings. Many POC devices utilize immunoassays involving antigen-antibody binding. Nucleic acid-based diagnostics that measure RNA and DNA are becoming more popular because of their high specificity and sensitivity. Microfluidic platforms are a promising technology for nuclei-acid based POC devices. To make practical POC devices, it is desirable to preload and store all of the reagents on chip. There have been attempts to keep reagents on chip in the wet, dry, and gel states for these nucleic acid-based POC tests. For liquid state storage, the reagents are kept as liquids in blister packs. A problem with current POC testing is that the many of the reagents have limited shelf life at room temperature. Freeze drying reagents has also been tried but the assays still require freezing or refrigeration after processing. Gelification has been successful in stabilizing reagents for a short time at room temperature (shipment) but still requires refrigeration for long term storage. Nanoparticles that are included in the assays often require refrigeration to maintain long-term stability and freezing is not possible as it causes aggregation of the particles. This need for cold storage is not practical in low-resource settings where refrigeration/freezing is often not available.

Thus, diagnostics and drugs having biological components, such as proteins, lipids, DNA, RNA, or cells, currently require cold-chain infrastructure to sustain their activity and efficacy during storage and/or transport. Such cold-chain requirements can be expensive, bulky, cumbersome, or simply impractical, especially with regard to point-of-care diagnostics and treatments.

Current methods of protein and nucleic acid preservation for short term storage are refrigeration or freezing temperatures in solution sometimes with a stabilizing agent (see Table 1).

TABLE 1

| Comparison of different storage techniques and general temperature shelf life guidelines | | | | |
|---|---|---|---|---|
| Storage Technique and Temperature | In Solution (4° C.) | Rapid Freezing with Stabilizer (0° C.) | In Solution with Stabilizer (−20° C.) | Deep Freeze with Stabilizer (−80° C.) | Freeze Drying (≤4° C.) |
| General Shelf-life | <1 Month | 1 Month | <1 Year | Years | Years |

Freeze drying, or lyophilization, is the current gold standard for long term protein preservation. Samples are pretreated with a lyoprotectant to reduce ice formation and the solution is slow cooled to −50 to −80° C. The sample then undergoes primary drying to facilitate sublimation of ice followed by secondary drying to remove unfrozen water molecules. Not all proteins are stable during freeze drying and those that are still need to be kept at refrigerated or freezing temperatures. It is a complex, time consuming (>12 hrs), and high cost process. Other groups have investigated methods for the stabilization of these proteins using ionic liquids. However, protein stability depends on the type of ionic liquid used.

Thus, there exists a need to provide a processing and storage methods and compositions for biological-based drugs and diagnostics, such as protein, DNA, RNA, and biological nanoparticles suitable for storage at elevated temperatures that will maintain their structural conformation, while increasing shelf life by decreasing bioactivity.

SUMMARY

Methods and compositions of storing a biological material are described herein. In some embodiments, these methods provide one or more advantages over current methods. For example, methods described herein can be used to prepare and process biological materials for storage at elevated temperatures. In some embodiments, these methods can be used to preserve biological materials, such as proteins, nucleic acids, and cells, of therapeutic and diagnostic materials at ambient temperatures. In some instances, these methods can be used to preserve materials comprising biological components, such as nanoparticles comprising biological ligands or having any biological component, such as a biological payload, lipid membrane structure, protein ligand, lipid ligand, nucleic acid sequence, or other biological structure.

In one aspect, a method of storing a biological material comprises providing a preservation composition and exposing the preservation composition to electromagnetic radiation to form an amorphous solid matrix containing the biological material. In some embodiments, the method further comprises monitoring temperature of the preservation composition during the exposure to the electromagnetic radiation.

The preservation composition, in some cases, comprises the biological material, a disaccharide component, a salt component, and water. In some embodiments, the biological material can comprise biomolecules, nanoparticles, DNA, RNA, viruses, bacteria, cells, engineered cells, tissues and/ or microtissues. The functionality of the biological material, in some cases, is not altered or degraded by storage in the amorphous solid matrix. The disaccharide component, in some cases, can be amorphous throughout the solid matrix. Additionally, in some embodiments, the preservation composition can further comprise one or more dyes and/or nanoparticles interacting with the electromagnetic radiation. Furthermore, water of the preservation composition is removed from the preservation composition via exposure to the electromagnetic radiation.

The amorphous solid matrix comprising the biological material can have a glass transition temperature ($T_g$) greater than −30° C. or greater than 0° C., in some embodiments. The amorphous solid matrix, in some embodiments, can be substantially free of crystals, and can have a water content less than 0.2 $gH_2O/gDryWeight$ (gdw) of the preservation composition.

Methods described herein comprise exposing the preservation composition to electromagnetic radiation. The electromagnetic radiation, in some embodiments, can have a wavelength of 1-3 μm. In some cases, the electromagnetic radiation can be provided as a laser beam. The laser beam can have a Gaussian profile or truncated profile, in some embodiments. Furthermore, the laser beam can have a spot diameter greater than or equal to a diameter of the preservation composition. Alternatively, the laser beam has a spot diameter less than a diameter of the preservation composition. In some embodiments, the laser beam can have a penetration depth less than a thickness of the preservation composition. In some instances, a portion of the laser beam can pass through the preservation composition.

The preservation composition of methods described herein can reside on a substrate. The substrate, in some cases, can be a porous substrate. The substrate, in some instances, can be operable to absorb the portion of the laser beam. In other embodiments, the substrate can be operable to reflect the portion of the laser beam back into the preservation composition. In another aspect, a biological compositions are described herein. Briefly, a biological composition comprises a biological material contained in an amorphous solid matrix comprising a disaccharide component, wherein the amorphous solid matrix has a glass transition temperature ($T_g$) greater than −30° C. or greater than 0° C. In some embodiments, the amorphous solid matrix has a water content less than 0.2 $gH_2O/gdw$ of the biological composition.

The biological material, in some cases, can comprise biomolecules, viruses, bacteria, cells, engineered cells, tissues, microtissues, or nanoparticles. Additionally, the biological material, in some embodiments, maintains tertiary and/or quaternary biochemical structures in the amorphous solid matrix. Such structures, in some cases, can confer biological activity. For example, in some cases, the biological material can retain at least 70% functionality. The functionality can be determined upon rehydration of the biological material.

These and other embodiments are described in greater detail in the following detailed description.

DETAILED DESCRIPTION

Figure 1:
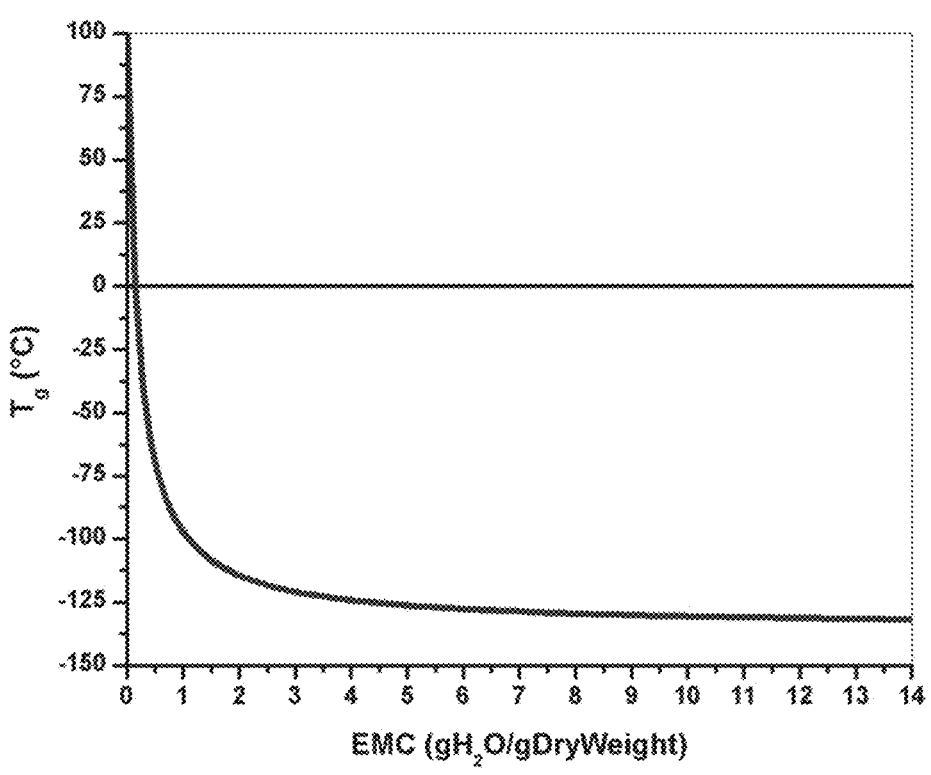
FIG. 1 illustrates a glass transition curve for a binary mixture of trehalose and water according methods described herein.

Embodiments described herein can be understood more readily by reference to the following detailed description and examples. Methods, devices, and features described herein, however, are not limited to the specific embodiments presented in the detailed description and examples. It should be recognized that these embodiments are merely illustrative of the principles of the present disclosure. Numerous modifications and adaptations will be readily apparent to those of skill in the art without departing from the spirit and scope of the disclosure.

In addition, all ranges disclosed herein are to be understood to encompass any and all subranges subsumed therein. For example, a stated range of "1.0 to 10.0" should be considered to include any and all subranges beginning with a minimum value of 1.0 and ending with a maximum value of 10.0 or less, e.g. 1.0 to 5.3, or 4.7 to 10.0, or 3.6 to 7.9.

All ranges disclosed herein are also to be considered to include the end points of the range, unless expressly stated otherwise. For example, a range of "between 5 and 10," "from 5 to 10," or "5-10" should generally be considered to include the endpoints 5 and 10.

Further, when the phrase "up to" is used in connection with an amount or quantity, it is to be understood that the amount is at least a detectable amount or quantity. For example a material present in an amount "up to" a specified amount can be present from a detectable amount and up to and including the specified amount.

I. Methods of Storing a Biological Material

In one aspect, methods of storing a biological material are described herein comprising providing a preservation composition including the biological material, a disaccharide component, a salt component, and water, and exposing the preservation composition to electromagnetic radiation to form an amorphous solid matrix containing the biological material. The amorphous solid matrix, in some embodiments, can have a glass transition temperature ($T_g$) greater than $-30°$ C. or greater than $0°$ C. In some embodiments, the amorphous solid matrix has a water content less than 0.2 $gH_2O/gdw$ of the biological composition.

The preservation composition is suitable to receive the biological material for processing according to one or more steps of methods described herein. Examples of suitable preservation compositions can include one or more compositions described in U.S. patent application Ser. No. 15/600, 445, filed on May 19, 2017 or U.S. Pat. No. 9,930,883 issued on Apr. 3, 2018, each of which is hereby incorporated by reference in its entirety.

Turning now to specific components, the preservation composition comprises a disaccharide component. Any disaccharide component not inconsistent with the objectives of the present disclosure may be used. In some cases, the disaccharide component comprises, consists of, or consists essentially of one or more species formed of two glucose units. For example, in some preferred embodiments, the disaccharide component comprises trehalose or trehalose derivative. A trehalose derivative, in some cases, is a derivative of trehalose in which one or more of the hydroxyl groups of trehalose has been replaced with a protecting group or other group in a manner known in carbohydrate chemistry. In other non-limiting embodiments, a trehalose derivative can exhibit various direct or indirect linkages between the saccharide units. As described further below, the use of trehalose or a trehalose derivative in a preservation composition described herein can provide particularly good performance in solvent and/or biological tissue preservation and storage applications.

The disaccharide component of a preservation composition described herein can be present in the preservation composition in any amount not inconsistent with the objectives of the present disclosure. In some cases, the amount of disaccharide component is selected with respect to an amount of another component of the system, such as a choline-containing component. For example, in some instances, a molar ratio of the disaccharide component to a choline halide (or choline acetate or choline hydrogen phosphate) ranges from 1:2 to 1:6. In some cases, the molar ratio is 1:4.

The salt component of the preservation composition can comprise any salt or combination of salts consistent with the objectives of the present invention. For example, the salt component comprises a choline containing component, in some embodiments. In some cases, the choline containing component is a choline salt. Any choline-containing component or choline salt not inconsistent with the objectives of the present disclosure may be used. In some preferred embodiments, the choline-containing component comprises, consists of, or consists essentially of a choline halide such as choline chloride. In other instances, choline acetate is used. In still other cases, the choline-containing component comprises choline phosphate. Other choline salts may also be used.

The choline-containing species of a preservation composition described herein can be present in the preservation composition in any amount not inconsistent with the objectives of the present disclosure. In some embodiments, for example, the amount of choline-containing species is selected with respect to an amount of another component of the system, such as the disaccharide component. In some cases, a molar ratio of the disaccharide component to the choline-containing species ranges from 1:2 to 1:6. In some cases, the molar ratio is 1:4.

The preservation composition described herein can also include water, particularly in an amount of 5 weight percent to less than 25 weight percent, based on the total weight of the preservation composition, or based on the total weight of the disaccharide component, choline-containing component, and water component. In some instances, the water is present in the preservation composition in an amount of 10 weight percent to less than 25 weight percent, 12 weight percent to less than 25 weight percent, 15 weight percent to less than 25 weight percent, or 20 weight percent to less than 25 weight percent. In some cases, the water is present in the preservation composition in an amount of 5-23, 5-20, 10-23, 10-20, 10-15, 12-23, 12-20, 12-15, 15-23, or 15-20 weight percent, based on the total weight of the preservation composition, or based on the sum of the weights of the disaccharide component, choline-containing component, and water component.

The preservation composition also comprises the biological material. Any biological material not inconsistent with the objectives of the present disclosure. In some cases, the biological composition comprises one or more of biological molecules, such as proteins, lipids, DNA, RNA, viruses (including bacteriophages), bacteria, cells, engineered cells, tissues, engineered tissues, organs, micro-tissues, micro-physiological systems, and nanoparticles, including nanoparticles comprising a biological component. For example, in some cases, the biological material can include biological nanoparticles formed from micelles or comprising a lipid bilayer. In some embodiments, the biological material can include non-biological nanoparticles conjugated to, covalently linked to, or encasing a biological material. For example, in some instances, the biological material can include non-biological nanoparticles comprising a biological payload, a protein ligand, a lipid ligand, a nucleic acid sequence, or other biological or cellular structure. In some embodiments, the biological material can include conjugated nanoparticles, wherein the conjugated nanoparticles comprise a covalently linked biological ligand. In some embodiments, the biological material is a large tissue sample, such as a complete organ. Non-limiting examples of biological material can include immunotherapy agents, biological pharmaceuticals, biomimetic pharmaceuticals, recombinant proteins, vaccines, blood, eggs, sperm, small tissues, cornea, lipid membranes, molecular signal transducers, and others.

In some embodiments, the preservation composition can further comprise one or more dyes and/or nanoparticles interacting with the laser radiation. It should be understood that such dyes and/or nanoparticles of the preservation composition are distinct from and non-interchangeable with nanoparticles of the biological composition. That is, in some embodiments of methods described herein, the preservation composition can comprise one or more dyes and/or nanoparticles and the biological composition can comprise nanoparticles, wherein the one or more dyes and/or nanoparticles of the preservation composition are not the same as the nanoparticles of the biological composition. A dye and/or nanoparticles present in the preservation composition can facilitate enhanced or faster drying by coupling the dye and/or nanoparticles with a laser of different wavelength. For example, a laser wavelength can correspond to a wavelength of the dye and/or nanoparticle that exhibits absorption of the laser light. In some embodiments, inorganic or organic nano-spheres or nanoparticles as either a solid particle or a core-shell configuration can be used. In some cases, such nanoparticles can enhance efficacy of the preservation material, for example, by photosensitizing the composition when exposed to a specific wavelength of electromagnetic radiation. In some cases, the nanoparticles can comprise a polymer or a metal. Some non-limiting examples of nanoparticles suitable for such a preservation composition can include silver nanoparticles or gold nanoparticles that can optionally be coated or functionalized. Other nanoparticles not inconsistent with the objectives of the present disclosure are also contemplated.

Methods described herein comprise exposing the preservation composition to electromagnetic radiation to form an amorphous solid matrix containing the biological material. Exposing the preservation composition to electromagnetic radiation can include irradiating the preservation composition with infrared, near-infrared, visible light, or any combination thereof. For example, in some cases, the electromagnetic radiation has a wavelength between about 0.4 $\mu$m and 3.5 $\mu$m. In some embodiments, the electromagnetic radiation has a wavelength between about 0.4 $\mu$m and 1 $\mu$m, between about 1 $\mu$m and 3 $\mu$m, between about 1 $\mu$m and 2.5 $\mu$m, between about 1 $\mu$m and 2 $\mu$m, between about 1.5 $\mu$m and 2 $\mu$m, about 1064 nm, about 1550 nm or about 1850 nm.

The electromagnetic radiation, in some cases, is provided as a laser beam. In some embodiments the laser beam has a Gaussian profile. For example, a distribution of light and/or energy across a diameter of a beam can exhibit a Gaussian profile wherein the outer perimeter of the beam exhibits a lower intensity compared to the center point of the laser beam. Thus, a Gaussian laser beam can deliver a different amount of energy across an area or across a volume of the preservation composition. For example, in some instances, a center of the preservation composition can receive more energy than an edge of the preservation composition. In other embodiments, the laser beam can be truncated and/or exhibit a uniform energy density over the diameter of the beam.

Furthermore, in some embodiments, the laser beam can have a spot diameter that is greater to or equal to a diameter of the preservation composition. For example, the preservation composition can be equal in area or smaller in area than a width of the laser beam such that the preservation composition is exposed to either the entire beam or a certain fraction of the laser beam, such as a fraction above a threshold intensity. In some embodiments, the laser beam has a spot diameter that is less than a diameter of the preservation composition.

Additionally, in some embodiments, the laser beam can have varying penetration depth. In some cases, the laser beam can have a penetration depth that is less than the thickness of the preservation composition. In some cases, the laser beam can have a penetration depth that is greater than the thickness of the preservation composition. For example, in some such instances, a laser beam having a penetration depth between about 0.1 mm and 500 mm can be used in methods described herein. In some instances, a laser having a penetration depth between about 0.1 mm and 100 mm, between about 0.5 mm and 100 mm, about 0.8 mm, or about 80 mm can be used.

Any laser not inconsistent with the objectives of the present disclosure can be used. In some embodiments, lasers are a preferred source of electromagnetic radiation of methods described herein as they are monochromatic and collimated, and can, thus, deliver precise amounts of energy to a target. The present disclosure can implement the principle of selective absorption for dehydration of a biological material in preparation for anhydrous storage. The laser, for example, can be tuned for maximum absorption by water. Furthermore, precise energy deposition into the preservation composition is preferred to control the drying rate and the water content (or end moisture content) of the preservation composition.

In some embodiments, particularly wherein a laser beam has a penetration depth greater than the thickness of the preservation composition, the laser beam can pass through the preservation composition. In such instances, a laser beam passing through the preservation composition can either be absorbed or reflected by a material or a substrate immediately adjacent or beneath the preservation composition.

In some embodiments, the laser beam, as described herein, can be coupled to an optical system. The optical system, in some cases, can allow the laser beam to pass through the sample two times, three times, or more than three times. In some embodiments, the optical system can provide enhanced control of the laser beam diameter. In some embodiments, the optical system can provide more efficient energy transfer from the laser to water in the preservation composition and/or biological composition. In still further embodiments, the optical system can provide more uniform heating of the preservation composition. Such an optical system can include, for example, one or more lenses and/or mirrors positioned between or around the laser beam source and the preservation composition. Lenses of the optical system can be positioned between the laser source and the preservation composition such that the laser beam passes through the lens before reaching the preservation composition. One or more mirrors of the optical system can be positioned behind the preservation composition, or around the preservation composition, such that the laser beam is redirected by the one or more mirrors and through the preservation composition multiple times. Not intending to be bound by theory, it is believed that multiple passes of the laser through the preservation composition can increase energy deposition and provide more uniform heating of the preservation composition.

In some embodiments, the preservation composition resides on a substrate. Varying materials of substrates can be used, the properties of which can influence one or more steps of methods described herein. For example, in some embodiments, a substrate can be operable to absorb a portion of the laser beam. Some non-limiting examples of such absorptive substrates are provided in the Examples section below. In some embodiments, the preservation composition resides on a substrate operable to reflect a portion of the laser beam back into the preservation composition. Some non-limiting examples of such reflective substrates are provided in the Examples section below. Various properties, as described herein, can be more or less desirable based on the desired amount of laser beam absorption or reflectivity.

In some cases, a substrate can be a porous material. A porous substrate can, in some cases, increase a drying rate of the preservation composition. In some instances, a substrate can have a high or low surface adhesion. A substrate having a low surface adhesion can be hydrophobic in nature. For example, a hydrophobic substrate can be formed from a hydrophobic material or comprise a hydrophobic coating such that the preservation composition exhibits high surface tension and minimal spreading across the hydrophobic substrate. In some embodiments, a substrate can have a high or low transmissivity of the electromagnetic radiation. A substrate having high transmissivity, in some cases, can require increased exposure time, while minimizing a maximum processing temperature during the laser exposure. In contrast, a substrate having low transmissivity or an absorptive substrate, in some instances, can reduce exposure time, possibly at the expense of an increased maximum processing temperature.

Additionally, a substrate can have a varying surface shape, such as a curved or planar shape. In some instances, the surface shape of the substrate can modify the 3-dimensional profile of the preservation composition or the spreading of the preservation composition across the substrate. For example, a convex shaped substrate, in some instances, can increase the spreading of the preservation composition across the substrate while simultaneously increasing the thickness of the preservation composition near its perimeter and decreasing the thickness of the preservation composition near its center. A planar substrate can, in some instances, reduce spreading of the preservation composition across the substrate while maintaining a thicker center and thinner perimeter. Furthermore, in some embodiments, a flexible substrate is desirable, particularly, for purposes of storage, or for manipulating the substrate surface shape during the exposure step.

In some embodiments, the preservation composition of methods described herein comprises a thickness or a height. In some instances, the thickness of the preservation composition can be constant across a diameter of the preservation composition. In some instances, the thickness of the preservation composition varies across a diameter of the preservation composition. In some embodiments, the preservation composition exhibits a thickness of about 1-10 mm. In some embodiments, the preservation composition exhibits a thickness of no more than about 10 mm, no more than about 8 mm, no more than about 6 mm, no more than about 5 mm, no more than about 4 mm, no more than about 3 mm, or no more than about 2 mm.

The thickness or height of the preservation composition, in some embodiments, can be influenced by the surface shape and/or the material of the substrate on which the preservation composition resides or contacts. For example, one or more properties of the substrate, as described above, can influence the contact angle and, in some cases, consequently the evaporation mode, as described further herein below.

Accordingly, the surface shape of the substrate, by modifying the 3-dimensional shape of the preservation composition, can influence a temperature distribution across an area of the preservation sample. For example, a preservation composition disposed on or residing on a planar substrate can form a semispherical cap shape having a thick center and thin edges. A Gaussian beam, as described above, can heat the thickest portion of the preservation composition to a high temperature while maintaining a lower temperature near the thin edges, resulting in a constant contact mode of evaporation.

In some embodiments, the method further comprises monitoring temperature of the preservation composition during the exposure to the electromagnetic radiation. For example, in some cases, exposure of the preservation composition to electromagnetic radiation can result in heating or a change in temperature of the preservation composition during the time period of exposure. Since many biological materials are sensitive to extreme temperatures, or in some cases, certain temperature thresholds, a step of monitoring temperature of the preservation composition can comprise preventing the preservation composition from reaching a threshold temperature. A threshold temperature can vary based on the type of biological material present in the preservation composition. For example, in some instances, a cell can have a higher threshold temperature than a protein. In some instances, a first protein can have a higher threshold temperature than a second protein. The threshold temperature can be determined according to the biochemical structures and make-up of the biological material. For example, in some instances, a threshold temperature of a biological material is about the same as a denaturing temperature. In some embodiments, the threshold temperature can be between about −100° C. and 200° C., between about 0° C. and 100° C., between about 0° C. and 80° C., between about 0° C. and 60° C., between about 0° C. and 50° C., or between about 0° C. and 40° C. Any threshold temperature, including fractions, falling within such ranges can be used.

In some embodiments, water of the preservation composition is removed from the preservation composition via exposure to the electromagnetic radiation. During exposure of the preservation composition to electromagnetic radiation the water component can evaporate from the preservation composition consequently drying the preservation composition. Thus, in some embodiments, the method comprises dehydrating, drying, or evaporating water from the preservation composition. The rate of dehydration in some embodiments, is determined as the amount of water lost per gram of dry weight (gdw) per minute exposure to electromagnetic radiation. For example, in some embodiments, the rate of dehydration can be between about 0.01 $gH_2O/gdw/min$ and 1 $gH_2O/gdw/min$, between about 0.05 $gH_2O/gdw/min$ and 1 $gH_2O/gdw/min$, between about 0.1 $gH_2O/gdw/min$ and 1 $gH_2O/gdw/min$, or between about 0.01 $gH_2O/gdw/min$ and 0.6 $gH_2O/gdw/min$.

In some embodiments of methods described herein, an amorphous solid matrix containing the biological material is formed upon exposure of the preservation composition to electromagnetic radiation. The disaccharide component, in some cases, can be amorphous throughout the solid matrix. The amorphous solid matrix, in some embodiments, is an amorphous trehalose solid. In some embodiments, the amorphous solid matrix is substantially free of crystals. Such crystals that are absent from the amorphous solid matrix can be any crystal or crystalline form of any component of the amorphous solid matrix or any combination of components of the amorphous solid matrix. For example, in some cases, the amorphous solid matrix comprises less than 5% crystallization, less than 3% crystallization, less than 2% crystallization, less than 1% crystallization, or less than 0.5% crystallization. Crystallization can be determined according to the total surface area or volume of the amorphous solid matrix such that crystalized pixels or voxels are quantified as a percent of the whole.

In some embodiments, the amorphous solid matrix has a water content or end moisture content that is less than 0.5 $gH_2O/gdw$, less than 0.4 $gH_2O/gdw$, less than 0.3 $gH_2O/gdw$, less than 0.2 $gH_2O/gdw$, less than 0.1 $gH_2O/gdw$, or less than 0.05 $gH_2O/gdw$ of the preservation composition.

In some embodiments, the amorphous solid matrix is a glass-forming protectant achieved by rapid dehydration of the preservation composition. Thus, whereas other materials or compositions may form crystals upon dehydration, the preservation composition of methods described herein achieves a glassy amorphous state. In some embodiments, the amorphous solid matrix containing the biological material has a glass transition temperature $(T_g)$ greater than −50° C., greater than −40° C. greater than −30° C., greater than −20° C., greater than −10° C., greater than 0° C., or greater than 10° C.

Methods described herein can effectively dehydrate a preservation composition to a state suitable for storage at elevated temperatures. Such a state, is primarily due to the absence or near absence of water content (end moisture content) in the amorphous solid matrix. It thus goes, that stability of the amorphous solid matrix is dependent on a sustained absence or near absence of water content in the amorphous solid matrix. Accordingly, in some embodiments, the method further comprises storing the amorphous solid matrix containing the biological material under an atmosphere having less than 50% relative humidity (% RH), less than 40% RH, less than 30% RH, less than 25% RH, less than 20% RH, less than 15% RH, or less than 10% RH.

Methods described herein can effectively preserve biological materials in an anhydrous state at elevated temperatures. As shown in the Examples provided below, methods described herein can further preserve the functionality and structure of the biological material. For example, in some embodiments, the functionality of the biological material is not altered or lost by storage in the amorphous solid matrix. In some cases, the biological material can retain or maintain about 60% to 100% functionality. In some instances, the biological material can retain or maintain at least 50%, at least 60%, at least 70% at least 80% at least 90% or at least 95% functionality.

Biological function is often dependent on structural integrity of biochemical structures, such as protein structures. Thus, in some embodiments, the structural integrity of the biological material is not altered or lost by storage in the amorphous solid matrix. Examples of such structural features can include, but are not limited to, micro and macro structures, such as secondary, tertiary, or quaternary protein structure, lipid signaling structures, lipid membrane structures, organelle structures, macrocellular structures, tissue structures, or other similar biologically relevant structures. In some embodiments, the biological material is not denatured in the amorphous solid matrix. In some cases, the biological material can retain or maintain about 60% to 100% of its micro and macro structures, as described herein. In some instances, the biological material can retain or maintain at least 50%, at least 60%, at least 70% at least 80% at least 90% or at least 95% of its micro and macro structures, as described herein.

II. Biological Compositions

In another aspect, biological compositions are described herein. In some embodiments, a biological composition comprises a biological material contained in an amorphous solid matrix comprising a disaccharide component, wherein the amorphous solid matrix has a glass transition temperature $(T_g)$ greater than −30° C. Features and characteristics of the biological composition described herein can include any one or more components, features or characteristics of the preservation composition or the amorphous solid matrix formed from the preservation composition described of the methods of storing a biological material in Section I above of the present disclosure. For example, the amorphous solid matrix of a biological composition has a glass transition temperature that is substantially the same as that described of the amorphous solid matrix in Section I. Other components, features, and characteristics of the biological material and the amorphous solid matrix of biological compositions described herein are also described in Section I.

Now turning to specific features of the amorphous solid matrix, the amorphous solid, in some embodiments, comprises a disaccharide component. Any disaccharide component described above in Section I can be used.

In some embodiments, the amorphous solid matrix can have a glass transition temperature $(T_g)$ greater than −50° C., greater than −40° C. greater than −30° C., greater than −20° C., greater than −10° C., greater than 0° C., or greater than 10° C. In some embodiments, the amorphous solid matrix is substantially free of crystals. Such crystals that are absent from the amorphous solid matrix can be any crystal or crystalline form of any component of the amorphous solid matrix or any combination of components of the amorphous solid matrix. For example, in some cases, the amorphous solid matrix comprises less than 5% crystallization, less than 3% crystallization, less than 2% crystallization, less than 1% crystallization, or less than 0.5% crystallization according to the total volume of the amorphous solid matrix.

The biological material of a biological composition described herein can comprise any biological material as described in Section I. For example, the biological material can include one or more of biological molecules, such as proteins, lipids, DNA, RNA, viruses (including bacteriophages), bacteria, cells, engineered cells, tissues, engineered tissues, organs, micro-tissues, microphysiological systems, and nanoparticles, including nanoparticles comprising a biological component. For example, in some cases, the biological material can include biological nanoparticles formed from micelles or comprising a lipid bilayer. In some embodiments, the biological material can include non-biological nanoparticles conjugated to, covalently linked to, or encasing a biological material. For example, in some instances, the biological material can include non-biological nanoparticles comprising a biological payload, a protein ligand, a lipid ligand, a nucleic acid sequence, or other biological or cellular structure. In some embodiments, the biological material can include conjugated nanoparticles, wherein the conjugated nanoparticles comprise a covalently linked biological ligand. In some embodiments, the biological material is a large tissue sample, such as a complete organ. Non-limiting examples of biological material can include immunotherapy agents, biological pharmaceuticals, biomimetic pharmaceuticals, recombinant proteins, vaccines, blood, eggs, sperm, small tissues, cornea, lipid membranes, molecular signal transducers, and others.

In some embodiments the biological composition has a water content or end moisture content that is less than 0.5 $gH_2O/gdw$, less than 0.4 $gH_2O/gdw$, less than 0.3 $gH_2O/gdw$, less than 0.2 $gH_2O/gdw$, less than 0.1 $gH_2O/gdw$, or less than 0.05 $gH_2O/gdw$ of the preservation composition. As described above, the biological composition can further be substantially free of crystals. Such crystals that are absent from the biological composition can be any crystal or crystalline form of any component of the biological composition or any combination of components of the biological composition. For example, the biological composition can comprise less than 20% crystallization, less than 15% crystallization, less than 10% crystallization, less than 5% crystallization, less than 3% crystallization, less than 2% crystallization, less than 1% crystallization, or less than 0.5% crystallization. Crystallization can be determined according to the total surface area or volume of the amorphous solid matrix such that crystalized pixels or voxels are quantified as a percent of the whole.

Additionally, as described above of the biological material, a biological composition comprises biological material that maintains its functionality. For example, in some embodiments, the functionality of the biological material is not altered or lost by storage in the amorphous solid matrix. In some cases, the biological material can retain or maintain about 60% to 100% functionality. In some instances, the biological material can retain or maintain at least 50%, at least 60%, at least 70% at least 80% at least 90% or at least 95% functionality.

Biological function is often dependent on structural integrity of biochemical structures, such as protein structures. Thus, in some embodiments, the structural integrity of the biological material is not altered or lost by storage in the amorphous solid matrix. Examples of such structural features can include, but are not limited to, micro and macro structures, such as secondary, tertiary, or quaternary protein structure, lipid signaling structures, lipid membrane structures, organelle structures, macrocellular structures, tissue structures, or other similar biologically relevant structures. In some embodiments, the biological material is not denatured in the amorphous solid matrix. In some cases, the biological material can retain or maintain about 60% to 100% of its micro and macro structures, as described above. In some instances, the biological material can retain or maintain at least 50%, at least 60%, at least 70% at least 80% at least 90% or at least 95% of its micro and macro structures, as described above.

Many modifications and other embodiments of the subject matter will come to mind to one skilled in the art to which the subject matter pertains having the benefits of the teachings presented in the foregoing descriptions and the associated drawings. For example, although specific configurations of the preservation composition are described herein, other preservation compositions configured to form an amorphous solid matrix according to methods described herein may benefit from embodiments of the present subject matter. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

Various implementations of methods and compositions have been described, and exemplary embodiments are described below in fulfillment of various objectives of the present disclosure. It should be recognized that these implementations are merely illustrative of the principles of the present disclosure. Numerous modifications and adaptations thereof will be readily apparent to those skilled in the art without departing from the spirit and scope of the present disclosure. For example, individual steps of methods described herein can be carried out in any manner not inconsistent with the objectives of the present disclosure, and various configurations or adaptations of compositions described herein may be used.

Example 1

The present example illustrates principles employed according to methods described herein.

Amorphous Solids & Anhydrous Preservation

Anhydrous, or dry state, preservation in a trehalose amorphous solid matrix may be an alternative to freeze drying for the preservation of biological samples. An amorphous solid is a non-crystalline solid such as a glass, plastic or gel. Atoms in a crystalline solid exhibit a property called long-range order; atomic positions repeat in space in a regular lattice. In an amorphous solid, the atoms and molecules are not organized in a lattice pattern (there is no long-range order). An amorphous solid restricts molecular motion to a small volume over a finite time period, which can prevent the degradation of biologics, such as proteins, embedded in the matrix. The regular lattice of a crystalline solid can damage some types of embedded biologics, limiting the usefulness of these solids as preservation matrices.

The main mechanisms for forming an amorphous material are direct solid conversion of the crystal to a glass or transformation of a solution to glass. Methods described herein focus on the transition from liquid to glass. Glass formation requires bypassing crystallization as the solid forms, usually through rapid cooling. Nearly all materials can, if cooled rapidly, form an amorphous solid, but the definition of "rapidly" varies widely among materials. The key to the formation of an amorphous solid is to cool the sample quickly enough to form a glass, instead of slowly to form a crystal. An alternative to rapid cooling is to form the amorphous solid by removing water quickly from a solution to form an amorphous solid preservation matrix. As water is removed from the sample, the remaining sugars and salts become concentrated, and, as long as the solutes do not crystallize, the viscosity increases with progressive water loss until an amorphous solid is achieved. Disaccharide trehalose can form a low mobility glass (amorphous solid) at room temperature and can also act as a bioprotectant, making trehalose an attractive option as a preservation matrix for embedded biologics. Trehalose is thought to protect biologics during dehydration by compensating for the loss of hydrogen bonding with water on the surface of folded proteins without changing their conformation.

Because a substantial reduction of molecular mobility is necessary to ensure an extended shelf life, samples need to be stored below the glass transition temperature, $T_g$, of the trehalose matrix to prevent degradation. Below $T_g$ the trehalose maintains its amorphous state. The Gordon-Taylor equation can be used to predict the glass transition temperature ($T_g$) of trehalose-water mixtures.

$$T_g = \frac{x_1 T_{g,1} + k_{GT}(1 - x_1)T_{g,2}}{x_1 + k_{GT}(1 - x_1)}$$ [Equation 1]

The glass transition temperatures of pure trehalose and pure water are given by $T_{(g,1)}$ and $T_{(g,2)}$ respectively, $\times 1$ is the weight fraction of trehalose, and k is an empirically determined fitting parameter. The glass transition temperature for an amorphous trehalose solid formed by dehydration depends on the amount of water remaining in the sample after processing (see FIG. 1). FIG. 1 shows a glass transition curve for a binary mixture of trehalose and water.

The more water that remains in the sample, the lower the glass transition temperature. Lower moisture contents are necessary for storage at higher temperatures. Achieving these low end moisture contents, while maintaining protein functionality, is the key to success for anhydrous preservation methods.

Light-Assisted Drying (LAD)

We have developed a new processing technique for creating amorphous trehalose solids for the stabilization of proteins in the dry state that uses illumination with near-infrared light to assist in the dehydration of the sample. Laser radiation is routinely used in a variety of therapeutic procedures in medicine ranging from cataract surgery to tattoo removal.30,31 Lasers are the light sources of choice for these procedures as they are monochromatic and collimated, thus can deliver precise amounts of energy to a target. Most therapeutic laser procedures in medicine are based on the idea of selective photothermolysis, which is the precise targeting of chromophores (e.g. water, melanin, hemoglobin and even tattoo ink) in tissue using a specific wavelength of light with the intention of selective absorption of light into a target tissue without absorption in surrounding tissue.32 The energy directed into the target area produces sufficient heat to damage the target while allowing the surrounding area to remain relatively untouched. For example, blood absorbs light strongly at 530 nm, while absorption due to water (the dominant component of soft tissue) is significantly lower at these wavelengths.33 Laser treatments of cutaneous hyper vascular malformations such as port-wine stain birthmarks and facial veins exploit the selective absorption of blood. A pulsed laser with wavelength near the 530 nm blood absorption peak heats and coagulates blood vessels, while leaving surrounding water-rich tissue undamaged.34,35 We are implementing the principle of selective absorption for dehydration of samples in preparation for anhydrous storage.

Static air-drying of sugar solutions is dominated by evaporative cooling which causes the drying rate to slow substantially. This allows for crystallization of the sugars. We are selectively heating the water in samples of 40 μl droplets to overcome cooling due to evaporation and speed dehydration of the samples. NIR light can efficiently transfer energy to water, meaning that when a water-trehalose mixture is illuminated with these wavelengths of light, the sample will absorb energy and heat. Light traveling through a medium can either be scattered or absorbed. In the near-IR spectrum, light absorption is the dominant effect and the optical penetration depth, $\delta P$, of the light into a sample can be determined using the absorption coefficient, $\mu a$. Optical penetration depth is the depth at which light intensity decreases to 1/e of the initial intensity and, when $\mu a >> \mu s$, is given by $$\delta_p \approx \frac{1}{\mu_a}$$ [Equation 2]

Figure 2:
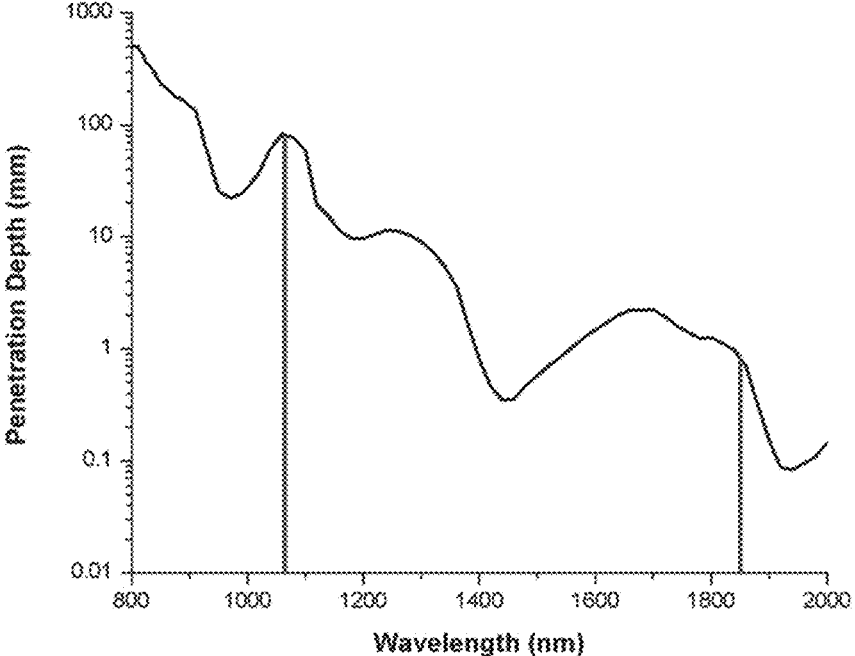
FIG. 2 illustrates an optical penetration depth in water as a function of wavelength according methods described herein.
Figure 3:
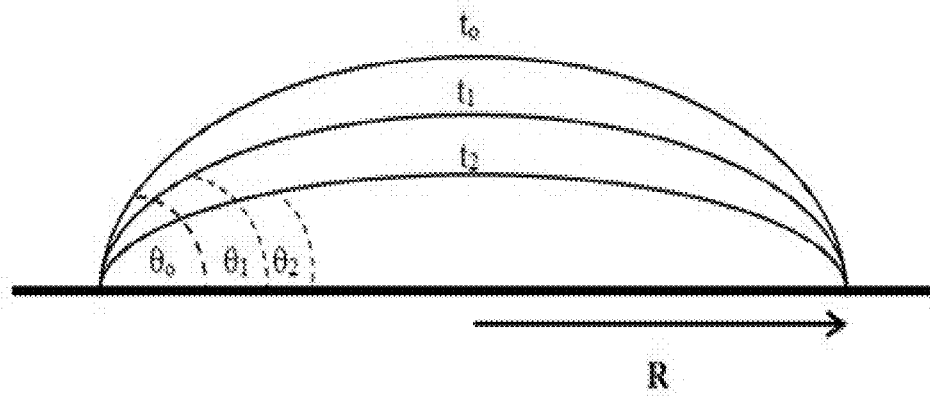
FIG. 3 is a schematic of a constant contact area diagram of a droplet evaporating over time according methods described herein.

FIG. 2 shows the optical penetration depth in water as a function of wavelength. Both LAD wavelengths are denoted by the vertical lines. Examples provided herein use laser sources at 1064 nm and 1850 nm wavelengths to heat water to enhance evaporation. The maximum sample thickness used in this study was approximately 2 mm. The 1064 nm wavelength corresponds to an optical penetration depth that is much larger (80 mm) than the sample size, which should provide volumetric heating of the sample. The 1850 nm laser couples more strongly to water and thus has a smaller (0.8 mm) penetration depth. The 1850 nm laser can heat using a low laser power, but may not allow for uniform heating of the sample. There is minimal absorption of key subcellular components such as DNA and proteins at these wavelengths.

This light-assisted drying technique has several advantages over drying methods that have been tested to date. The required equipment is relativity inexpensive making it appropriate for a wide range of applications. The system needed for light-assisted drying is scalable: it could be used on a small number of samples (e.g. clinical setting) or for industrial use (in-line processing). Thermal imaging allows for monitoring of the sample surface temperature during processing, which is not currently available for other techniques. Light-assisted drying also offers precise energy deposition into the samples that are being dehydrated. This is an important characteristic of this technique, as the energy deposition ultimately controls the drying rate and the end moisture content of the sample. The end moisture content drives many of the properties of the glassy state of the preservation matrix. In particular, the glass transition temperature is very sensitive to end moisture content, particularly at high glass transition temperatures/low end moisture contents. High glass transition temperatures are required for storage of the dried samples at supra-zero temperatures. This precision of energy delivery/end moisture content is not offered by other drying methods that have been used to date.

Droplet Drying

Figure 4:
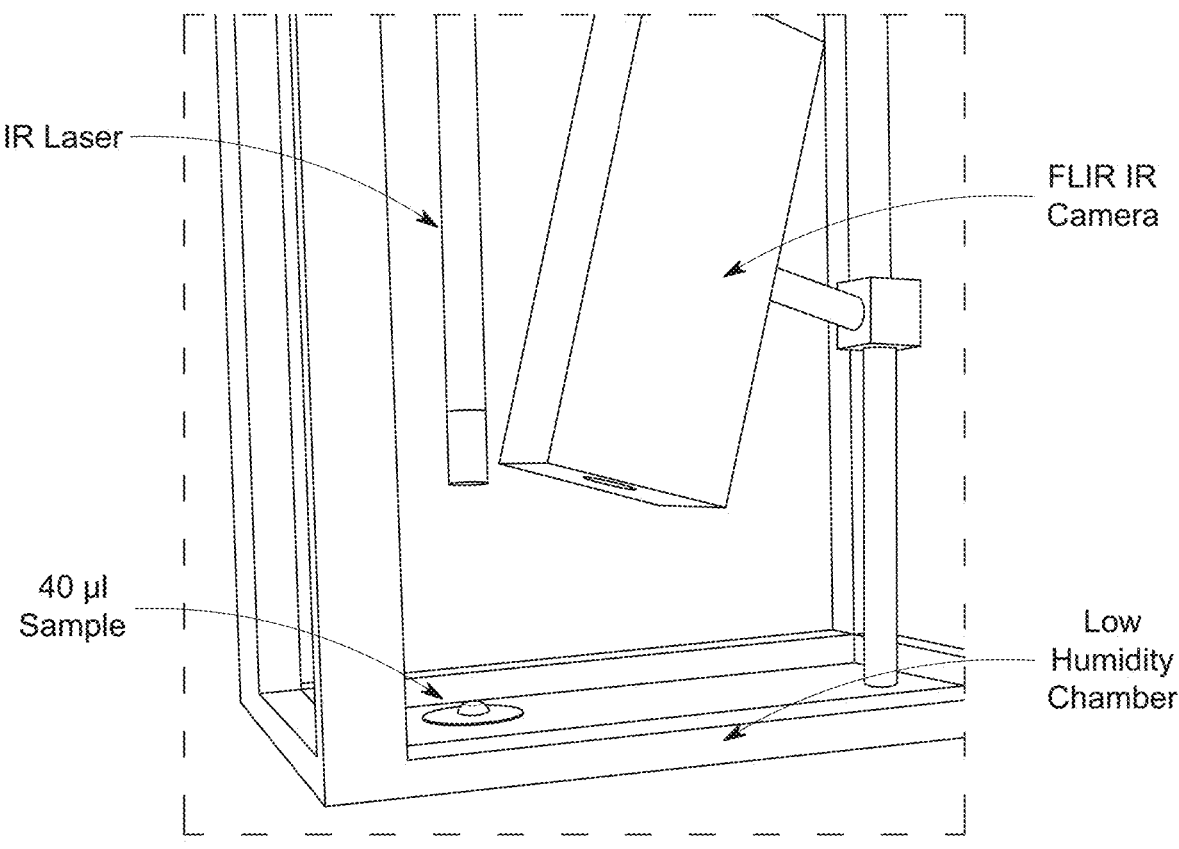
FIG. 4 is a schematic of an experimental set-up of light-assisted drying (LAD) technique within a controlled low relative humidity chamber according methods described herein.

As mentioned previously, LAD will be used to form amorphous solids by increasing evaporation from 40 μl droplets of proteins suspended in a trehalose solution. To better understand the anhydrous preservation of a droplet of proteins it is beneficial to first consider the drying process of a basic water droplet under standard atmospheric conditions. Typically, when a droplet is deposited on a substrate, such as borosilicate glass, it forms a spherical cap shape. Evaporation causes the volume of the drop to decrease. There are two types of evaporation modes; constant contact angle, where the radius of the droplet decreases over time, and constant contact area, where the contact angle decreases over time as shown in FIG. 4, which illustrates a constant contact area diagram of a droplet evaporating over time. The latter will be used for the best approximation of the drying technique employed according to methods described herein.

The drying rate of evaporation is governed by three main mechanisms. First, the phase change from liquid to vapor, in other words, the rate at which water molecules can cross the liquid-air border. As these molecules cross the interface, the air just above the surface becomes saturated. This leads to the second mechanism that controls evaporation, the rate at which water vapor molecules are transported from the droplet surface into the surrounding medium, called diffusive transport. The third mechanism is heat transfer to the liquid-air interface which induces evaporative cooling. Water molecules near the surface boundary will evaporate if they have sufficient kinetic energy to overcome liquid phase intermolecular forces. As these higher kinetic energy molecules escape, the remaining molecules have a lower kinetic energy. Since temperature is proportional to kinetic energy this means the droplet temperature will decrease.

The rate of volume change, evaporative flux, can be used to determine the lifetime of a droplet. Evaporative flux can be estimated using some simplifying approximations. Assume the droplet volume, V, is proportional to the cube of the droplet radius, R, and that the diffusion time of water vapor is given by $$t_d = \frac{R^2}{D} \qquad \text{[Equation 3]}$$

where D is the diffusion constant for water vapor in air. These relationships can be combined to give the rate at which the volume decreases over time $$\frac{dV}{dt} \sim -\frac{R^3}{r_d} = -DR \qquad \text{[Equation 4]}$$

A Marangoni stress (surface-tension gradient) will develop in a sessile drying droplet because of the thermal gradient across it arising from evaporative cooling. This drives a recirculating flow within the droplet. Methods described herein provide control over the lateral thermal gradient of the sample or preservation composition, which could lead to higher drying rates. Using a standard water-only droplet is effective for explaining evaporative rates during LAD processing, but it should be noted that the actual preservation solution contains trehalose molecules that will cause the sample to become increasingly viscous as it dries.

Example 2

Development of the LAD Process

The present Example illustrates the drying capabilities of LAD and optimization of processing parameters including laser wavelength, power, and sample substrate.

2.1 Introduction

In this example, light-assisted drying (LAD) is used to form an amorphous trehalose solid. LAD uses illumination by NIR laser light to assist in the formation of trehalose amorphous solids. Static air-drying of sugar solutions is dominated by evaporative cooling which causes the drying rate to slow substantially and allows for crystallization of the sugars. LAD selectively heats water to overcome cooling due to evaporation and accelerates dehydration of the samples. Two laser sources at 1064 nm and 1850 nm wavelengths were used to heat water in small volume samples. There is minimal absorption of key subcellular components such as DNA and proteins at these wavelengths.[37] In this paper, the water content of trehalose glasses formed via LAD using different laser wavelengths (1064 nm and 1850 nm), laser powers and processing times as well as their thermal histories during processing are presented. Two wavelengths with different absorption coefficients in water were chosen to test the effect of optical penetration depth in the sample on their resultant EMC. In addition, two drying substrates—borosilicate glass cover slips and a microfiber filter paper—were tested. Predicted glass transition temperatures for the trehalose preservation matrices produced via LAD are calculated and discussed.

2.2 Methods

A schematic of the experimental setup is shown in FIG. 4, which illustrates the set-up of light-assisted drying (LAD) technique within a controlled low relative humidity chamber. Two IPG Photonics laser sources were used separately for LAD processing, a continuous wave (CW) ytterbium fiber laser at 1064 nm (YLR-5-1064) and a CW thulium fiber laser at 1850 nm (TLM-5).

Both sources have maximum power outputs of 5 W with built in control of power and current, respectively. Both lasers emit collimated, single-mode, Gaussian beams with a FWHM spot sizes of ~4.5 mm which were measured using a BeamTrack 10A-PPS thermal sensor (Ophir Photonics). A FLIR SC655 mid-IR camera was used to record the temperature of samples in all tests. The camera has an array of 640×480 pixels and a maximum frame rate of 200 fps. This camera is sensitive from 7.5 to 14 microns, which is ideal for sensing temperature in the ranges that we are studying (35° C.-77° C.). All studies were performed in a humidity-controlled environment that was kept at approximately 11% relative humidity (RH). This was achieved by pumping dried air into a chamber containing the experimental setup and monitoring the RH with a temperature and RH logger (ONSET UX100-011). Maintaining a low relative humidity expedited the drying process.

All samples in the studies consisted of 40 µl droplets containing a model protein, egg white lysozyme (Worthington Biochemical LS002933), dissolved in drying solution (DS) at a concentration of 0.5 mg/ml. This was verified using the absorption of light at 280 nm with a microplate spectrophotometer (Bio-Tek Synergy HT). The DS consisted of 0.2 M disaccharide trehalose in 0.33×phosphate buffer solution (PBS). The dry weight of DS was determined through bake out method to be 7.01% the mass of a sample. Dry weight was adjusted to include the mass of the protein based on its concentration to determine the total dry weight.

For each test, a 40 µL droplet of the protein/drying solution was deposited onto a substrate and the initial mass was determined gravimetrically using a balance (RADWAG AS 82/220. R2) accurate to 0.01 mg. The sample was then moved into the humidity chamber for laser irradiation. The temperature of the sample was monitored during processing using the thermal camera. Maximum sample temperature was recorded as a function of time for each sample. After irradiation, the sample was removed from the humidity chamber and immediately massed again. End moisture content (EMC), which is a measure of the amount of water relative to the dry mass of a sample, was calculated as:

$$EMC = \frac{m_f - m_s - m_{dw}}{m_{dw}} \qquad \text{[Equation 5]}$$

where mf is the mass of the final sample including the mass of the substrate, ms, and mdw is the calculated dry weight of the initial sample.

Several different sets of processing parameters were tested and EMC as a function of LAD processing time (0-60 min) was determined (see Table 2). Each experiment was repeated three times (N=3), with the exception of the 1064 nm laser at Tmax=43.0±1.8° C. on coverslips at 30 and 60 minutes of processing (N=20) to test EMC repeatability. In addition, identical samples were allowed to air dry in the relative humidity chamber as a control.

TABLE 2

| | Beam Size (mm) | Power Density (W/cm²) | Processing Power (W) | $T_{max}$ (° C.) |
|---|---|---|---|---|
| Processing parameters tested for LAD drying. Wavelength, power, and substrate were varied. | | | | |
| 1850 nm | | | | |
| Coverslip | 4.009 | 0.88 | 0.11 | 35.0 ± 2.4 |
| | 4.009 | 1.42 | 0.18 | 42.4 ± 2.1 |
| | 4.009 | 4.04 | 0.51 | 77.6 ± 1.2 |
| Filter Paper | 24.054 | 0.18 | 0.86 | 36.4 ± 0.9 |
| | 24.054 | 0.29 | 1.36 | 43.9 ± 0.7 |
| | 24.054 | 1.01 | 4.60 | 72.5 ± 0.3 |
| 1064 nm | | | | |
| Coverslip | 4.864 | 16.15 | 3.00 | 35.2 ± 0.9 |
| | 4.864 | 26.92 | 5.00 | 43.0 ± 1.8 |

For the 1850 nm laser source, three laser powers were tested with each resulting in a different maximum temperature of the sample during processing. Various laser powers were tested to determine the effect of processing temperature on drying rate. Two different substrates were tested using the 1850 nm laser-18 mm diameter borosilicate glass coverslips (Fisherbrand 12-546) and 8 mm diameter borosilicate glass microfiber filter paper (Whatman 1821-021). The glass cover slips allow for easy recovery and rehydration of the proteins, while the filter paper is used in diagnostic assays. On the glass coverslips, the samples were droplets approximately 2 mm in thickness with a diameter of approximately 7 mm. A 1.0 ND filter (Newport 5214-A) was placed in line with the 1850 nm laser for processing samples on coverslips since the lowest available power setting caused excessive heating. On the filter paper, the samples dispersed in the paper such that they were a constant thickness of 0.675 mm, with diameter 8 mm. Filter paper samples have a constant sample thickness in comparison to their droplet counterparts so the Gaussian beams had to be flattened to allow for even heating across the samples. The 1850 nm laser beam was "flattened" using a reflective 6x beam expander (Thorlabs BE06R). Samples were placed in the middle of the expanded beam where there was minimal change in beam profile.

With the 1064 nm laser, two different laser powers were used for processing. Due to the lower absorption coefficient of water at 1064 nm, we were not able to achieve sample temperatures above about 42° C. even at the maximum power output of the laser. In addition, only glass coverslips were used as the substrate for these tests. Beam shaping the 1064 nm did not give a high enough energy density to achieve necessary processing temperatures to process filter paper samples.

2.3 Results & Analysis

Figure 5A:
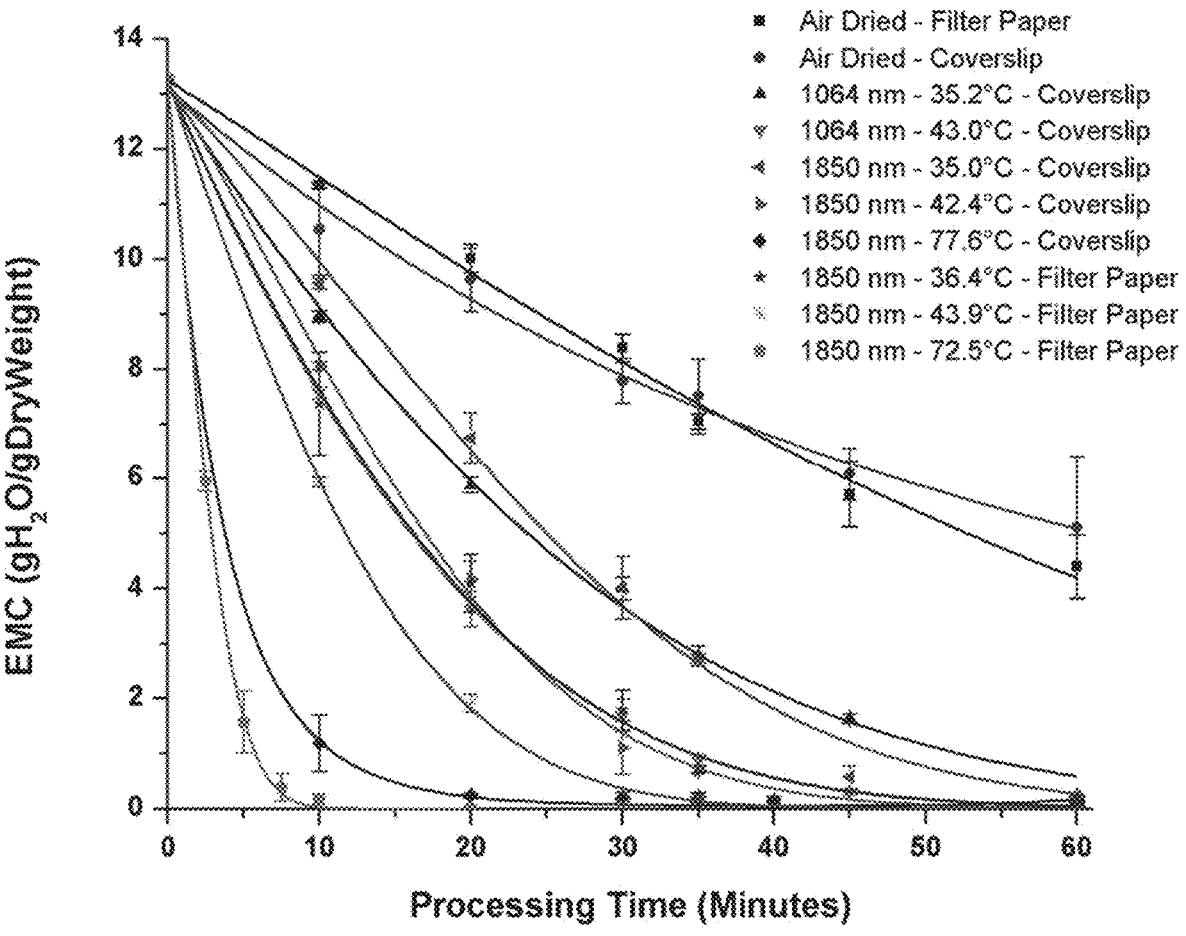
FIG. 5A-5C are graphs of water content (end moisture content; EMC) according to methods described herein.
Figure 5B:
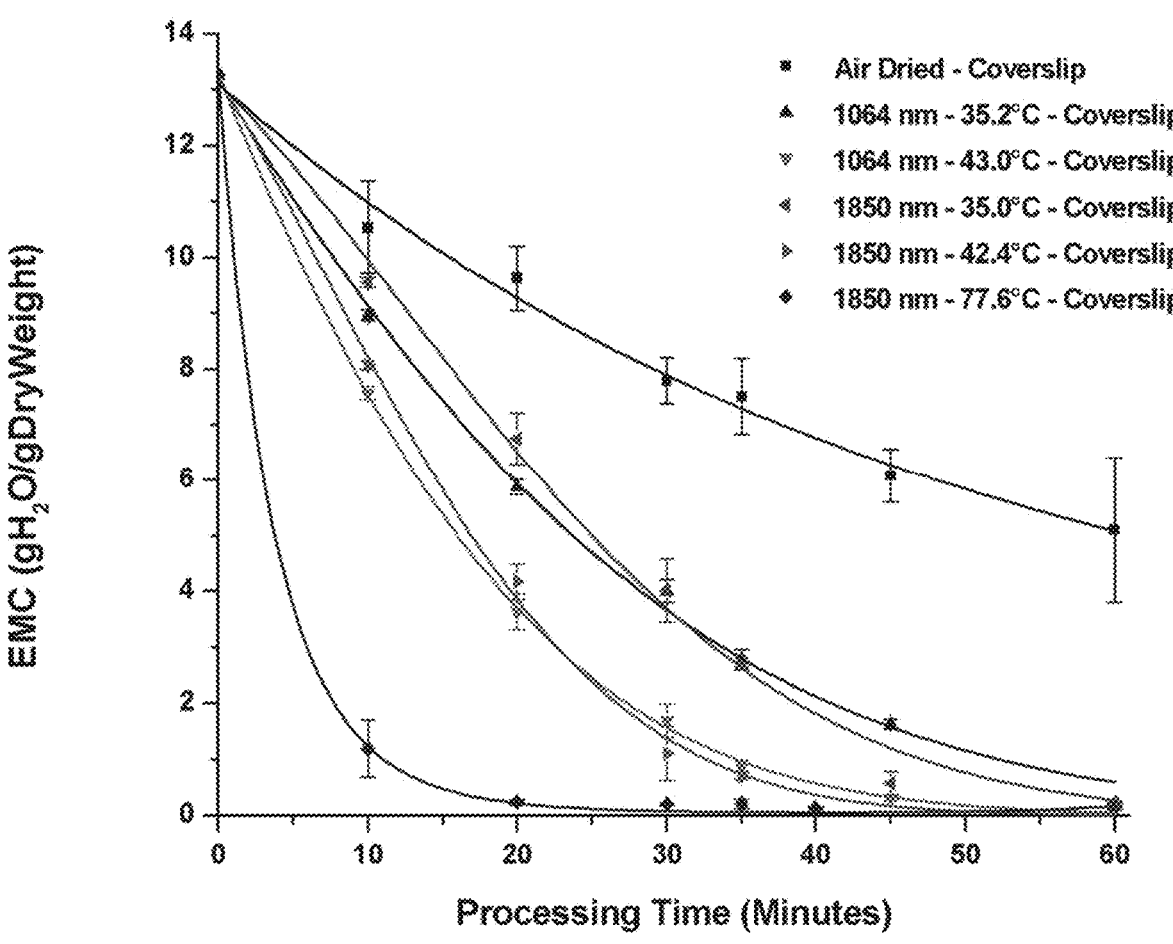
Figure 5C:
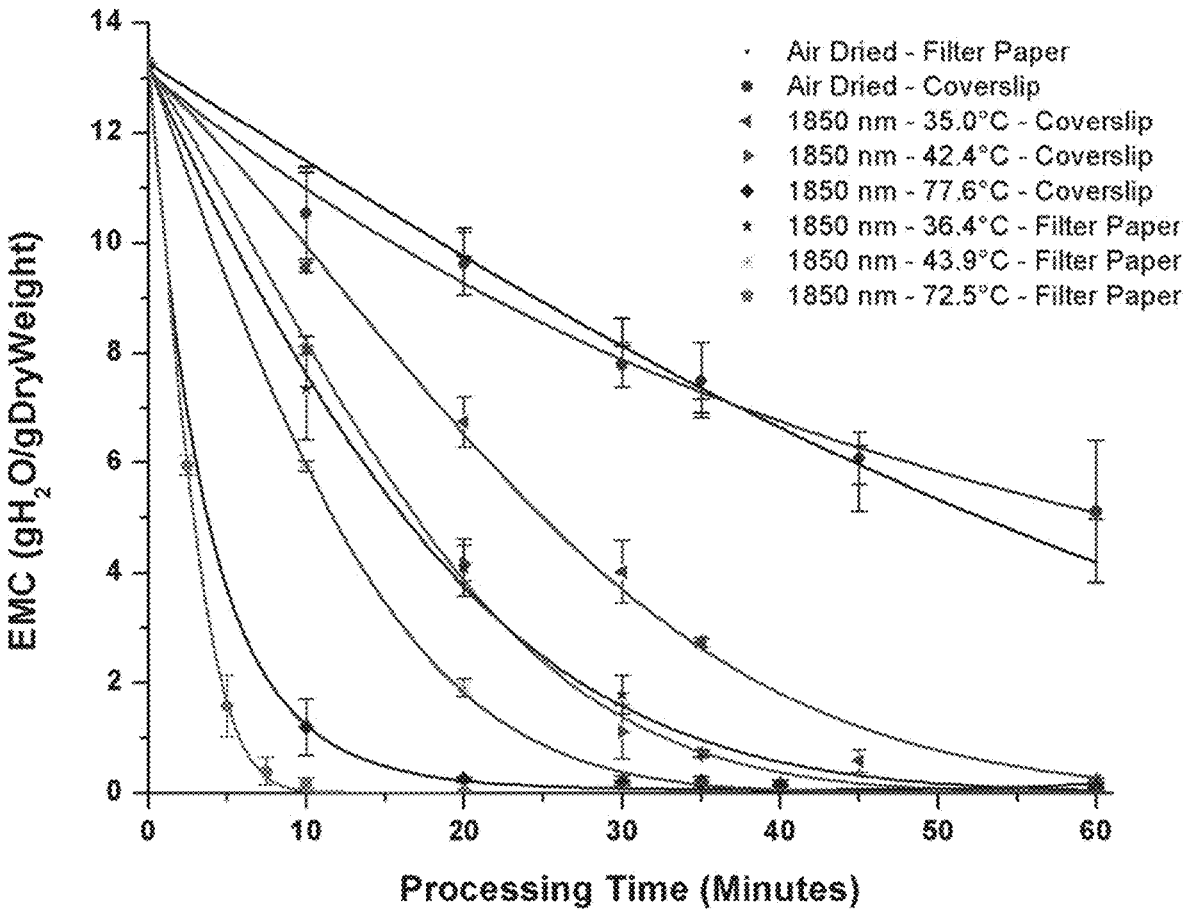

Drying curves summarizing the results are shown in FIGS. 5A-5C. Drying curves are graphs of EMC versus processing time and allow easy comparison of the EMC resulting from different sets of processing parameters.

Table 3 summarizes the resulting EMC, sample temperatures and predicted glass transition temperatures for 60 minute processing times for both lasers and for air drying. Air drying resulted in much slower drying and much larger EMC's at all processing times than either laser source. During air drying evaporation reduces the temperature of the sample and this decreases the evaporation rate. With light assisted drying, the laser adds energy to the drop to counteract/slow the effects of evaporative cooling.

TABLE 3

| Wavelength (nm) | Substrate | $T_{max}$ (° C.) | $T_p$ (minutes) | EMC (gH₂O/ gDryWeight) | $T_g$ (° C.) |
|---|---|---|---|---|---|
| EMC for each set of processing parameters and their associated glass transition temperatures. | | | | | |
| 1850 | Coverslip | 35.0 ± 2.4 | 60 | 0.22 ± 0.04 | −25.4 |
| | | 42.4 ± 2.1 | 60 | 0.16 ± 0.04 | −6.7 |
| | | 77.6 ± 1.2 | 60 | 0.14 ± 0.03 | 1.0 |
| | Filter Paper | 36.4 ± 0.9 | 60 | 0.06 ± 0.03 | 44.1 |
| | | 43.9 ± 0.7 | 60 | 0.03 ± 0.02 | 68.3 |
| | | 72.5 ± 0.3 | 20 | 0.03 ± 0.01 | 68.3 |
| 1064 | Coverslip | 43.0 ± 1.8 | 60 | 0.17 ± 0.04 | −10.3 |
| | | 35.2 ± 0.9 | 60 | 0.19 ± 0.03 | −16.8 |
| Air Drying | Coverslip | N/A | 60 | 5.11 ± 1.3 | −126.5 |
| | Filter Paper | N/A | 60 | 4.40 ± 0.6 | −125.2 |

Two laser wavelengths, 1064 nm and 1850 nm, were tested and compared for the drying capabilities of these two wavelengths for drops deposited on the glass coverslip substrate. To compare the resulting drying curves for these two wavelengths, laser powers were compared that resulted in the same maximum sample temperatures during processing. The temperatures were measured using the thermal camera. The performance of the lasers was compared at maximum sample temperatures of 35° C. and 42° C. For both lasers, as the maximum sample temperature increased from 35° C. to 42° C., the resulting EMC after 60 minutes is lower, as expected. The EMCs at 60 minutes for both laser sources were approximately the same. With the temperature of the drops being approximately the same, similar evaporation rates are expected. The power density used with the 1850 nm laser was much lower than that of the 1064 nm laser. This is because the water absorption coefficient for the 1850 nm laser is much higher than the 1064 nm laser. Therefore, even with less power per unit area, the sample heated at a similar rate due to more of that power being absorbed by the water. An additional temperature, 77° C., was then tested with the 1850 nm laser, which demonstrated an even further decrease of EMC. Overall both lasers have similar drying curves at the same processing temperature. The 1850 nm laser yields the lowest EMC but at the cost of a higher processing temperature. The low power needed to achieve this drying is an advantage but could also mean uneven sample heating because of the short penetration depth.

Looking at the drying curves in detail (see FIG. 5B) reveals an interesting result when comparing drying curves for each wavelength at similar processing temperatures. FIG. 5B graphs EMC as a function of processing time for drying on coverslips.

For short processing times (<30 minutes) the 1064 nm laser provides lower EMCs, but for processing times greater than 30 minutes the 1850 nm laser results in lower EMC until the drying curves converge at 60 minutes. This happens at both low and intermediate laser powers (35° C. and 42° C. sample temperatures). Also, the slope of the drying curve, which indicates the drying rate, is initially steeper for the 1064 nm laser, but after 30 minutes of processing time the drying rate of the 1850 nm laser is steeper. The absorption coefficient for the 1850 nm laser source may account for these differences in the drying curves. Initially, 1064 nm light couples effectively because there is more water to interact with. As the water evaporates, the 1064 nm source couples less strongly causing the amount of energy deposited to decrease, and subsequently the slope of the drying curve flattens. A possible method to combat this issue is to increase the power of the 1064 nm source during processing.

Recall the N=20 for the 1064 nm laser at ~43.0° C. at processing times of 30 and 60 minutes. Increasing the sample size from N=3 to N=20 resulted in a slight increase in average EMC and standard deviation at 30 minutes by 0.28±0.19 $gH_2O/gDryWeight$ (gdw) and a slight decrease at 60 minutes by 0.02±0.37 $gH_2O/gDryWeight$. This implies that LAD has better repeatability at low EMCs.

Two substrates—glass coverslips and filter paper—were tested with the 1850 nm laser (see FIG. 5C and Table 3) at sample temperatures of 35° C. and 42° C. FIG. 5C graphs EMC as a function of processing time for drying with 1850 nm laser.

Drying on the glass coverslips was slower than drying on the filter paper (for comparable sample temperatures); filter paper gave the lowest EMC. This is likely the result of the difference in surface tension of the sample on coverslips versus filter paper. On the coverslips, the sample maintains a hemispherical droplet shape, while on the filter paper the drop spreads out and assumes a 2D planer structure. The surface tension of the droplets on coverslips decreases the evaporation rate. The filter paper breaks up the droplet and spreads out so it is thinner, increasing surface area and reducing the surface tension. The 1850 nm laser source was tested of the filter paper at a higher power that resulted in a maximum sample temperature of 72° C. At the high temperature, the EMC at 20 minutes was comparable to 60 minutes of processing at a temperature of 36° C. on filter paper.

All light-assisted processing provided EMCs with good repeatability as measured by the small standard deviation of the mean at all processing times and for all laser parameters (see Table 3). This was not the case for air drying which had a very high variability in EMC. The repeatability of light-assisted drying is likely due to precise and repeatable energy deposition into the samples during processing.

Figures 6A, 6B:
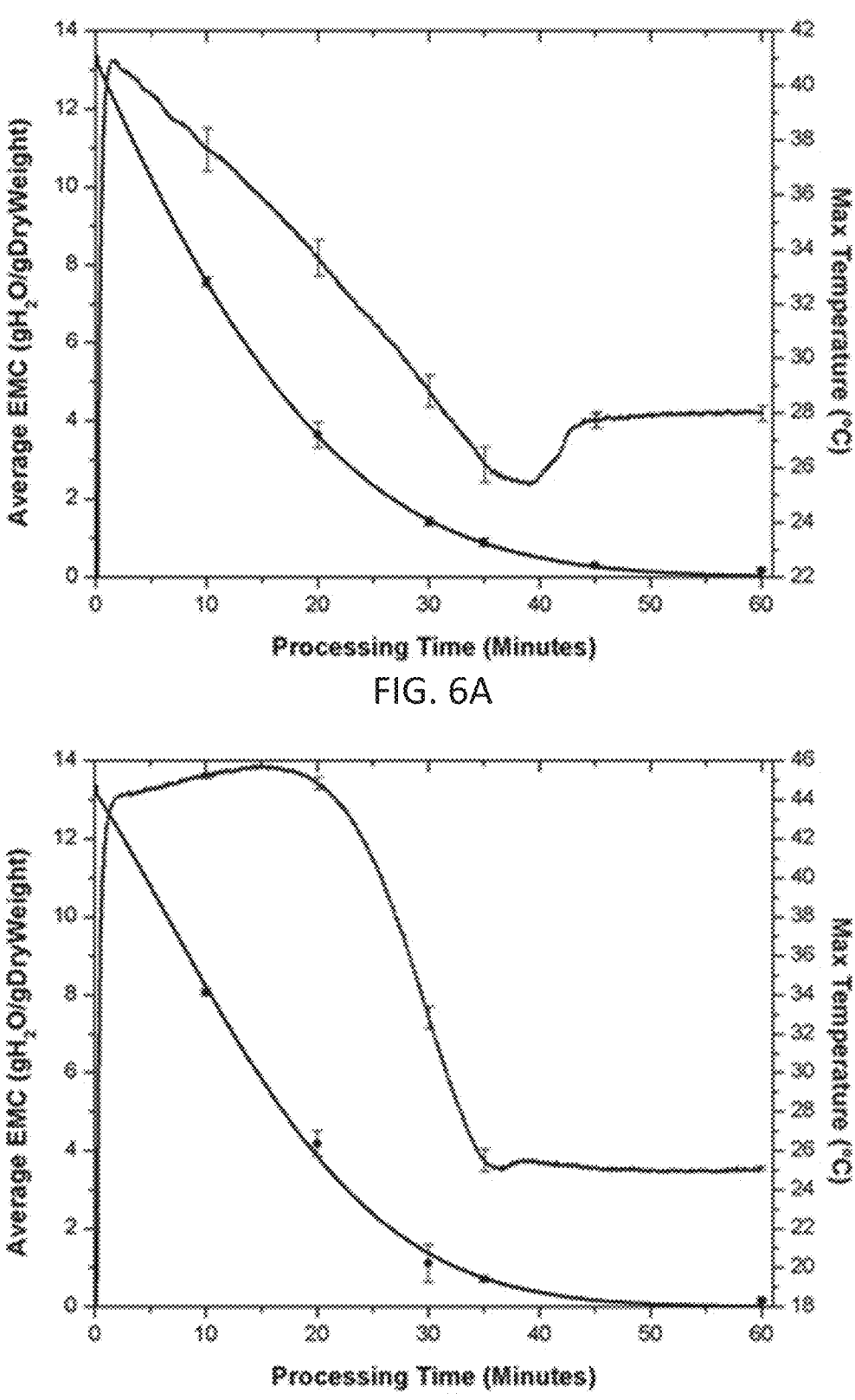
FIG. 6A-6C are graphs of thermal history with EMC curves according methods described herein.
Figure 6C:
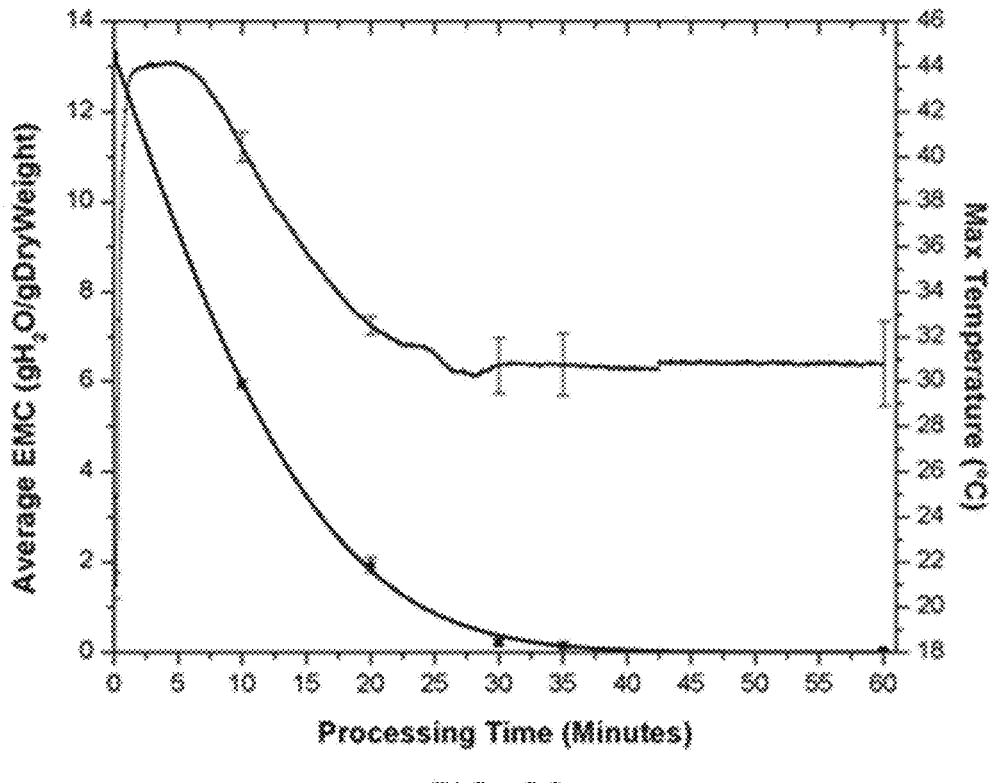

The maximum sample temperature was recorded during processing for each sample to give thermal history. The average maximum sample temperature for the 60 minute samples was averaged for an N=3 thermal history. In FIG. 6 the EMC was compared to the corresponding thermal history for each set of processing parameters at similar processing temperatures. FIG. 6A shows the thermal history with EMC curve for LAD processing of 1064 nm on coverslips. FIG. 6B shows the thermal history with EMC curve for LAD processing of 1850 nm on coverslips. FIG. 6C shows the thermal history with EMC curve for LAD processing of 1850 nm on filter paper.

In all cases there is initial heating of the drop as the laser energy is added. Once evaporation begins cooling occurs. All samples experience this cooling effect during processing but at different times. Evaporative cooling is removing more energy than the laser adds through absorption. As the sample evaporates the laser couples less strongly. To overcome evaporative cooling we would need to increase laser power.

Figure 7:
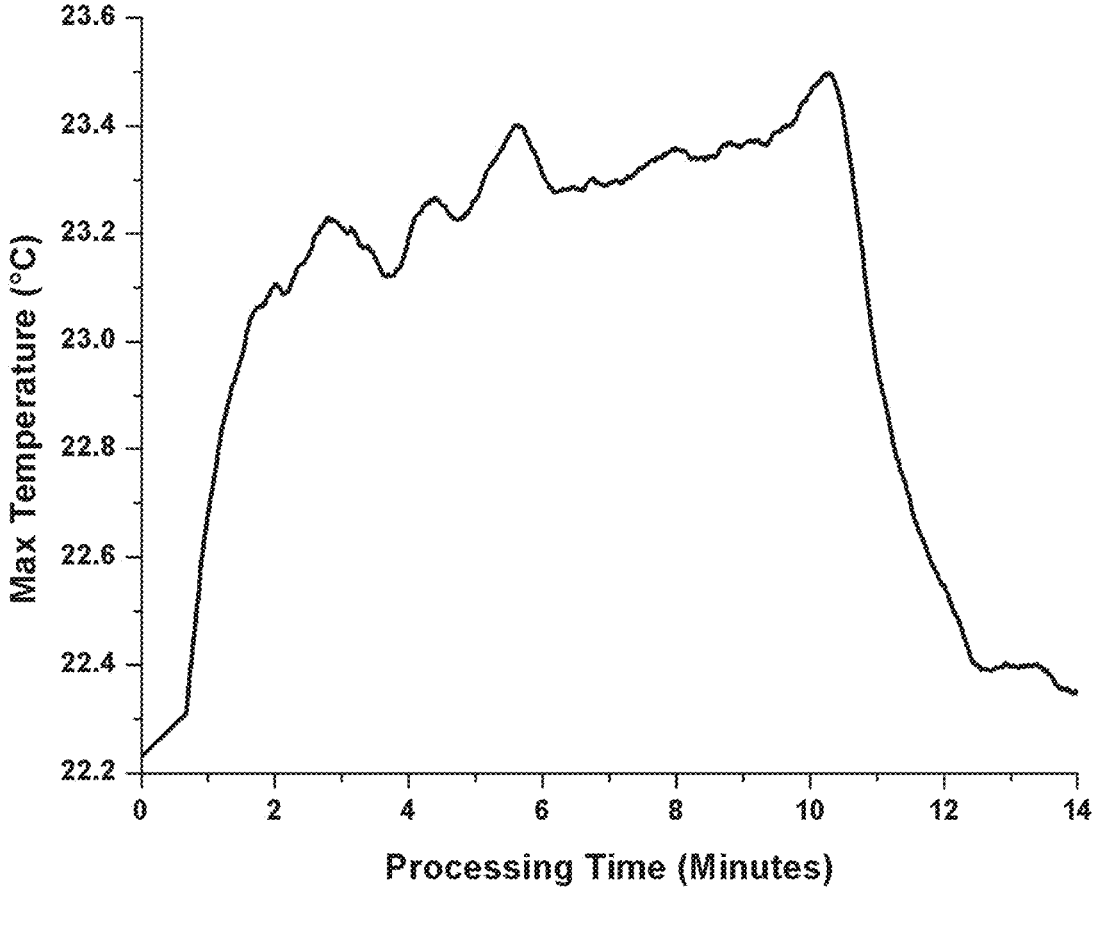
FIG. 7 is a graph of thermal history according methods described herein.

Maximum sample temperature for the 1064 nm on coverslips did not maintain peak temperature throughout processing, evaporative cooling was the dominate mechanism and the sample cooled until approximately 40 minutes of processing. The 1064 nm laser coupled less strongly with the water and its maximum power did not deliver sufficient energy to overcome evaporative cooling. Heating resumed again and plateaued at 28° C., most likely due to heating of the coverslip. FIG. 7 shows the heating of a glass coverslip with the 1064 nm laser at 5 W. The same characteristic plateau is observed at the end of the samples thermal histories. FIG. 7 illustrates the thermal history of borosilicate glass coverslip without sample under illumination with 1064 nm laser at 5 W. This is the same processing parameters associated with FIG. 5A. This heating curve corresponds to the heating observed during the end of LAD processing after most of the water has been removed from the sample.

Maximum temperature for the 1850 nm laser on coverslips showed an increase in sample temperature for the first 20 minutes because it coupled more strongly with water in the sample and delivered sufficient energy to overcome evaporative cooling. At ~20 minutes the volume of water had decreased, therefore less energy was being delivered and evaporation caused a drop in temperature. After 35 minutes of processing we saw a small increase in temperature followed by a plateau at 25° C. caused by the heating of the coverslip.

Finally, maximum sample temperature for the 1850 nm laser on filter paper showed the same increase in sample temperature followed by a decrease from evaporative cooling and a small increase from substrate heating that was observed in the thermal history of 1850 nm coverslip drying but on a shorter timescale. Also note that the substrate heating of the filter paper plateaus at a higher temperature than the coverslip. This is likely because the filter paper fibers scatter the incoming light increasing the optical path length of the light in the substrate and allowing for more absorption.

For all LAD drying, the point at which substrate heating took effect was at an EMC=0.58±0.04 $gH_2O/gDryWeight$. This was because the volume of water left in the sample was low enough that there was negligible water absorption and laser energy was absorbed by the substrate.

2.4 Discussion

Both the 1064 nm and 1850 nm laser sources show promise for use in the preparation of trehalose glasses to be used for the preservation of proteins or other biologics. Table 3 shows the predicted storage temperatures ($T_g$) for the samples prepared in this study. The estimated $T_g$ for drops dried on coverslips are close to 0° C. This is an improvement compared to the sub-zero storage temperatures required for some proteins, but on par with lyophilized proteins that require cold chain storage. Finally, there are multiple ways to improve the $T_g$. Longer processing time is one option; however, with the drying curves flattening out substantially at processing times of 60 minutes, the additional drying observed past this point would likely be small. Adding more power would increase the sample temperature and would therefore increase the drying. With this solution comes the risk of damaging the embedded protein. Finally, a surfactant could be added to the solution to decrease surface tension, which would increase the drying rate.

The standard deviation of the technique is low compared to air drying, however future studies will take a closer look at repeatability, as slight variations at very low EMC can lead to large variations in $T_g$. It should be noted that gravimetrically determining EMC is only an indicator of the average EMC of the entire sample. This does not show the varying moisture contents across the sample, which would lead to a higher storage temperature that corresponds to the area of highest EMC.

The combination of the 1850 nm source and the filter paper substrate provided the best results. The predicted storage temperatures for the samples processed on filter paper are promising for storage at ambient temperatures. For example, after 60 minutes of processing the 1850 nm laser produced trehalose glasses with potential storage temperatures ranging from 47° C.-69° C. Light-assisted drying on filter paper is appropriate for use in diagnostic assays but not for protein therapeutics where biocompatibility of filter particulates needs to be considered.

Freeze drying can take multiple hours to complete. A LAD processing time of an hour is a considerable improvement. Light-assisted drying (LAD) offers a relatively inexpensive, compact method for initial processing and anhydrous preservation allows for low-maintenance storage after samples have been packaged. LAD has the potential to provide a processing and storage method for protein-based drugs and diagnostic assays by forming an amorphous material around the proteins that will maintain their structural conformation, while increasing shelf life by decreasing bioactivity.

Example 3

Characterization of LAD Processed and Stored Samples

The present example illustrates the optical characterization of LAD samples using polarized light imaging (PLI), scanning white light interferometry (SWLI), and Raman spectroscopy. Polarized light can be used to image crystal structures. SWLI is widely used for optical profiling and generates a height map across the sample that we can use to determine sample topography. Raman spectroscopy measures the frequency shift of inelastic scattered light. This technique is used for monitoring trehalose distribution.

PLI is used to measure the homogeneity of amorphous materials and locate areas of crystallization. We looked for crystallization immediately post LAD processing and also monitored the crystallization kinetics of the same samples stored in three different relative humidity (RH) environments. Localized areas of crystallization in the samples can act as nucleation points and increase the rate of crystallization as well as lead to physical stress on some biologics embedded in the matrix. Polarized light microscopy has been used previously to analyze the presence of crystallization in sugars. When light passes through a linear polarizer it only transmits the component of the electric field that is in the direction of the transmission axis producing linearly polarized light. When that light passes through a secondary linear polarizer (analyzer) with a transmission axis oriented perpendicular to the first polarizer the light is completely absorbed. This is referred to as crossed polarizers. When a crystal is placed between a pair of crossed polarizers its optical anisotropy will cause the polarization state of linear light passing through it to rotate. Depending on the amount of rotation a component of the electric field will pass through the analyzer allowing it to be detected. In contrast, when an optically isotropic material, such as glass, is placed between crossed polarizers it will not undergo any change in polarization state and will not pass through the analyzer. This allows us to image crystals that might be present in amorphous trehalose glass.

Scanning white light interferometry (SWLI) is used to measure sample thickness and surface morphology after LAD processing and after long term (~1 month) storage at low RH. In a Michaelson interferometric objective, white light is amplitude split into a fixed length reference beam and a measurement beam whose coherence plane matches the focal plane of the objective. Vertically scanning the measurement beam generates fringes as the coherence plane reflects off of the sample surface. The height value for each pixel across the sample corresponds to the z location of maximum fringe visibility. Variations in thickness across the sample may indicate an uneven distribution of the trehalose preservation matrix which could impact the overall functionality of embedded proteins.

Raman spectroscopy is used in conjunction with SWLI to investigate trehalose distribution across LAD processed samples. Photons incident on a molecule are predominately Rayleigh scattered (elastically scattered), and the energy of outgoing photons is equal to incoming photons. An electric field incident on a molecule induces a dipole moment that scatters light at the optical frequency of the incident wave. Molecular vibrations alter the polarizability of the molecule causing the incident photon to either lose energy by exciting the molecule to a higher vibrational state (Stokes shift) or gain energy by from a vibrationally excited molecule (anti-Stokes shift). This emitted light is a lower frequency or higher frequency than the incident light, respectively. Stokes shifted scattering is the predominate type of spectra because the thermal population of vibrational excited states are typically low in ambient environments. Raman shift spectra depend on the atoms comprising the molecule as well as their atomic arrangements. This makes it ideal for determining the unique spectra of various chemicals.

3.2.1 LAD Processing & Sample Solution

The LAD system with the 1064 nm laser (as described in Example 1) was used for processing. Samples were processed for 60 minutes at 5 W ($26.9 \ W/cm^2$). For each test, a 40 μL droplet of the protein/drying solution as previously discussed was deposited onto an 18 mm diameter borosilicate glass coverslip (12-546, Fisherbrand) substrate and the initial mass was determined gravimetrically using a 0.01 mg readability balance (AS 82/220. R2, RADWAG). A fiducial was marked on the edge of the coverslip to ensure consistent orientation for each measurement. The sample was then moved into the humidity chamber for laser irradiation. After irradiation, the sample was removed from the humidity chamber and immediately massed again and EMC was calculated.

3.2.2 Sample Storage Conditions

All samples were stored individually in small volume containers above a saturated salt solution of lithium chloride (LiCl) (ChemCenter) and tested at various storage times (ts). The RH of the LiCl saturated salt was 14.3±0.5 RH. This was measured with an RH probe (HH314A, Omega) in a separate container for the duration of the samples storage. The PLI study also included two other sets of storage RH for testing: potassium acetate (KOAc) and magnesium nitrate (Mg(NO3)2) (Carolina Biological) at 24.2±1.9% RH and 47.2±5.8% RH respectively.

3.2.3 Polarized Light Imaging

Figure 8:
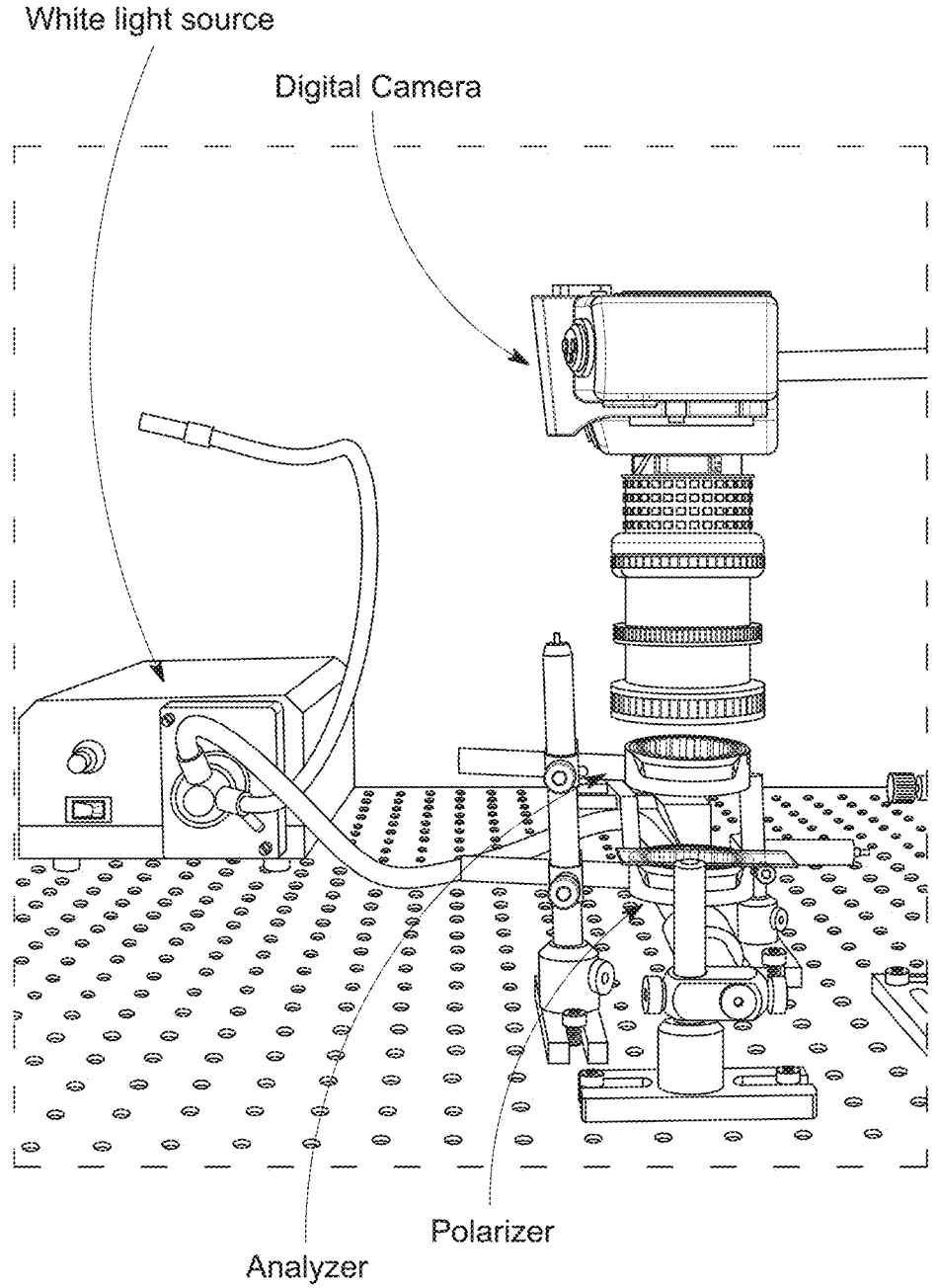
FIG. 8 is a schematic of polarized light imaging set-up according methods described herein.

The PLI experimental set-up (FIG. 8) consisted of a white light fiber optic illuminator (41720, Cole Palmer), two linear polarizers (LPVISE050-A, Thorlabs), with the second polarizer acting as an analyzer, and a digital camera (Nikon D100) aligned in the vertical direction. The camera was equipped with a Nikon 28-105 mm f/3.5-4.5 lens and manually focused on the image plane. The spatial resolution of the set-up was 10 μm/pixel. LAD samples (N=8) were processed as described in example section 3.2.1 and air dried samples (N=4) were made at the same time as LAD samples by drying at low RH (~14% RH) for 60 minutes. Samples were placed in between the polarizers on a glass microscope slide and imaged from above. Two images were taken: the first with the analyzer oriented at 0° to the polarizer and the second with the analyzer oriented at 90° to the polarizer.

Samples were imaged and massed immediately after LAD processing then placed in low RH containers previously mentioned. They were then imaged and massed every 30 minutes for the first two hours in storage, then every hour for the next 2 to 5 hours and once a day after that.

3.2.4 Scanning White Light Interferometry

Sample thickness was measured with a Zygo Nexview Scanning White Light Interferometer (SWLI) with a 2.75× Michelson objective (spatial resolution: 5.88 μm/pixel). Samples (N=7) were LAD processed as previously mentioned and stored in LiCl (14.3±0.5% RH) containers and measured after one day of storage and again after 27 days of storage. EMC was measured just prior to all SWLI measurements. The data was exported into Matlab and HDFView for further processing. In Matlab transverse height was displayed as a color map across the sample, the average maximum height of the sample was calculated, and two diagonal cross sections were extracted. The HFView software was used to extract the non-interferometric images.

3.2.5 Raman Spectroscopy

Figure 9:
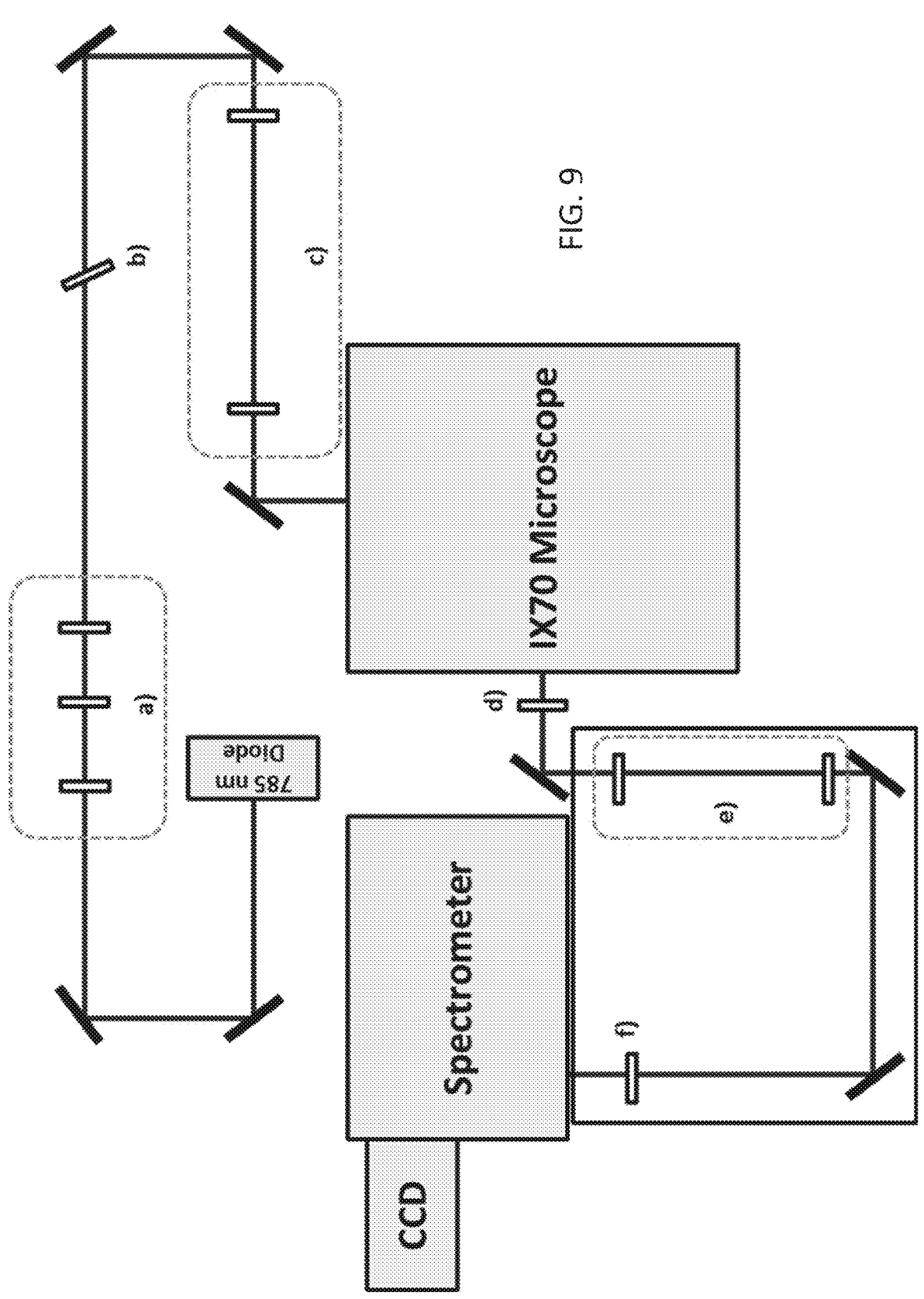
FIG. 9 is a schematic illustration of a raman spectroscopy set-up according methods described herein.

Raman spectroscopy was used to measure the Raman shift of trehalose across LAD processed samples. A schematic of the Raman spectroscopy set-up is shown in FIG. 9, which shoes that the laser beam passes through a) a lens system with a 100 μm pinhole to clean up the intensity profile followed by a b) 785 nm notch filter to spectrally clean up the beam and then an c) expander into the microscope. The Raman signal from the sample exits the microscope and passes through an d) edge filter to remove the excitation wavelength. Then it goes through a e) beam expander and collimator before passing through a f) focusing lens into the spectrometer.

The excitation source was a 785 nm laser diode (BeamQ) with a power output of 200 mW, the beam passed through a 100 μm pinhole and 785 notch filter to spatially and spectrally clean up the beam. The beam was then expanded and collimated before entering an IX70 inverted microscope (Olympus). A 100× oil immersion objective was used to focus the light onto the sample. Raman signal from the sample was then collected back into the objective lens and directed into a spectrometer (SR-303i-B, Andor) and imaged with a CCD camera (DU420A-BR-DD, Andor) with a spectral resolution of 0.28 nm/pixel. The spectrometers center wavelength was set to 855.36 nm to exclude the laser line from the spectra and signals were taken at an exposure time of 5 seconds and 60 accumulations to achieve maximum signal to noise ratio.

Samples (N=5) were LAD processed and EMC was measured as previously mentioned followed by storage in LiCl (14.3±0.5% RH) containers. After one day of storage EMC was measured and SWLI was performed as described above. The following day the Raman shift spectra were taken at three separate locations across each sample. Each spectrum was background corrected and baseline corrected to remove the signal from the coverslip using Andor Solis software. Corrected spectra were exported to Matlab where they were Savitzy-Golay smoothed and then normalized to their maximum.

3.3.1 PLI & Effect of Storage RH on EMC

Figure 10A:
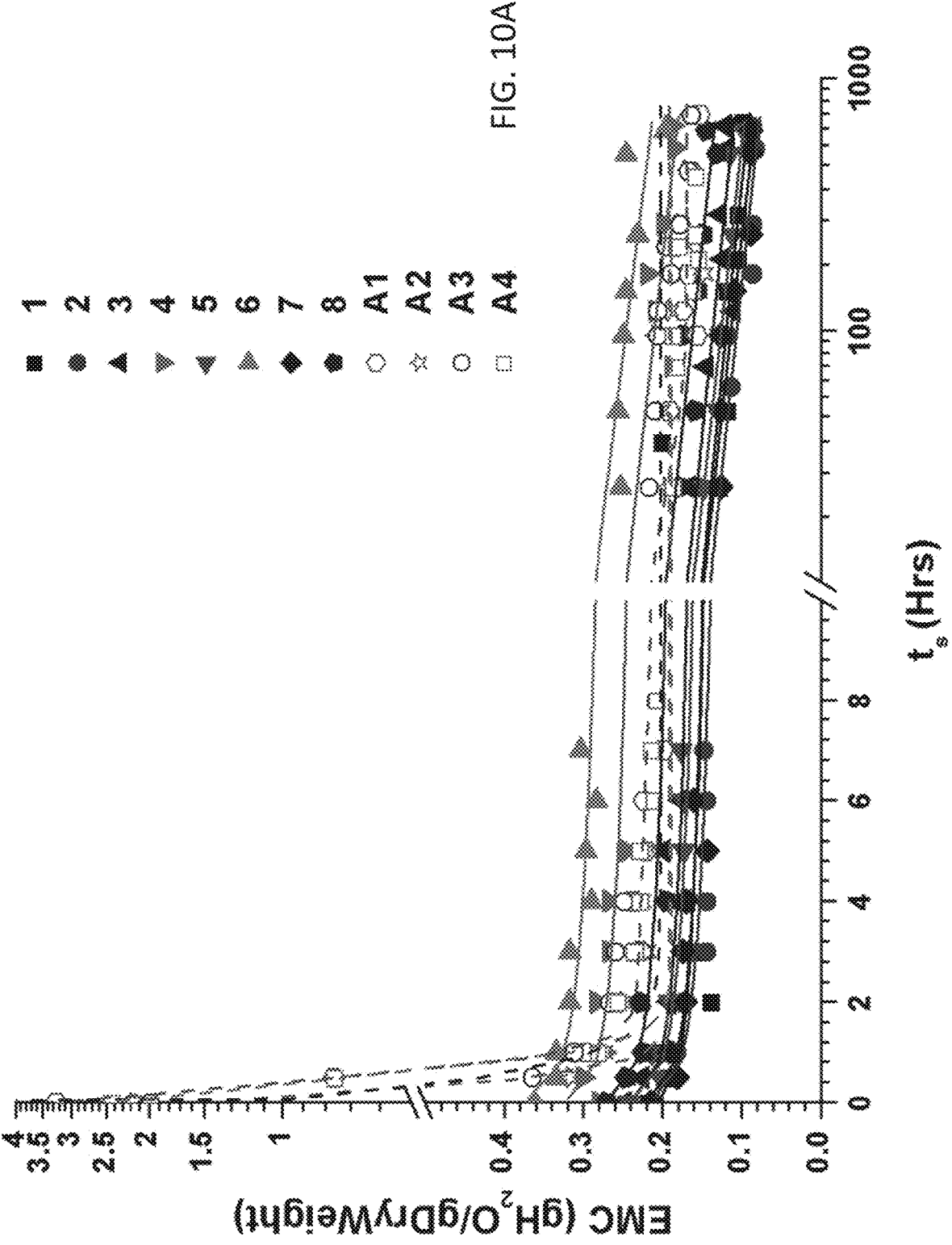
FIG. 10A-10D are graphs of EMC during storage according methods described herein.

For each set of RH EMC as a function of storage time was plotted. FIG. 10A shows the change in EMC as a function of storage time for LAD processed and air dried samples [air dried (A1-A4: exponential decay fit) and LAD (1-8: power fit) processed samples stored at 14.3±0.5% RH]. All air dried samples showed an exponential decrease in moisture content with the highest evaporation rate occurring during the first 3 hours and reached a moisture loss limit after 10 hours. After approximately 100 hours of storage samples approached their moisture loss limit which corresponded to the halt in crystal growth.

Figure 10B:
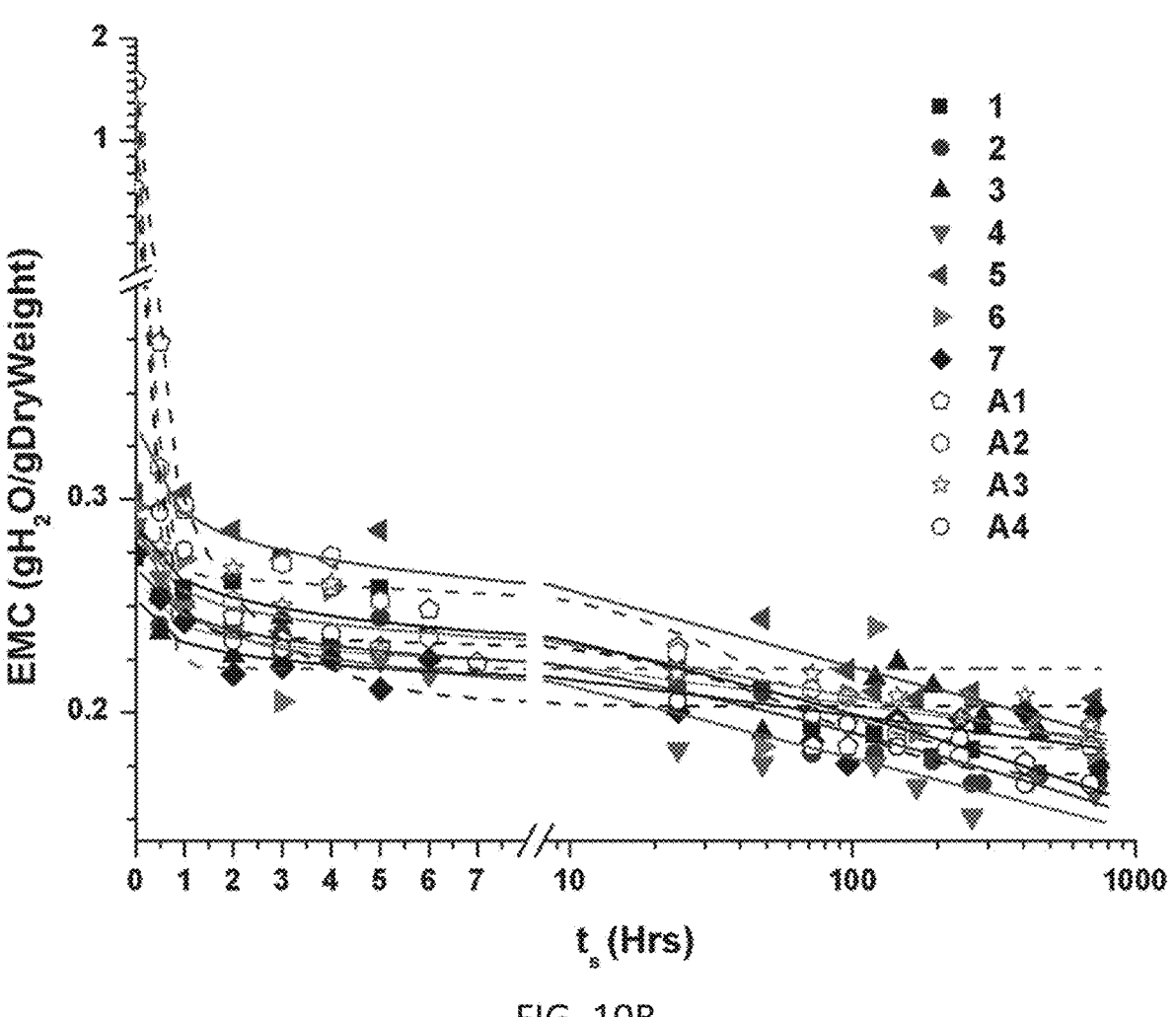

The second set of samples was stored at 24.2±1.9% RH. FIG. 10B shows EMC as a function of storage time for air dried (A1-A4: exponential decay fit) and LAD (1-7: power fit) processed samples stored at 24.2±1.9% RH. Air dried samples experienced an exponential decrease in EMC within 3 hours to within the same EMC area as the LAD processed sample. LAD samples experienced a nonlinear decrease in EMC over storage time with the largest drop in EMC occurring within the first 10 hours.

Figure 10C:
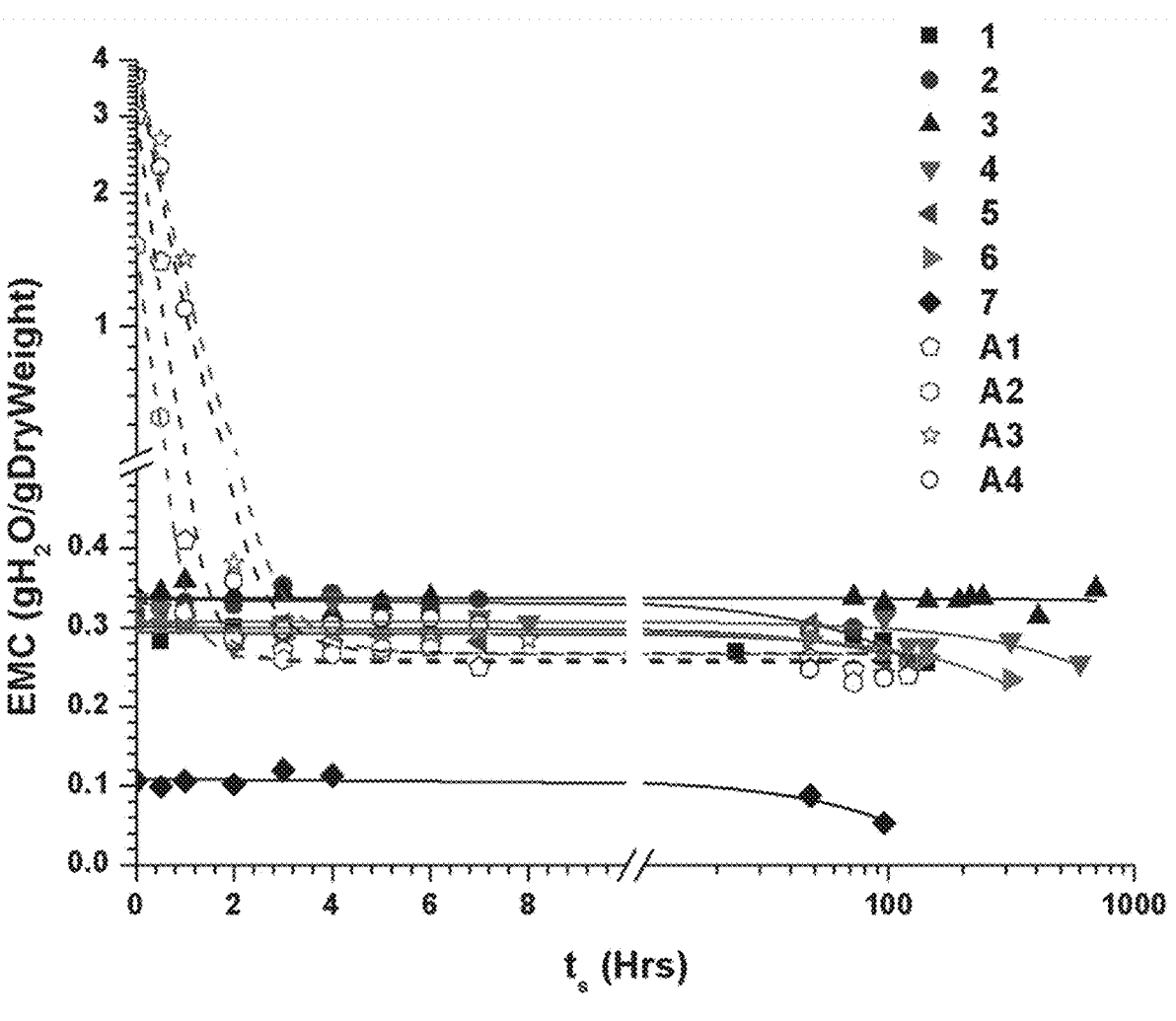

The final set of samples was stored at 47.2±5.8% RH. FIG. 10C shows the EMC of air dried (A1-A4: exponential decay fit) and LAD (1-7: power fit) samples during storage. Air dried samples highest rate of crystallization and highest rate of evaporation both occurred within 2 hours of storage. LAD samples experienced a linear decrease in EMC during storage after 10 hours. Sample 3 did not experience any decrease in EMC during storage.

Figure 10D:
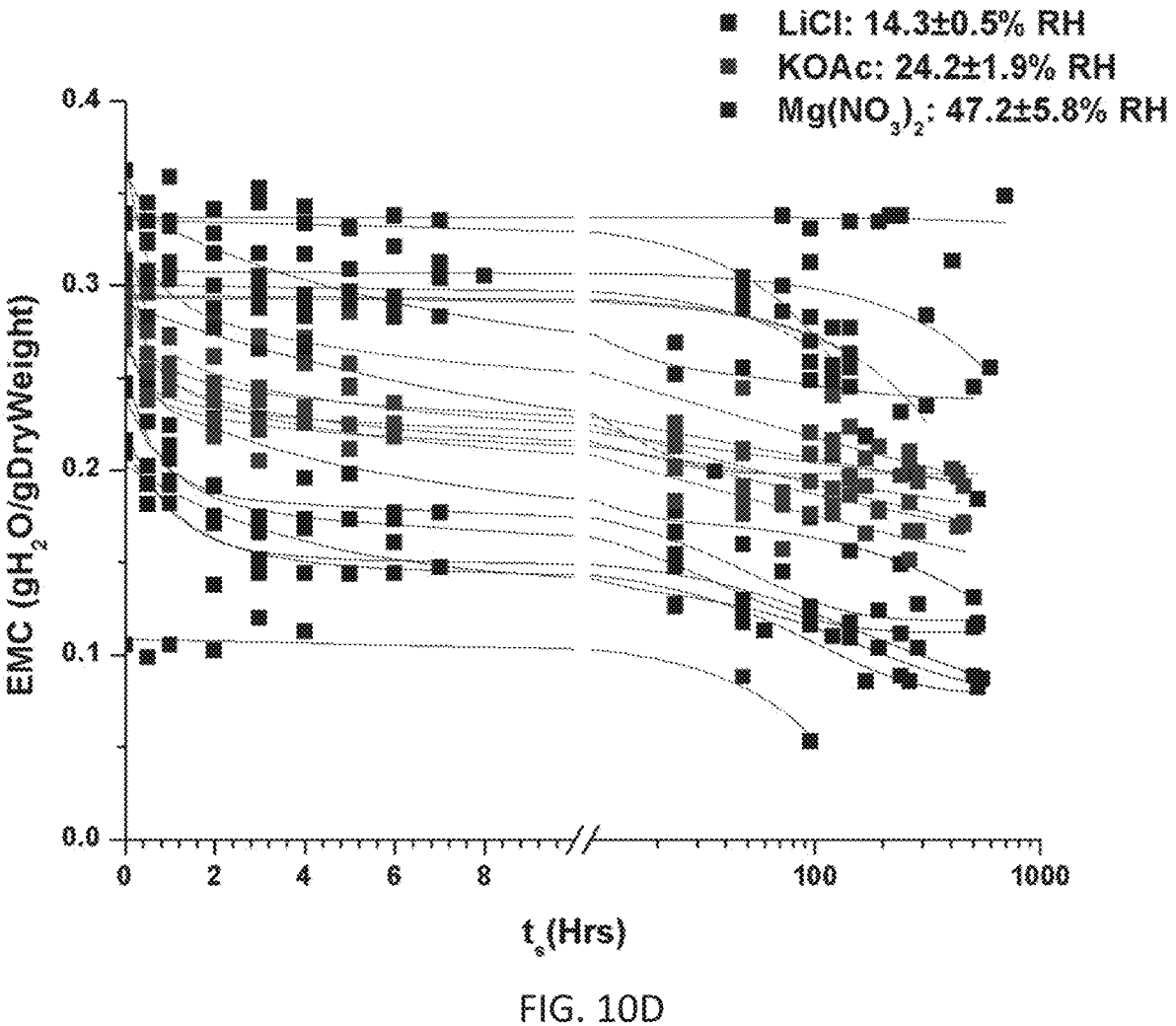

FIG. 10D shows EMC as a function of storage time for each set of RH. It was observed that the 14.3±0.5% RH generally yielded the lowest EMC over time. This is beneficial for achieving a higher glass transition temperature so we chose this as the storage RH for all future studies. Cracking observed near the end of storage at this RH is discussed in the next section.

3.3.2 PLI & Effect of Storage RH on Crystallization

Figure 11:
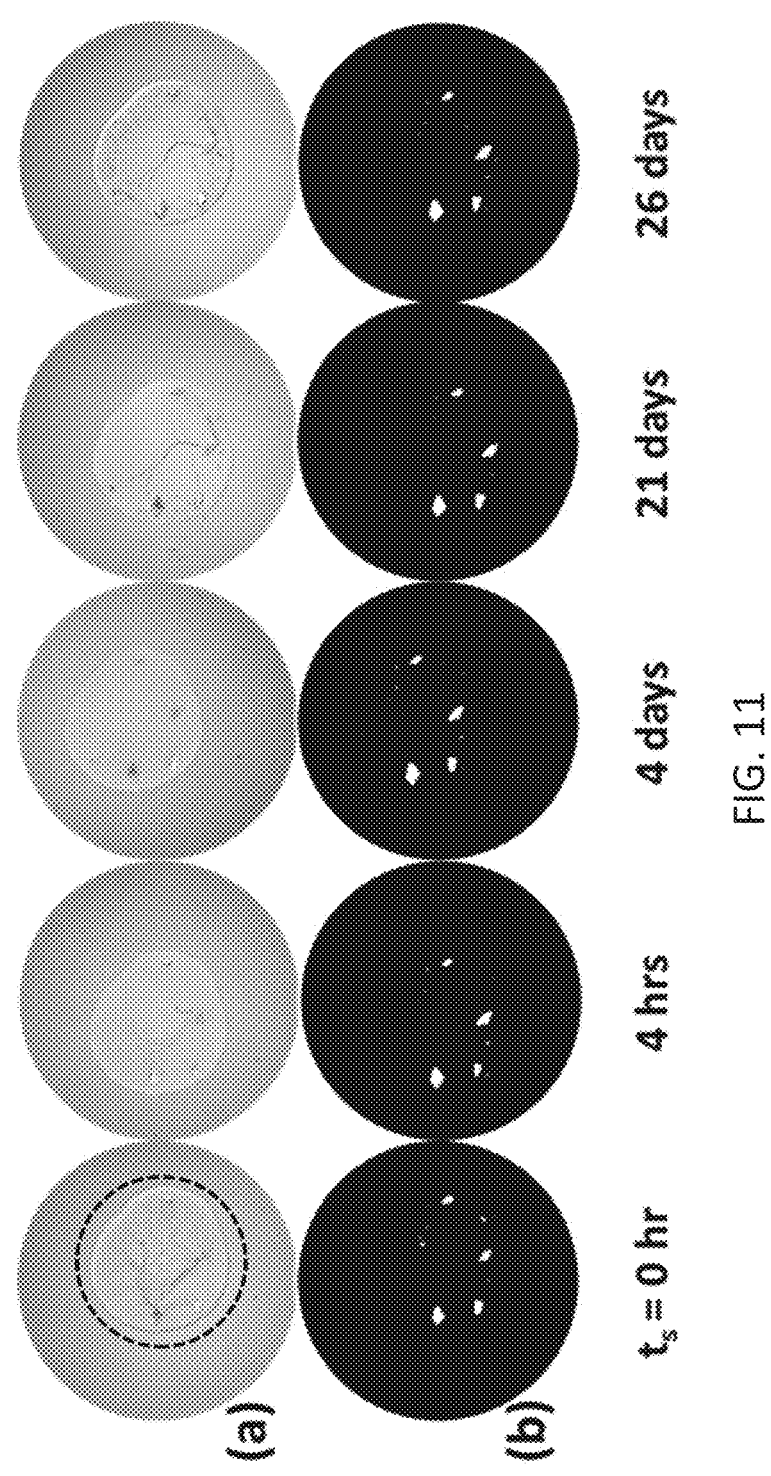
FIG. 11 is a cluster of images of crystallization over time according methods described herein.

PLI images were imported and analyzed in Matlab (R2017B). Each polarized image (image taken with crossed polarizers) was changed to a grayscale intensity image. A threshold intensity was established by finding the average maximum value of intensity of an area outside the sample plus two standard deviations. All pixels with intensities below the threshold value were zeroed. This was done to remove noise from the camera and particulates which could affect the polarization state of light. Crystal area was then measured by the number of pixels with intensity higher than zero in the crossed polarizer image of a user defined area from the uncrossed polarizer image. It is important to note that measured crystal area included noise from dust and particulates that also polarized light however this signal was present in all successive images and did not factor into measurement of crystal growth. For each set of RH crystallization as a function of storage time was graphed. FIG. 11 is an examples of the images obtained samples stored in LiCl saturated salt low RH containers. Panel a) shows the white light image of the sample and b) the corresponding crossed polarizer image after Matlab processing for crystal area measurement. The white area is crystallization present in the sample.

FIG. 11 shows the progression of a characteristic sample during storage at 14.3±0.5% RH. At this RH there were three distinct phases that occurred during storage: crystallization, wrinkling, and desiccation cracking. Crystallization occurs as water evaporates from a sugar solution. As the water evaporates the solution saturates and forms a precipitate in the form of a sugar crystal. In order for this to happen the evaporation has to be slow enough that the sugar has time to align itself into its crystalline pattern. The goal of LAD is to speed up evaporation enough so that this does not occur; however, some crystallization may result during processing or form over time as the amorphous solid relaxes. Samples immediately post processing had a 62.5% chance of having a small initial crystal. There was no relationship between initial crystallization and EMC post processing.

Figure 12A:
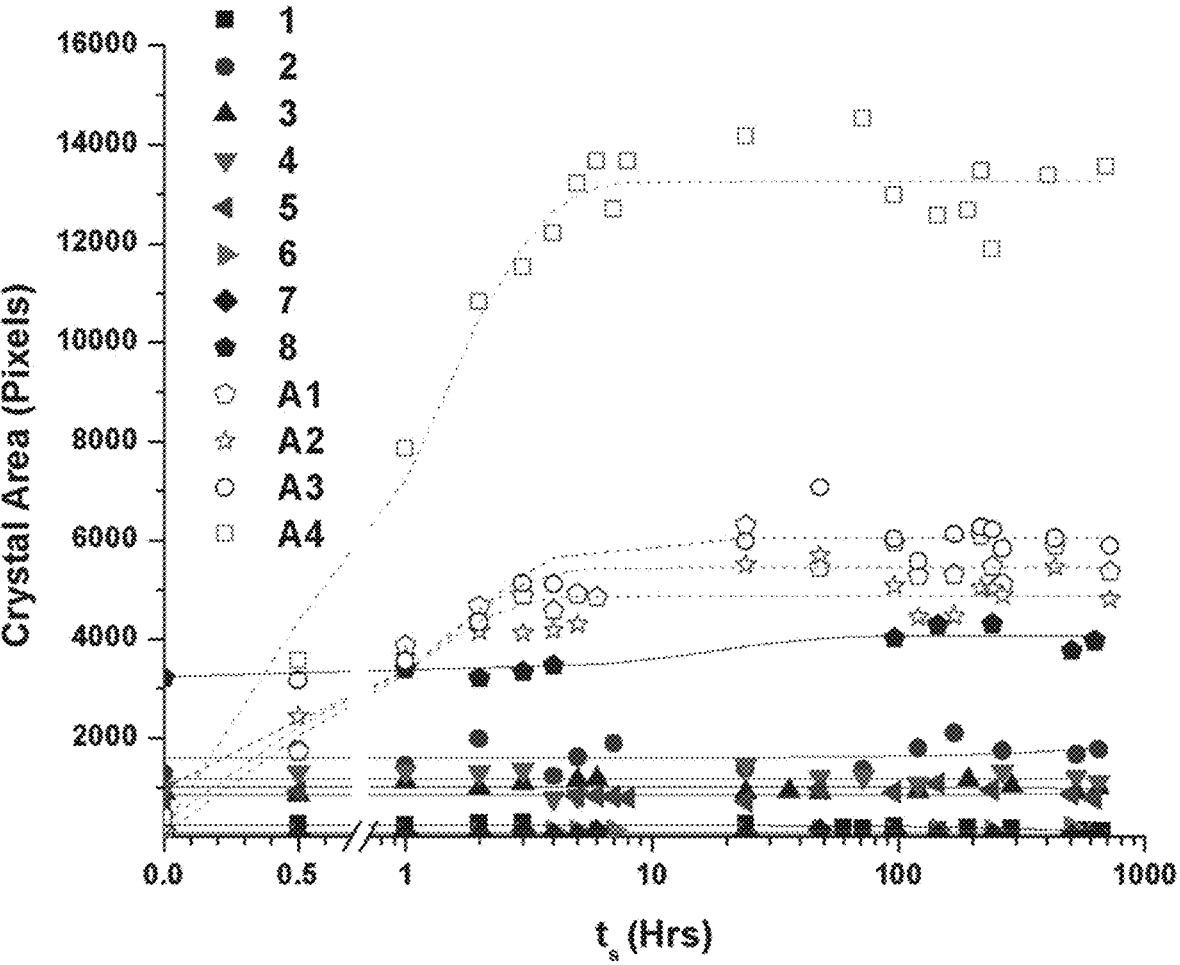
FIG. 12A-12D are graphs of crystal area during storage time according methods described herein.

FIG. 12A shows the crystal growth as a function of storage time for LAD (1-7: linear fit, 8: exponential fit) processed and air dried (A1-A4: exponential fit) samples stored at 14.3±0.5% RH. Air drying resulted in the highest amount of crystallization during storage with an exponential increase of crystallized area within 10 hours of storage corresponding to the time for which they experienced an exponential decrease in moisture content. They reached a moisture loss limit after 10 hours corresponding to the time at which crystal growth stopped.

Figure 12B:
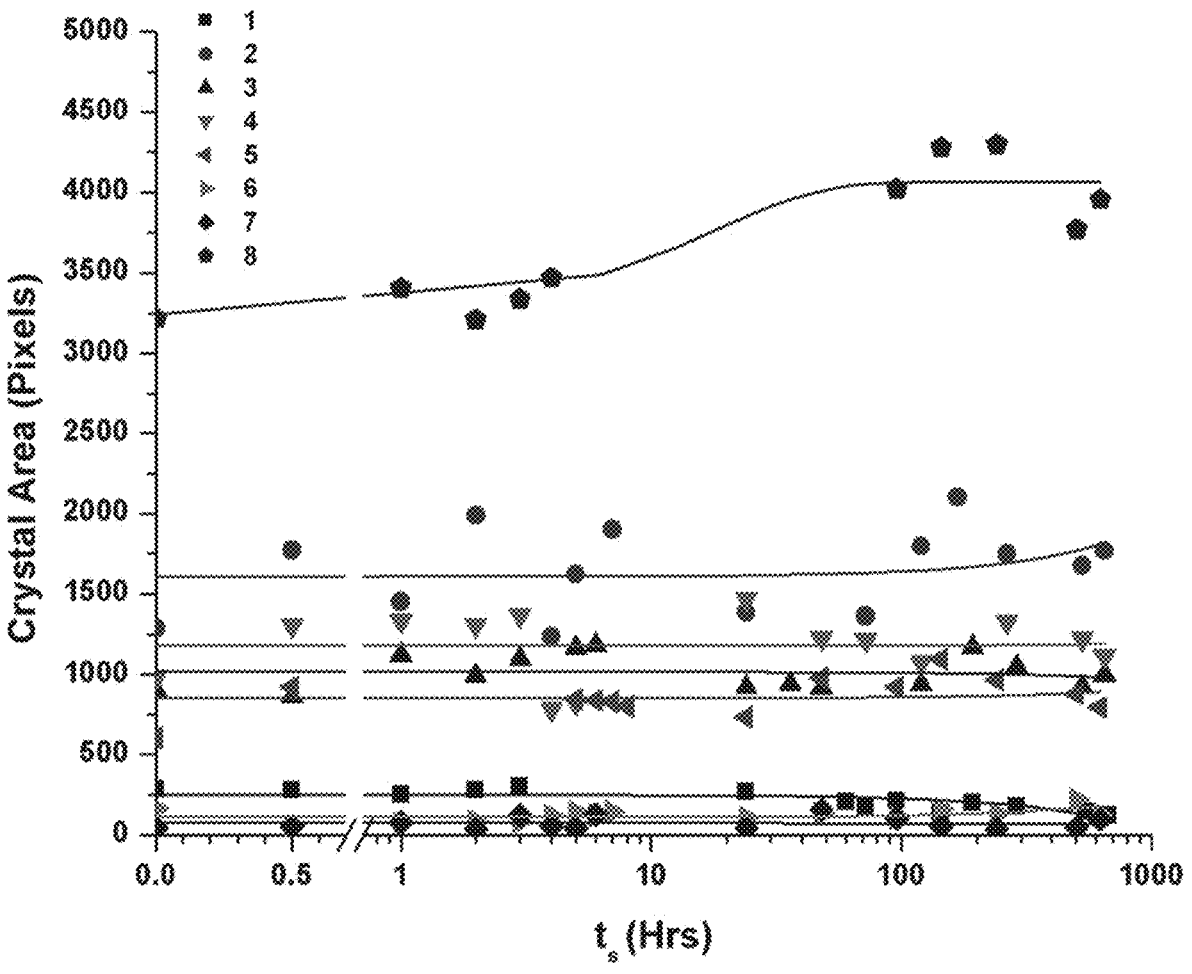

FIG. 12B graphs crystal area as a function of storage time for LAD processed samples stored at 14.3±0.5% RH. Of the 8 LAD processed samples (FIG. 12B) three had initial crystal area less than 500 pixels, upon inspection of their crossed and uncrossed polarizer images it was concluded that those three samples (1,6,7) did not have initial crystals and that the measured pixel area was equivalent to the dust measured in a sample free region.

The LAD samples with initial crystal area between 500 and 2000 pixels experienced minimal linear crystal growth during storage corresponding to their slight linear decrease in EMC. One LAD sample (8) contained an uncharacteristically large amount of crystallization (>3000 pixels) post LAD followed by an exponential increase in crystal area. Sample 8's uncharacteristically large initial crystal could have been caused by a larger particulate in the sample acting as a crystal seed. After approximately 100 hours of storage samples experienced a halt in crystal growth corresponding to their moisture loss limit.

This was also the earliest onset time when desiccation cracking was observed. Cracking was observed beginning on the edge of the drop. This exterior to interior crack formation indicates that a gel ring was forming on the edge and moving inward as the sample evaporated. The gel/substrate interface allowed for adhesion while the gel/air interface allowed for evaporation, when these processes competed tensile stresses caused cracks to form. This is in agreement with studies done on cracking of sessile droplets by other groups that observed the same exterior to interior radial cracking and found that cracking depends on the concentration gradient within the sample. This gradient is dependent on drying rate. The average storage time for desiccation cracking to begin was ts=324±159 hours.

Wrinkling of the samples, as shown in FIG. 11 (a) at ts=0 hr, only occurred when they were removed from their low RH environments into the higher RH of the room. It also only occurred during the first few hours after processing (ts=4±1.7 hrs). When placed back in low RH wrinkling dissipated quickly. Alternatively, if left for a longer period of time in high RH the sample eventually reached equilibrium and the wrinkling disappeared. This likely resulted from a change in volume at the surface of the sample. The samples mass distribution reached equilibrium while being processed at a low RH. When placed in a higher RH the surface absorbed moisture from the air causing it to superficially swell. The interior of the sample, which was contact pinned to the substrate, was no longer in equilibrium with the surface resulting in wrinkling.

Figure 12C:
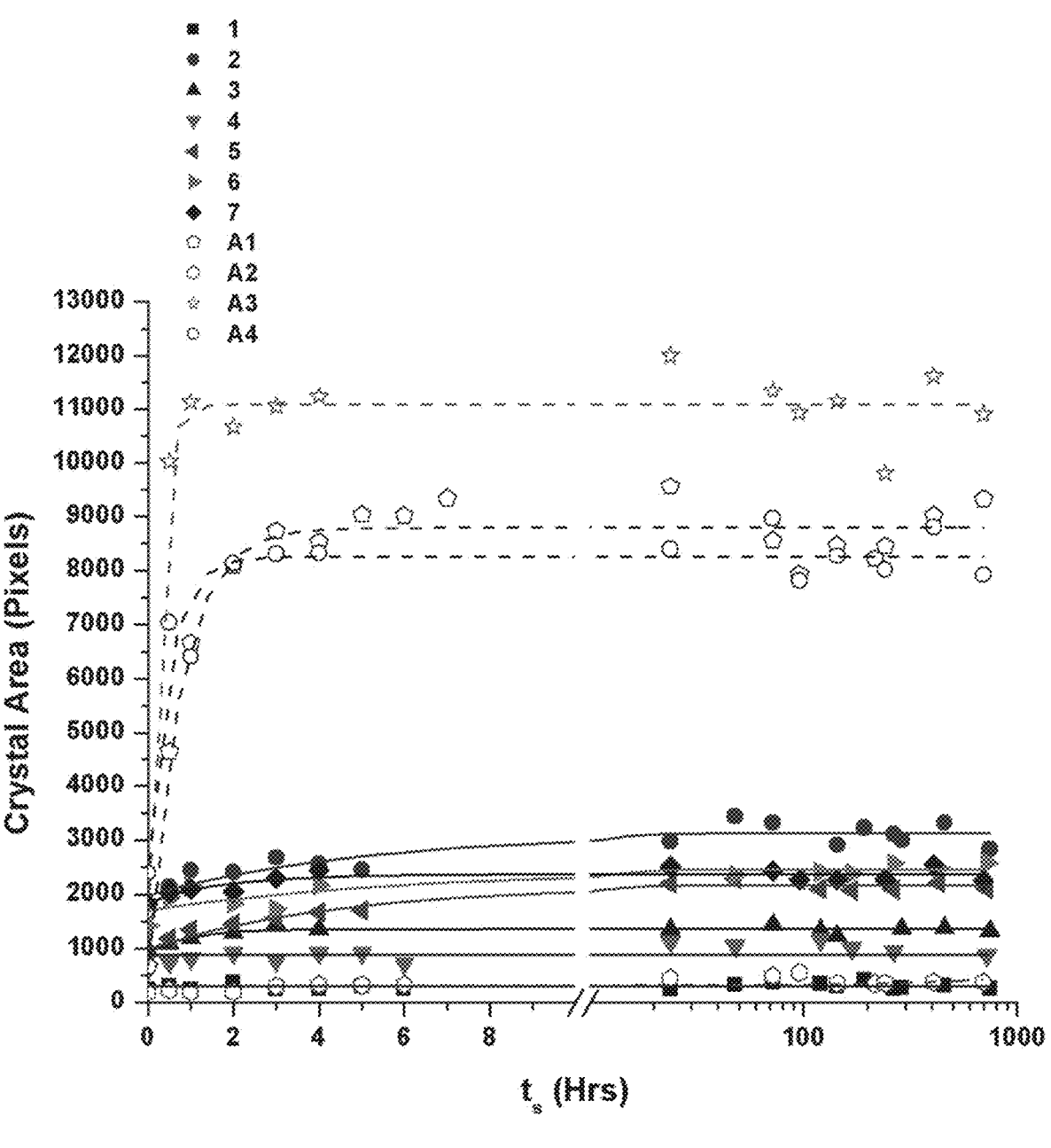
Figure 12D:
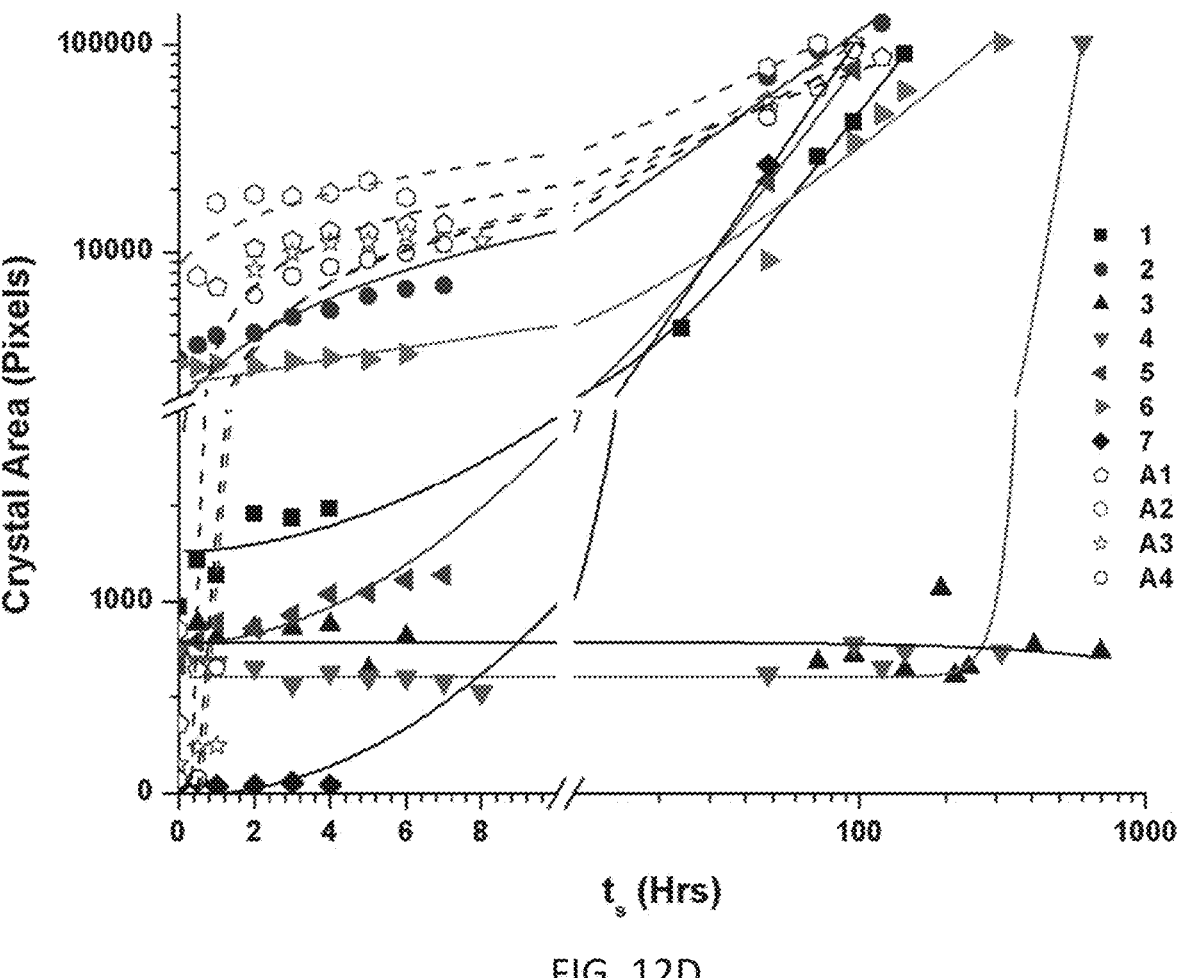

The second set of samples was stored at 24.2±1.9% RH. FIG. 12C shows crystal area as a function of storage time for air dried (A1, A3, A4: exponential fit, A2: linear fit) and LAD (1,4: linear fit, 2,3,5-7: exponential fit) processed samples stored at 24.2±1.9% RH. Air dried samples experienced the largest crystal growth over time. They experienced exponential growth during the first 2 hours, corresponding to the exponential decrease in EMC, followed by a halt in growth. This excluded one air dried sample (A2)

which did not form a crystal during storage at all; its measured initial crystal area was below 500 pixels and determined to be noise from particulates. Out of the LAD processed samples six (2-7) contained a small amount of initial crystallization, of which five (2,3,5-7) experienced a slight exponential crystal growth in the first 10 hours, corresponding to the largest drop in EMC, followed by no growth. The sample (4) with an initial crystal area below 1000 pixels only experienced a slight linear increase in growth. None of the samples stored at this relative humidity underwent wrinkling or cracking.

The final set of samples were stored at 47.2±5.8% RH, FIG. 21 shows the crystallization area as a function of storage time for air dried (A1-A4: power fit) and LAD (1, 2, 4-7: power fit, 3: linear fit) processed samples stored at 47.2±5.8% RH. Both air dried and LAD samples, with the exception of sample 3, crystal area increased non-linearly over storage time before reaching maximum crystallization. Air dried samples reached maximum crystallization faster than LAD processed. Air dried samples highest rate of crystallization and highest rate of evaporation both occurred within 2 hours of storage. LAD samples highest rate of crystallization occurred after 10 hours of storage which corresponded to the start of a linear decrease in EMC. Sample 3 had initial crystals upon removal from LAD but did not experience any crystal growth over time corresponding to its constant EMC over storage. This agrees with the trend that evaporation rate determines crystallization rate.

SWLI

Figure 13A:
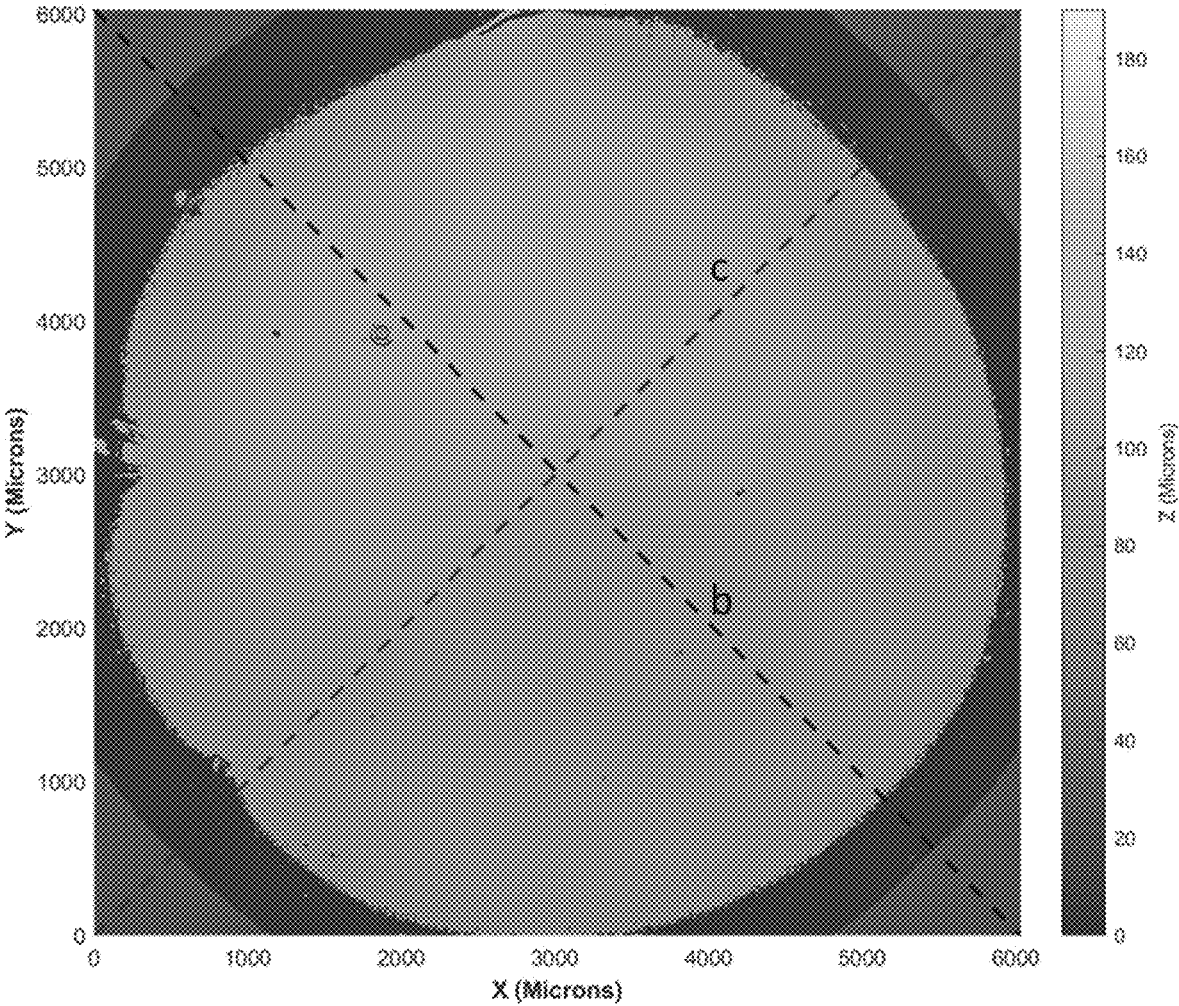
FIG. 13A is a topographical map captured via scanning white light interferometry (SWLI) of sample thickness according methods described herein.
Figures 13B, 13C:
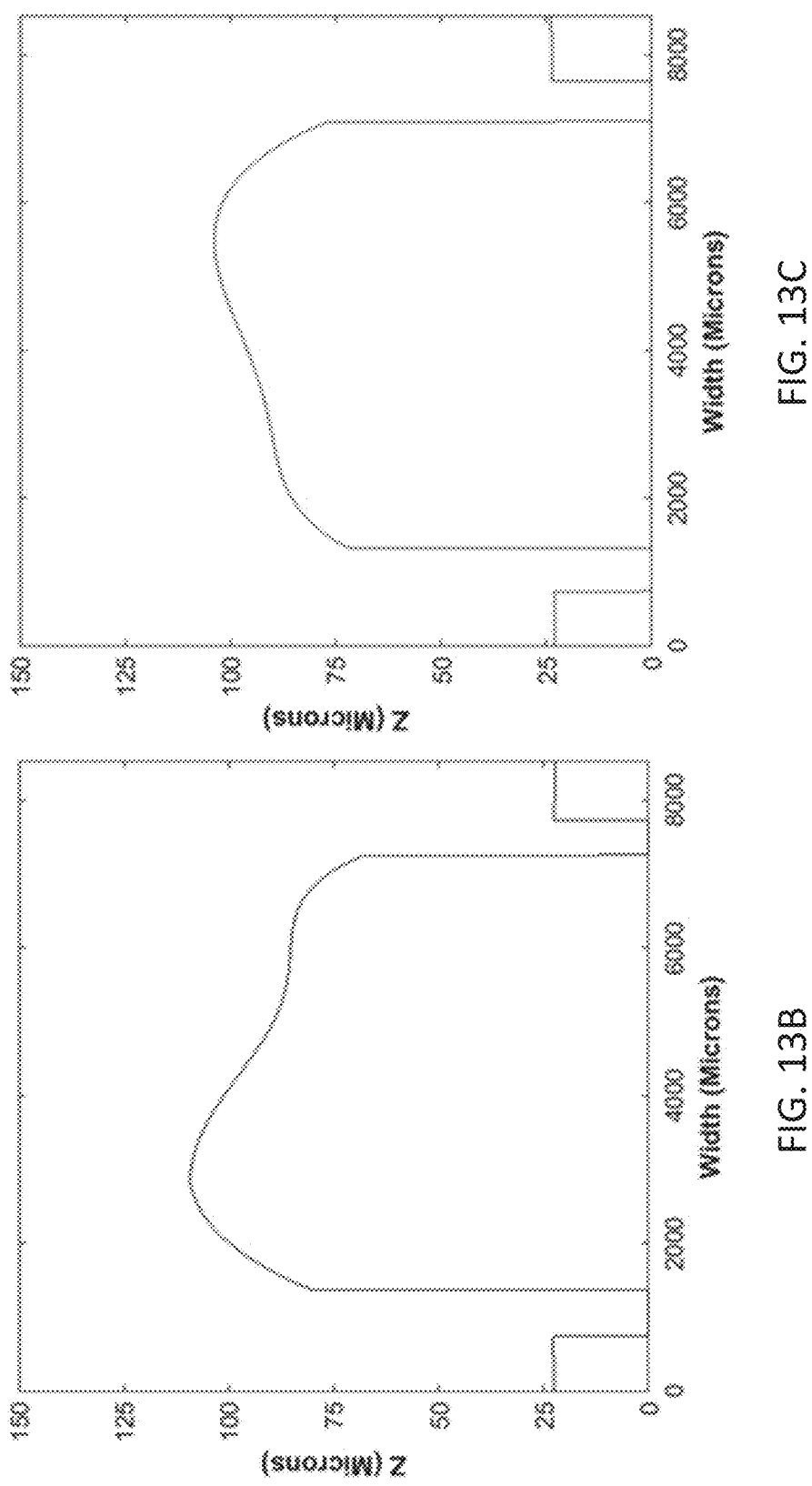
FIG. 13B is a graph representing the thickness of the (b) line in FIG. 13A.
FIG. 13C is a graph representing the thickness of the (c) line in FIG. 13A.

SWLI was used to characterize the topography and thickness of LAD processed samples. FIG. 13A shows a map of sample height. Two cross sections are marked as (c) and (b) dashed lines and their corresponding height profiles are displayed in FIG. 13C and FIG. 13B, respectively. The slope of the edges of the samples was outside the range of measurement capable by the Nexview, these areas display as zero height. The coverslip height shown on the edges of the profile was used as the base of the sample and subtracted from sample height to obtain thickness.

The average maximum thickness of LAD processed samples one day after storage (~14% RH) was 90.81±6.53 microns with an EMC of 0.16±0.04 $gH_2O/gDryWeight$. The average decrease in maximum sample thickness after 27 days of storage (~14% RH) was 8.65±1.71 microns corresponding to a decrease in EMC of 0.04±0.02 $gH_2O/gDry$-Weight. There was no statistically significant relationship between a decrease in EMC and a decrease in sample height, most likely because the changes were on such a small scale.

Profiles taken from all samples indicate that there is variability in thickness across the sample. A majority of samples exhibited a dome shape profile with the thickest part of the sample lying slightly off center. A few samples also showed a slight off center dip in the profile as well. The shape of the profile did not change over storage just the overall thickness. The off center nature could potentially be from variability of the position of the laser within the sample during processing.

Figures 14A, 14B:
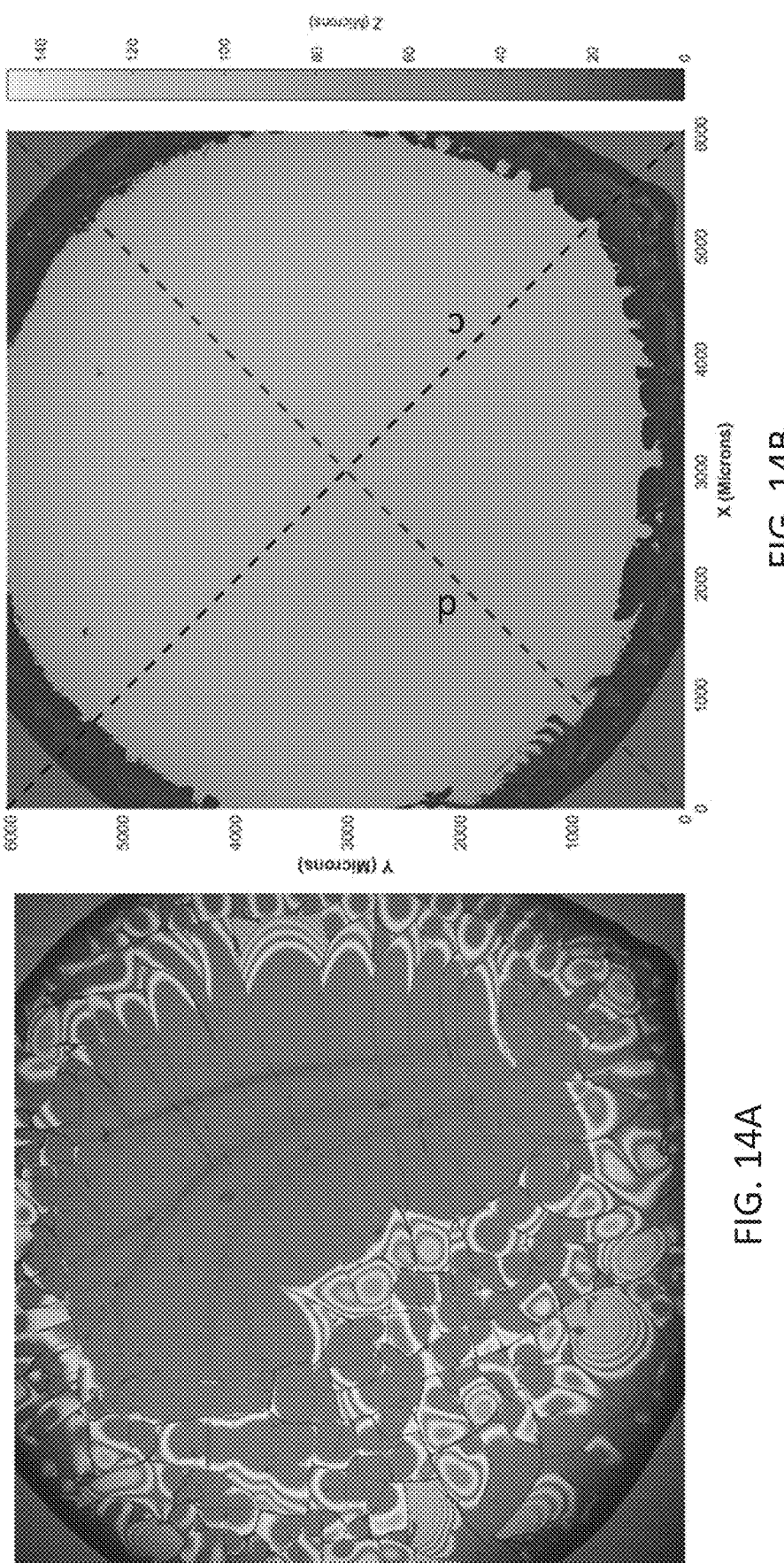
FIG. 14A is a non-interferometric image of a LAD processed sample after 27 days of storage at 14.3±0.5% RH.
FIG. 14B is a topographical map captured via SWLI of the sample in FIG. 14A.
Figure 14D:
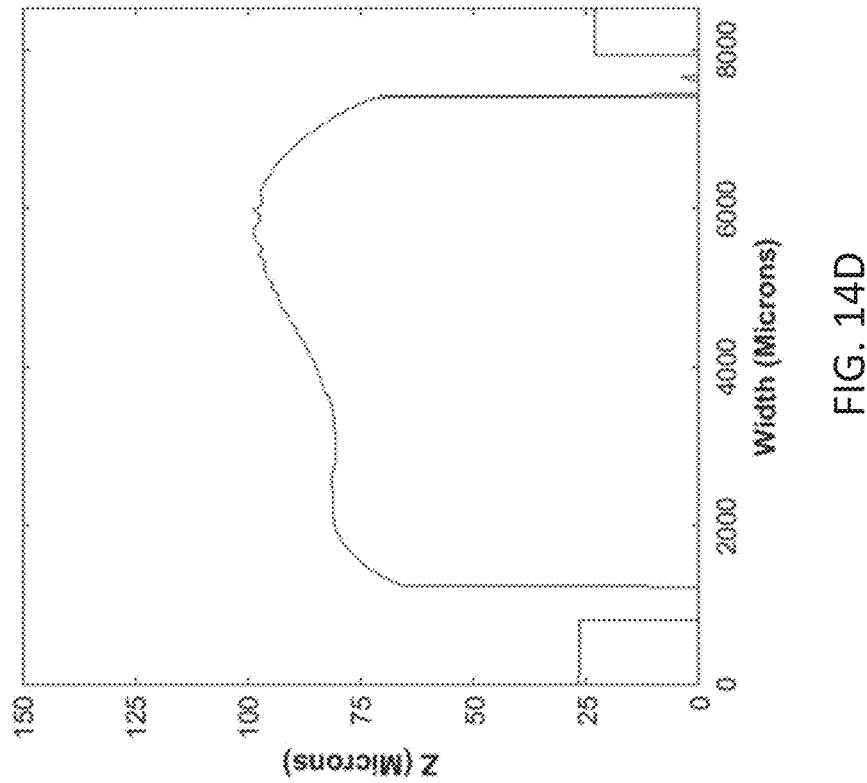
FIG. 14D is a graph representing the thickness of the (d) line in FIG. 14B.
Figure 14C:
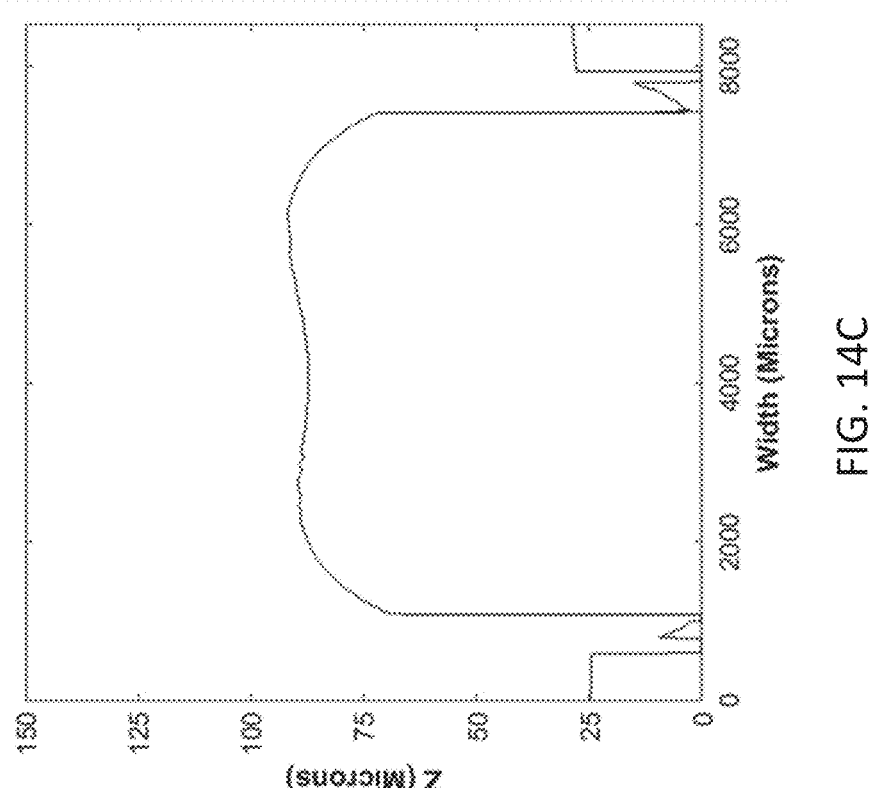
FIG. 14C is a graph representing the thickness of the (c) line in FIG. 14B.

SWLI was also used to determine whether cracking after 27 days of storage at 14.3±0.5% RH was occurring on the sample/coverslip or sample/air interface. FIG. 14 shows a comparison of a cracked samples SWLI map (FIG. 14A), non-interferometric image (FIG. 14B), and corresponding profiles (FIG. 14C and FIG. 14D). We see in the non-interferometric image that the cracks extend all the way across the sample; however, they do not show up on the height profile. This implies the cracks must be subsurface on the sample/coverslip interface. This is supported by the fact that we can see white light interference fringes in FIG. 23 (a) from the thin air gap that is forming from delamination. Delamination could potentially comprise sample integrity.

3.3.4 Raman Spectroscopy

Figure 15A:
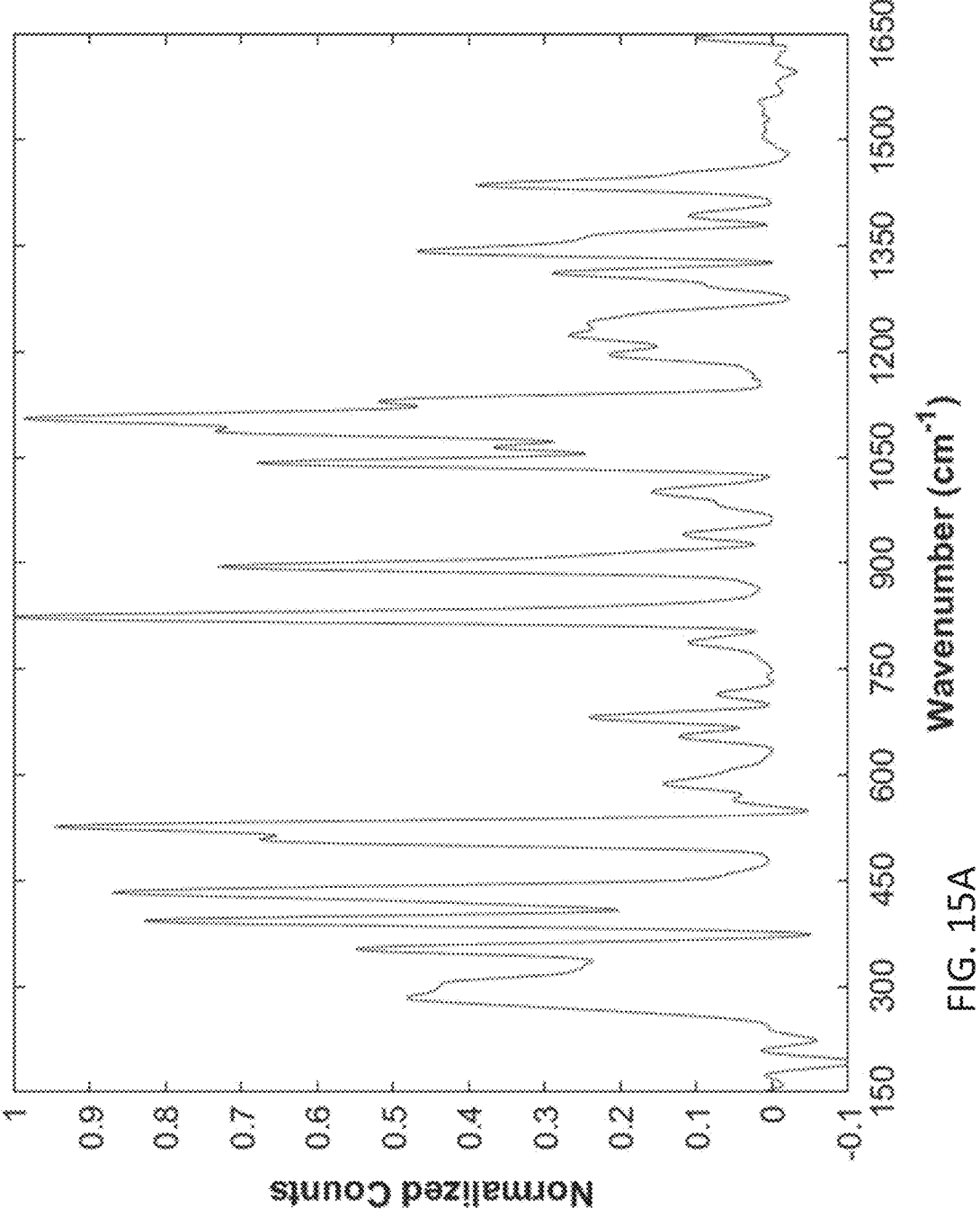
FIG. 15A is a graph of raman shift spectra of crystalline trehalose.
Figure 15B:
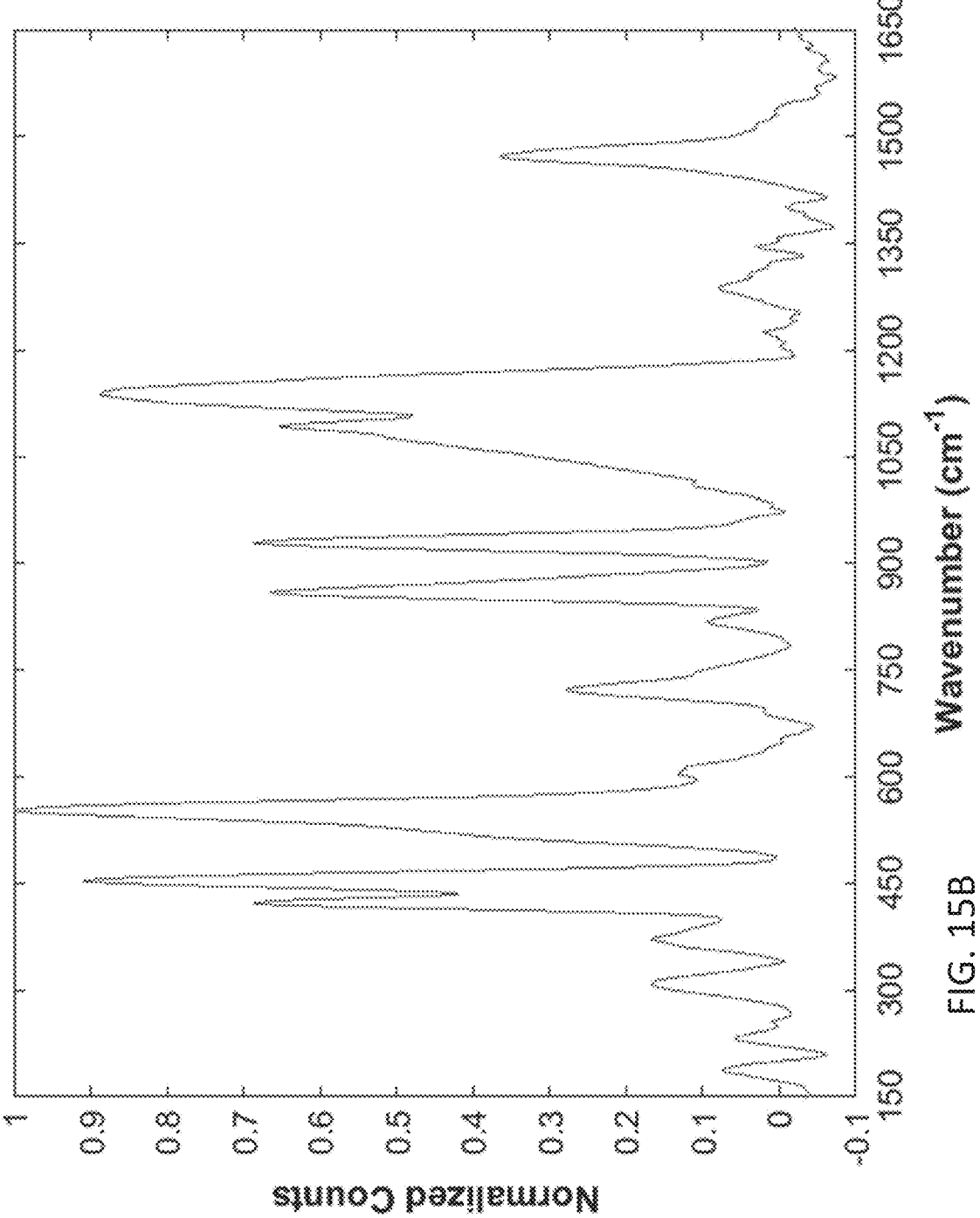
FIG. 15B is a graph of raman shift spectra of amorphous trehalose.
Figure 16A:
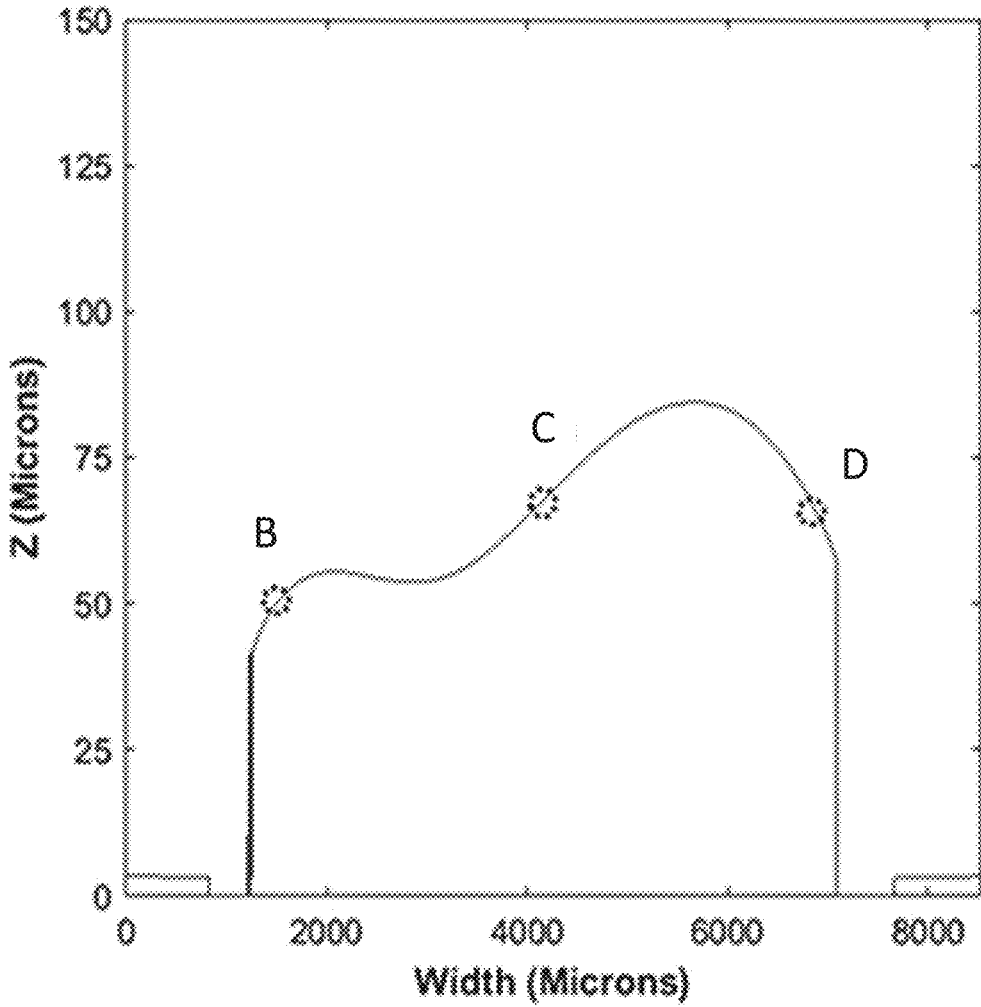
FIG. 16A is a graph representing an SWLI thickness profile of a LAD sample.
Figure 16B:
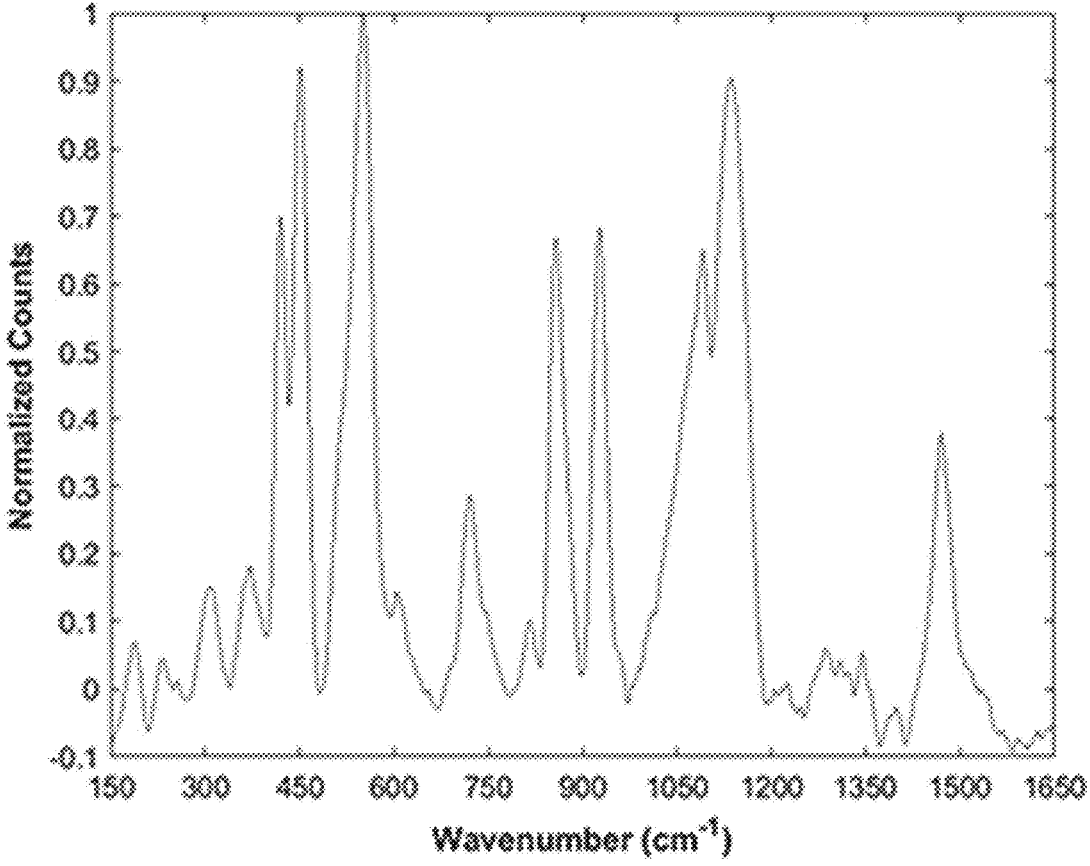
FIGS. 16B-16D are graphs of raman shift spectra at the three corresponding locations in FIG. 16A.
Figure 16C:
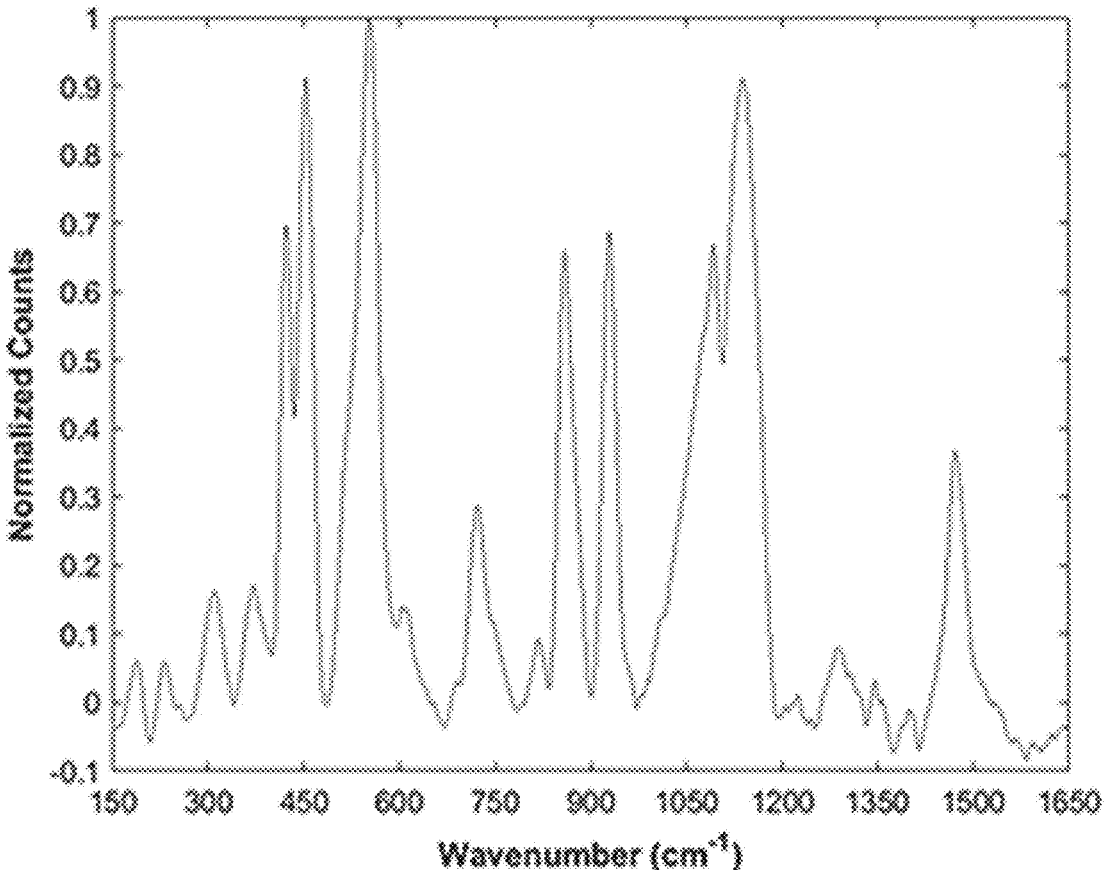
Figure 16D:
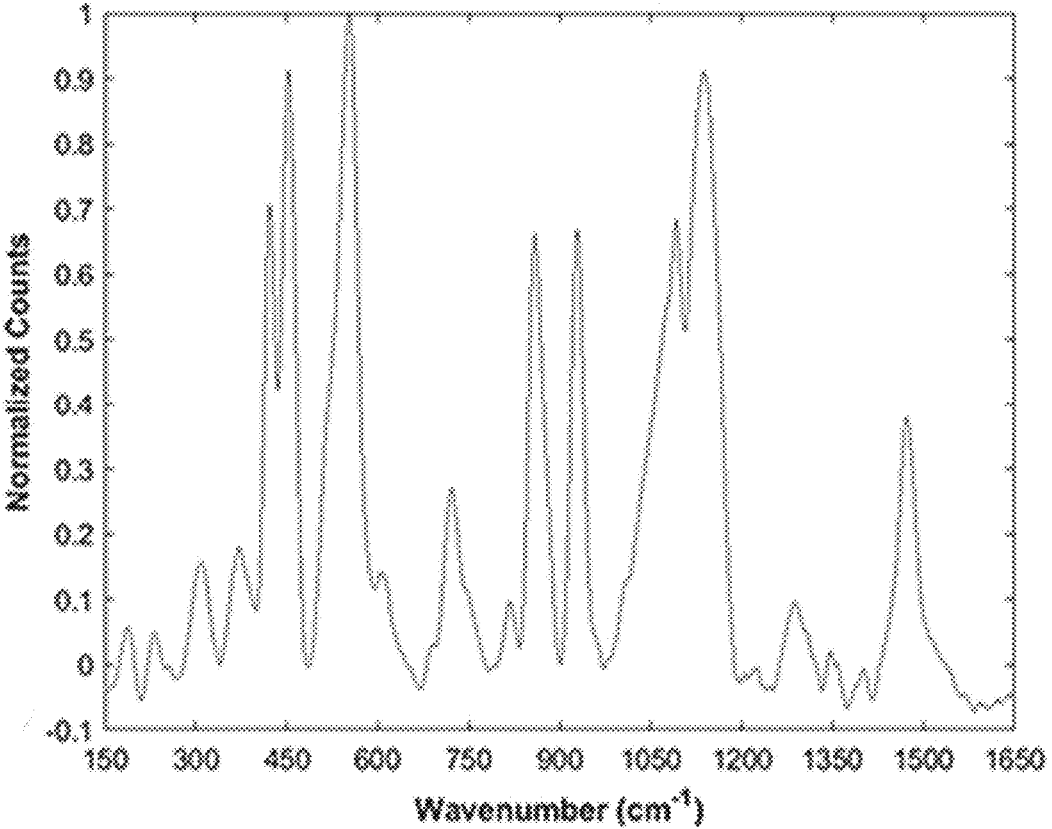

FIGS. 15A and 15B shows the difference in Raman spectra of crystalline trehalose and amorphous trehalose, respectively. Crystalline trehalose has very well defined, narrow bands while the amorphous bands are broadened. Because crystals possess long-range translational symmetry they have quantized lattice vibrations, and this limits the number of Raman active vibrational modes. The amorphous form does not have spatial order so vibrational modes are not limited by lattice vibrations. This means that all the vibrational modes are sampled resulting in band broadening.

Spectra were acquired at three transverse locations across a LAD sample to measure the relative distribution of trehalose across the sample. This was coupled with SWLI of the same sample to determine the relationship between thickness and trehalose distribution. FIG. 16 is a SWLI cross section of a sample (FIG. 16A) with the Raman spectra locations (FIG. 16B-16D) marked and the corresponding spectra at each location. First it is noted that the Raman spectrum for trehalose is present at each location indicating that the sugar is distributed across the sample. Comparing each sample set of spectra to the corresponding thickness measurement yielded no relationship. The trehalose at each location is in the amorphous state and not crystalline.

3.4 Discussion

PLI of LAD processed samples stored for an extended time at low RH shows promise for the long term stability of samples. Out of the three storage RH the lowest (14.3±0.5% RH) is the most logical option. Compared to the other two RH, crystallization for LAD processed samples was negligible. This reduces the risk of degradation during storage of proteins that are sensitive to the mechanical stresses of crystallization. However, initial crystallization of the sample during LAD processing indicates that the samples need to be dried faster to overcome crystallization during processing. Samples with very large initial crystal area have a higher likelihood of substantial crystal growth during storage. This will require a higher power LAD source or an alternate wavelength with a higher absorption coefficient in water. Both of these options would accelerate the drying time of LAD and potentially reduce initial crystallization that could act as a seed crystal during even longer storage times. These studies also revealed a phenomenon previously unaccounted for, desiccation cracking. Cracking during storage is unfavorable and could damage the embedded proteins and reduce storage life. Potential solutions include pushing the samples to an even drier state during LAD processing by changing the source, as mentioned previously, or lowering processing RH. Alternatively, one could raise the storage RH high enough to lower evaporation to prevent competition with the gel/substrate adhesion but keep it low enough to maintain an amorphous state.

SWLI showed that cracking was subsurface and accompanied by delamination of the sample. A potential solution for this could be a substrate change to something more flexible to contract and expand as the sample reaches very low EMC. Raman spectroscopy indicated that trehalose was in an amorphous form throughout LAD samples. While SWLI coupled with Raman spectroscopy did not yield a relationship between relative trehalose concentration and sample thickness, it did show that trehalose was distributed across the sample. The lack of correlation could mean that trehalose is evenly distributed across the sample regardless of thickness.

Example 4

Testing of Protein Functionality of Proteins Preserved with LAD

The present Example tests the application of LAD methods on an immobilized model protein, lysozyme, to determine protein functionality post processing and after short term storage.

The field of biologics has seen rapid growth in the past few decades because of an exponential increase in diagnostic and therapeutic target discoveries. Protein based biologics are used in therapeutics and diagnostics and have been developed to treat diseases ranging from arthritis and psoriasis to cancer. A challenge in the development of protein-based diagnostics and drugs is maintaining the protein in the folded state during processing and storage as the three-dimensional structure of the protein is often responsible for its functional activity. Long-shelf lives for proteins have been achieved by freeze drying, also known as lyophilization; however, the complexity, processing time, high cost and potential for instability during processing and storage are disadvantages of this technique. Even after lyophilization most proteins still have to be stored below 4° C. Recent research has demonstrated that anhydrous, or dry state, preservation in a trehalose amorphous (non-crystalline) solid matrix may be an alternative to freeze drying for the preservation of biological samples. Methods described herein, light assisted drying (LAD), create trehalose amorphous solids for the preservation of biologics. LAD uses illumination by near-infrared laser light to assist in the formation of trehalose amorphous solids. Static air-drying of sugar solutions is dominated by evaporative cooling which causes the drying rate to slow substantially and allows for crystallization of the sugars. LAD selectively heats water to overcome cooling due to evaporation and speeds dehydration of the samples. As water is removed from the sample, the remaining sugars and salts become concentrated, and, as long as the solutes do not crystallize, the viscosity increases with progressive water loss until an amorphous solid is achieved. Samples need to be stored below the glass transition temperature, $T_g$, of the trehalose matrix to prevent degradation. Previous examples demonstrated the effectiveness of LAD to reach end moisture contents (EMCs) low enough for storage at elevated temperatures in the glassy state and determined the optimal LAD processing parameters for achieving these EMCs. Previous examples also characterized sample morphology and distribution of the glass forming matrix, as well as, the subsequent storage conditions for optimal sample stability. This example addresses the functionality of proteins embedded in LAD processed samples. It also discusses the effect of protein concentration and size on EMC to determine whether LAD is universally applicable or would need to be optimized for each protein of interest. First, the EMC was measured at a specific LAD processing time of different protein concentrations and three different protein sizes. Then the functionality of a model protein, lysozyme, was tested immediately after LAD processing and after extended storage using a standard activity assay.

4.2 Methods

The LAD system with the 1064 nm laser and 1850 nm laser (as described in Example 1) was used for processing. Samples consisted of 40 μl droplets containing a model protein in a drying solution (DS). Proteins were mixed into the DS and the dry weight was adjusted using the protein concentration to include the mass of the protein.

For each test, a 40 µL droplet of the protein in DS was deposited onto an 18 mm diameter borosilicate glass coverslip (12-546, Fisherbrand) substrate and the initial mass was determined gravimetrically using a 0.01 mg readability balance (AS 82/220. R2, RADWAG). The sample was then moved into the humidity chamber for laser irradiation. The temperature of the sample was monitored during processing using the thermal camera. After irradiation, the sample was removed from the humidity chamber and immediately massed again to determine EMC.

4.2.1 Protein Concentration & Size

Samples (N=3 for each study) were LAD processed with the 1850 nm laser for 10 minutes at a power density of 4.04 W/cm2 corresponding to a maximum sample temperature of Tmax=72.9±2.0° C. For the protein size study, the present example uses egg white lysozyme (LS002933, Worthington Biochemical), ß-galactosidase (LS004090, Worthington Biochemical), and peroxidase (LS002559, Worthington Biochemical). Concentration of lysozyme, ß-galactosidase, and peroxidase was verified using the absorption of light at 280 nm, 275 nm, and 280 nm, respectively, with a microplate spectrophotometer (Bio-Tek Synergy HT). Size was defined as proteins hydrodynamic radius, the radius of an equivalent hard sphere diffusing at the same rate as the protein, (see Table 4) and each protein was used at a concentration of 0.5 mg/ml. The protein concentration study used lysozyme at 0.5, 10, and 25 mg/ml for testing. Sample EMC was determined immediately after processing.

TABLE 4

Proteins used in the protein size study and their corresponding hydrodynamic radii taken from various sources.

| Protein | Hydrodynamic Radius (nm) |
| --- | --- |
| Lysozyme | 1.9 |
| Peroxidase | 3.0 |
| β-galactosidase | 6.9 |

4.2.2 Lysozyme Functionality

All samples for the functionality studies consisted of 0.5 mg/ml lysozyme in DS. The functionality of lysozyme in each sample was measured using the assay described by Worthington Biochemical for the rate of lysis of Micrococcus lysodeikticus cells. The assay was altered to fit a 96-well format and measured the decrease in turbidity as a function of time at 450 nm, ∆A450/min, referred to as the response rate. We calculated the specific activity of each sample using the measured concentration and ∆A450/min.

The first functionality study used LAD with the 1064 nm laser at a maximum sample temperature, Tmax, of 43.0±1.8° C. All LAD—1064 nm processed samples (N=5) were heated with the 1064 nm laser for 60 minutes at a power density of 26.9 W/cm2. Air drying of samples (N=3) for 60 minutes at 11% RH was used as a comparison. Samples were assayed at three different times ts=0, 1, and 27 days after LAD processing/air drying. After LAD processing samples were stored individually in small volume containers above a saturated salt solution of lithium chloride (LiCl) (ChemCenter) at 14.3±0.5% RH. This was measured with an RH probe (HH314A, Omega). Storage times and the storage RH were based on the results from previous optical characterization work. The ts=0 days determined the functionality of embedded lysozyme immediately after LAD, ts=1 day allowed the samples to reach a lower EMC and lower their evaporation rate to a negligible value, and ts=27 days allowed subsurface cracking to occur in order to investigate its effects on embedded proteins. The three air dried samples were stored at a higher RH of 47.2±5.8% to promote crystallization of the sample and to assess the impact of crystallization on protein functionality.

A 0.5 ml aliquot of the stock solution was kept at ambient temperature for 27 days and also assayed for comparison. In addition, a 0.48 ml volume of the sample was also incubated in a water bath at ~45° C. for 60 minutes to compare the effect of heating without drying to LAD processed samples. Four 40 µl droplets were taken from this sample, diluted with deionized water to a concentration of 0.1 mg/ml of lysozyme for use in the functionality assay. It should be noted that the temperature of the LAD samples decreased during processing due to evaporative cooling, while the water bath samples were held at a near constant temperature.

The second functionality study used LAD with the 1850 nm laser at Tmax=87.0±2.3° C. One LAD—1850 nm sample was processed at 7.39 W/cm2 for 6 minutes and assayed immediately after. A 500 µL volume of the control solution was incubated in a water bath at ~90° C. for 4 minutes as a comparison. Before assaying, samples were re-hydrated and then diluted with deionized water to a concentration of 0.1 mg/ml of lysozyme to achieve a linear response rate for the assay. The concentration of lysozyme for each sample was verified by measuring the absorption at 280 nm.

4.3.1 Protein Concentration & Size

Figure 17:
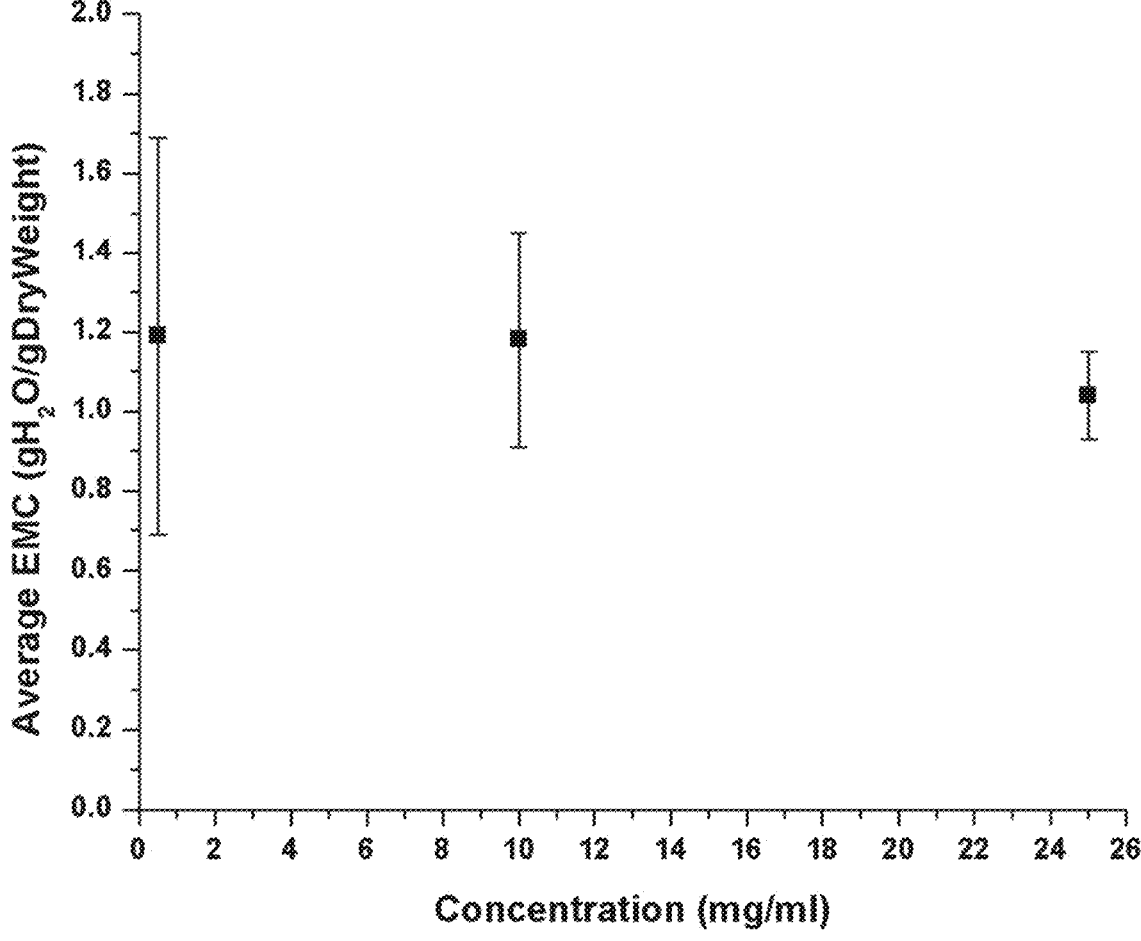
FIG. 17 is a graph of EMC for varying lysozyme protein concentration according to methods described herein.

FIG. 17 shows EMC as a function of protein concentration for lysozyme. Note that all concentrations were processed under the same conditions (LAD with 1850 nm at Tmax=72.9±2.0° C. for 10 minutes. There was no change in average EMC based on protein concentration and each one is within each other's standard deviation. However, there is a decrease in standard deviation with increasing protein concentration. This could be because an increase in protein concentration means lower initial moisture content leading to less variability at lower EMCs. This is supported by results from Example 2 were a decrease in EMC standard deviation at progressively lower EMC was observed.

Figure 18:
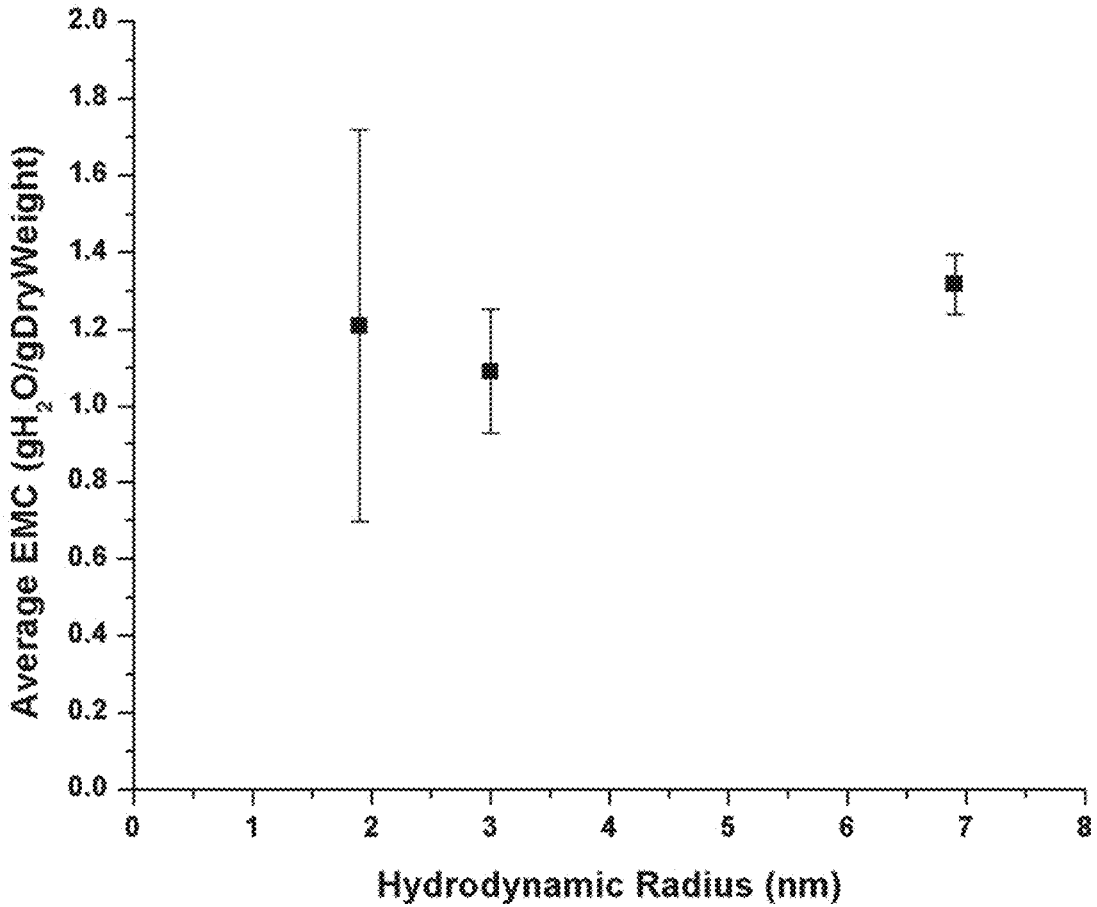
FIG. 18 is a graph of EMC for lysozyme (1.9 nm), peroxidase (3 nm), and ß-galactosidase (6.9 nm).

FIG. 18 shows EMC as a function of protein hydrodynamic radius in DS, LAD processed for 10 minutes with the 1850 nm laser at a $T_{max}$=72.9±2.0° C. Hydrodynamic radius is the apparent size of the solvated protein. Note that each protein is at the same concentration (0.5 mg/ml) and processed under the same conditions as listed for the protein concentration test. Lysozyme, peroxidase, and ß-galactosidase are 1.9, 3, and 6.9 nm respectively. There was no change in EMC with increasing hydrodynamic radius. However, the same decrease (as in FIG. 17) in standard deviation with increasing protein size was observed with increasing protein concentration. This could be attributed to the same lower initial moisture content theory as described previously.

The average EMC for each study indicate that protein concentration and size might not affect the EMC of LAD processed samples under the same processing parameters; however, the decrease in standard deviation with increasing protein concentration and protein size needs further investigation. The decrease could be caused by lower initial water content in which case LAD processing parameters might have to be adjusted on an individual protein-by-protein basis, or it could be an artifact of a low sample number and increasing N might show the same standard deviation regardless of protein concentration and size. This would imply that one set of processing parameters could be universally applied to most proteins. A larger sample size needs to be performed and a more exhaustive range of protein sizes and concentrations needs to be tested to determine the limits of this study.

4.3.2 Lysozyme Functionality

Figure 19:
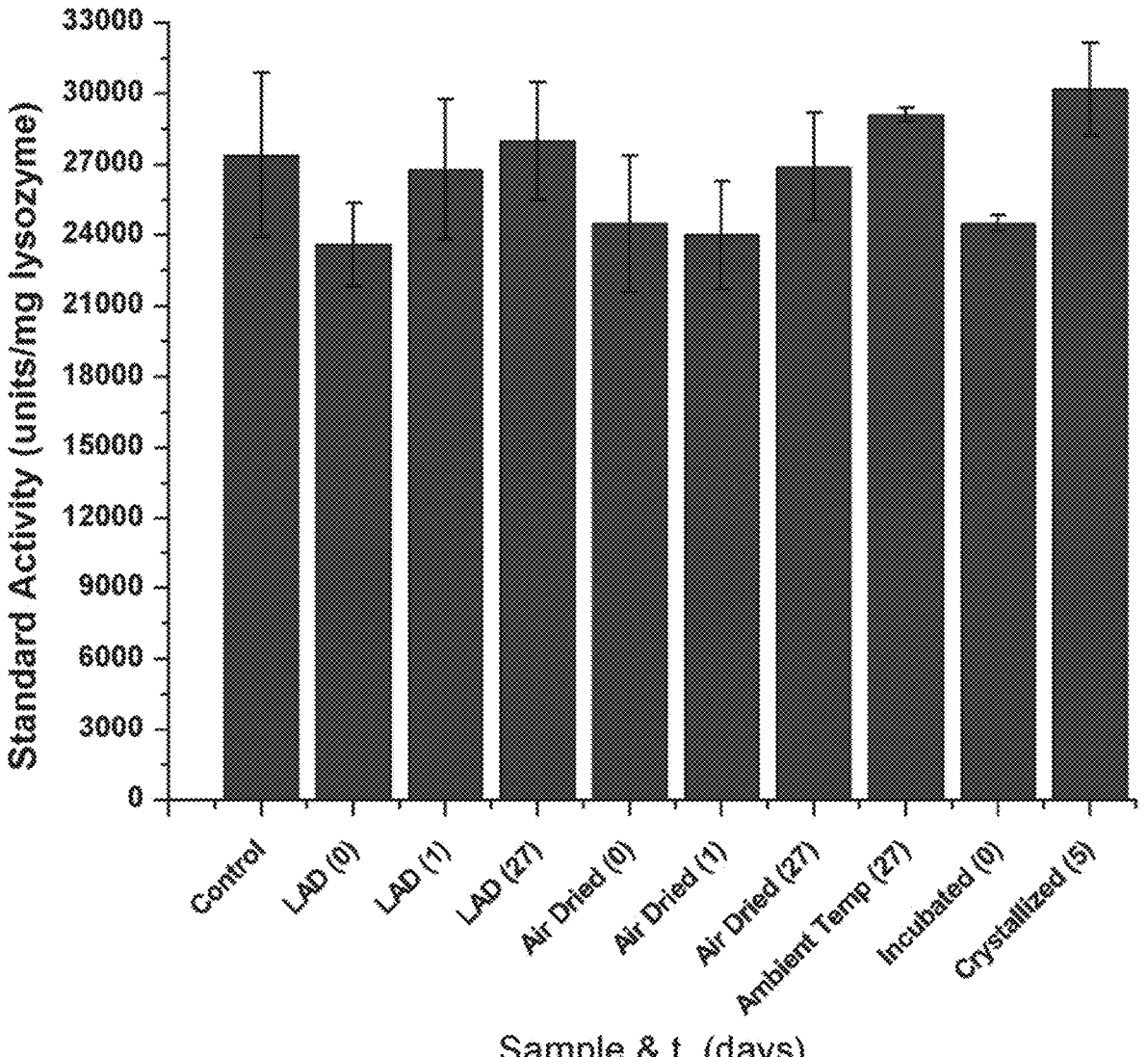
FIG. 19 is a comparative graph of standard activity for lysozyme.

This study addressed the functionality of proteins processed with LAD. FIG. 19 shows the standard activity for each set of samples assayed as described in the methods section. Specifically, standard activity of lysozyme for unprocessed refrigerated control solution, LAD processed, air dried, incubated in a sealed container (~45° C.), ambient temperature storage, and crystallized samples are presented. The numbers in parenthesis next to each sample label is the storage time in days before assaying. Standard activity for a lysozyme assay is a measure of how well lysozyme destroys micrococcus lysodeikticus cells; as functional lysozyme destroys cells the turbidity of the water decreases over time and the absorbance of 450 nm light decreases. Therefore, the rate at which absorbance at 450 nm changes over time depends on the functionality of lysozyme as well as the concentration. A higher percentage of denatured lysozyme will result in a lower rate of change of A450. Standard activity (SA) is measured as $$SA = \frac{\left(\frac{\Delta A_{450}}{min} * 1000\right)}{m_{lys}}$$

[Equation 6]

where $$\frac{\Delta A_{450}}{min}$$

is the rate of change of absorbance over time, 1000 is a conversion factor to units, and $m_{lys}$ is the mass of lysozyme in the reaction.

No significant change in functionality compared to the control solution for either LAD or air dried samples was observed. All variations in the average functionality of test samples fall within the standard deviation of the control. This implies that LAD does not have a negative effect on protein functionality during processing or subsequent initial storage. Because the incubated sample functionality was also unaffected it can be assumed that thermal denaturation did not occur. The average EMC of LAD samples at ts=0 days and ts=1 day was 0.12±0.02 and 0.06±0.01 gH₂O/ gDryWeight respectively. Extremely low EMC did not have an effect on protein functionality. Air drying, ambient temperature storage, and crystallization also did not show a loss in functionality. Lysozyme is a robust protein.

Figure 20:
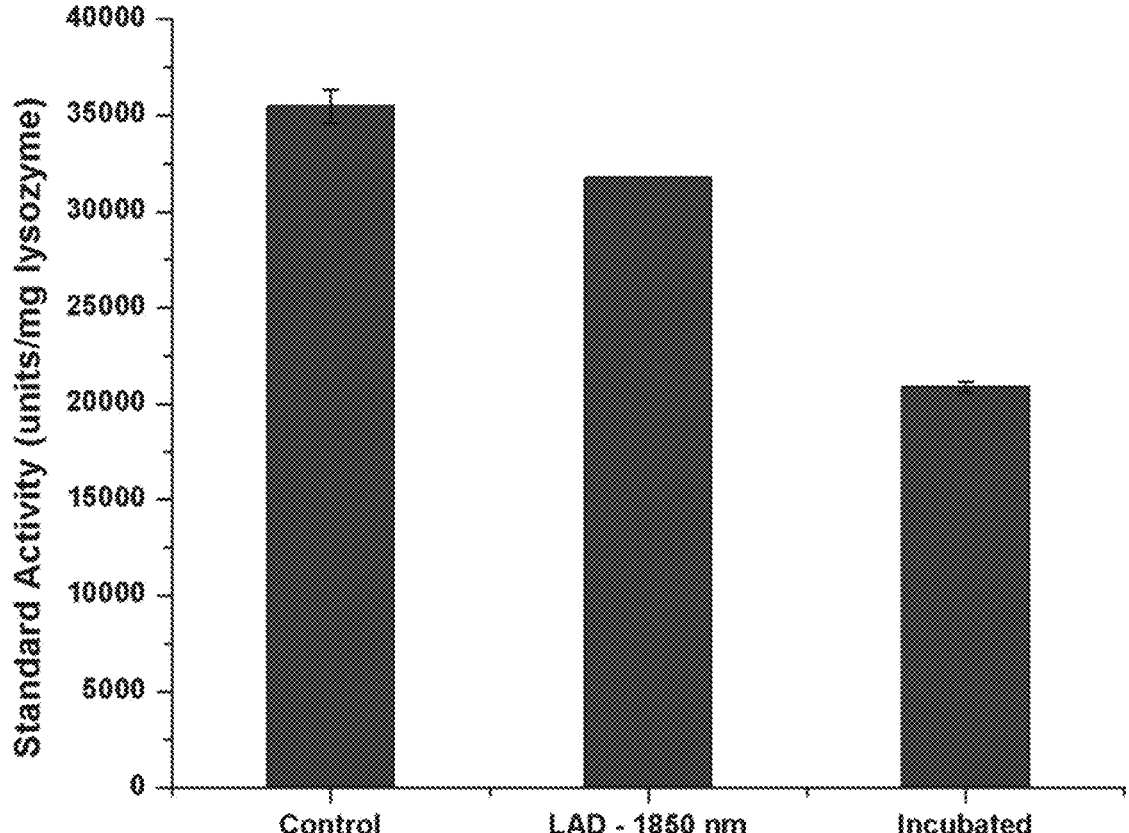
FIG. 20 is a comparative graph of standard activity for lysozyme.

FIG. 20 is standard activity of the preliminary functionality study of LAD at elevated temperatures utilizing the 1850 nm laser. Specifically, standard activity of lysozyme in DS samples for unprocessed refrigerated control solution, LAD processed with 1850 nm, and incubated at a comparable temperature (~90° C.). The LAD—1850 nm sample has no standard deviation, only one sample was processed and tested. The control solution that was kept at 8° C. has the highest SA. The LAD processed sample shows a small decrease in functionality compared to the control. The incubated sample has the lowest functionality, this is indication that the protein underwent thermal denaturation. Not only was the LAD sample processed for the same amount of time as the incubated sample at a comparable temperature (~90° C.) but it was also processed for 2 minutes longer at a slightly lower but still potentially damaging temperature (76.9±10° C.). This indicates that LAD processing has the potential to use elevated temperatures to speed up the drying process without damaging the embedded protein.

Figures 21A, 21B:
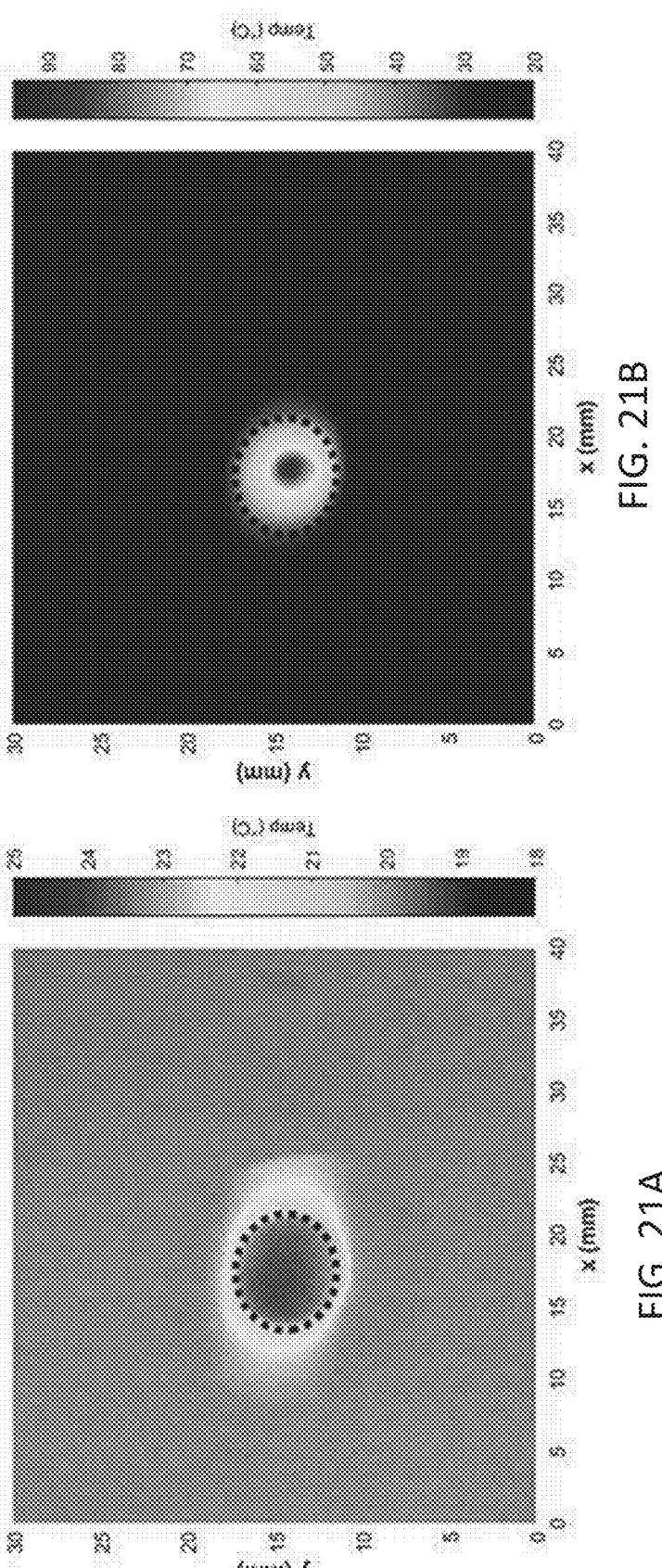
FIG. 21A is a thermal image of a sample prior to LAD processing according to methods described herein.
FIG. 21B is a thermal image of a sample after LAD processing according to methods described herein.
Figure 21C:
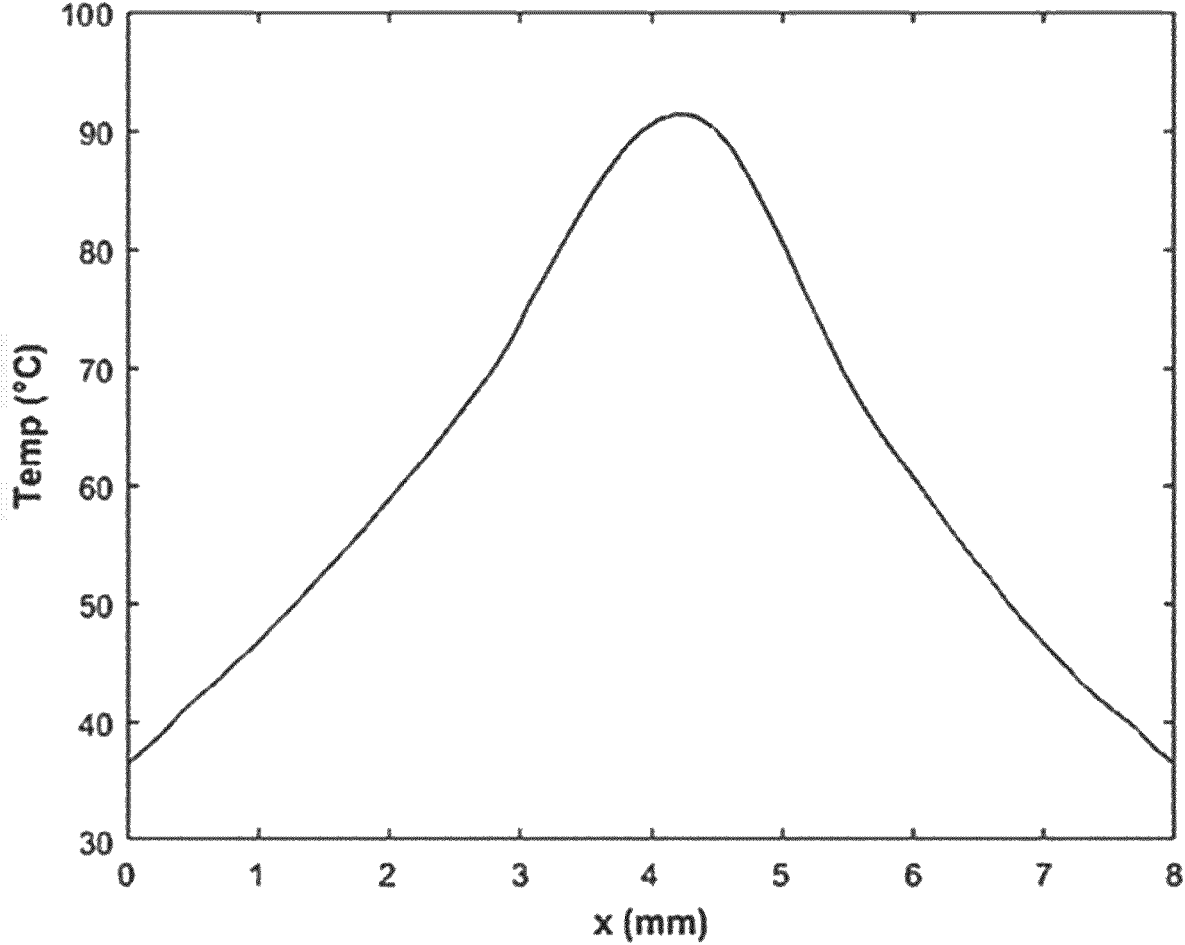
FIG. 21C is a graph illustrating the thermal profile across the sample in FIG. 21B.

Proteins processed via LAD at elevated temperatures do not appear to be thermally denatured as would be expected. This is most likely because of the thermal gradient across the sample. FIG. 21 shows a thermal image of sample before LAD processing (FIG. 21A) during LAD processing (1850 nm) at maximum temperature (FIG. 21B), and the corresponding thermal profile across the sample taken from (FIG. 21C). The dashed black circles in FIG. 21A and FIG. 21B indicate the location of the sample.

FIG. 21C shows the thermal profile across the droplet at the processing time corresponding to maximum sample temperature. The entire droplet is not at 90° C. The temperature profile is Gaussian and decreases down to <40° C. on the edges. Marangoni flows develop within sessile drying droplets because of the thermal gradient across them associated with evaporative cooling. LAD increases that thermal gradient and it can further increase the rate of recirculation within the droplet. This recirculation might mean that proteins are being pushed towards the edge of the droplet into cooler areas and then back along the surface towards the center where they are exposed to higher temperatures. This potential protein circulation across the drop would allow them to dry without experiencing constant elevated temperatures that would denature them.

4.4 Discussion

Varying protein size and concentration did not affect the average EMC of samples when processed with the same LAD parameters, but the standard deviation decreased with increasing concentration and size. Increasing the sample size (N) of this study will help determine if the standard deviation variability is truly related to concentration and size. The average EMC of all the samples indicates that LAD could potentially be applicable to a wide variety of proteins using one processing parameter set. This is beneficial for use on an industrial scale, many pharmaceutical companies produce products with a wide variety of proteins and having a universally applicable processing parameters means that LAD would not have to be optimized for individual proteins. However, this study will need to be expanded to test the limits of LAD in regards to a universal parameter set as there is likely a maximum concentration at which EMC will start to vary.

The lysozyme functionality study indicates that LAD processing with the 1064 nm laser at Tmax=43.0±1.8° C. does not affect the functionality of lysozyme. This data coupled with the water bath incubated samples implies that thermal denaturation is not occurring which makes sense because the processing temperature is well below the approximate unfolding temperature of lysozyme (~70-80° C. depending on solution).63 LAD and air samples reached EMCs that were below 0.1 gH2O/gDryWeight (corresponds to a storage temperature above room temperature) without denaturing. This means that very low EMC does not affect functionality. These results are promising for the ability of LAD to produce samples without denaturing the embedded protein. The preliminary LAD—1850 nm functionality study shows the ability of LAD to process proteins at temperatures larger than the unfolding temperature without a substantial loss of functionality. Because this study was limited in scope it will need to be expanded to definitively prove that LAD can not only process samples at elevated temperatures without thermal denaturation, but also show the effects of EMC on sample functionality.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A biological composition comprising:

a biological material contained in an amorphous solid matrix comprising a disaccharide component, wherein the biological composition has the identifying features resultant of a method comprising:

(a) providing a preservation composition comprising the biological material, the disaccharide component, a salt component, and water; and (b) exposing the preservation composition to an amount of electromagnetic radiation sufficient to form said amorphous solid matrix containing the biological material suitable for storage at ambient temperature, wherein the electromagnetic radiation is near infrared (NIR) laser light and/or radiation having a wavelength of 1-3 μm, and wherein the amorphous solid matrix has a glass transition temperature ($T_g$) greater than −30° C.

2. The biological composition of claim 1, wherein the amorphous solid matrix has $T_g$ greater than 0° C.

3. The biological composition of claim 1, wherein the amorphous solid matrix is free of crystals.

4. The biological composition of claim 1 having a water content less than 0.2 $gH_2O$/gdw of the biological composition.

5. The biological composition of claim 1 having a water content less than 0.1 $gH_2O$/gdw of the biological composition.

6. The biological composition of claim 1, wherein the biological material comprises biomolecules, viruses, bacteria, cells, engineered cells, tissues or microtissues.

7. The biological composition of claim 1, wherein the biological material maintains tertiary and/or quaternary biochemical structures in the amorphous solid matrix.

8. The biological composition of claim 1, wherein the biological material maintains at least 70% functionality.

9. The biological composition of claim 1, wherein the amorphous solid matrix containing the biological material is stored under an atmosphere having less than 50% relative humidity.

10. The biological composition of claim 1, wherein the amorphous solid matrix containing the biological material is stored under an atmosphere having less than 15% relative humidity.

11. A biological composition comprising:

a biological material contained in an amorphous solid matrix comprising a disaccharide component, wherein the biological composition has the identifying features resultant of a method comprising:

(a) providing a preservation composition comprising the biological material, the disaccharide component, a salt component, and water; and (b) exposing the preservation composition to an amount of electromagnetic radiation sufficient to form said amorphous solid matrix containing the biological material suitable for storage at ambient temperature, wherein the electromagnetic radiation is near infrared (NIR) laser light and/or radiation having a wavelength of 1-3 μm, and wherein the amorphous solid matrix has a water content less than 0.2 $gH_2O$/gdw of the biological composition.

12. The biological composition of claim 11, wherein the biological material maintains tertiary and/or quaternary biochemical structures in the amorphous solid matrix.

13. The biological composition of claim 11, wherein the biological material maintains at least 70% functionality.

14. The biological composition of claim 11, wherein the amorphous solid matrix comprises less than 5% crystallization.

15. The biological composition of claim 11, wherein the disaccharide component is trehalose or a trehalose derivative.

16. The biological composition of claim 11, further including a choline component, wherein the choline component is a choline halide, choline acetate, or choline phosphate.

17. The biological composition of claim 16, wherein a molar ratio of the disaccharide component to the choline component is 1:2 to 1:6.

18. The biological composition of claim 11, wherein the biological material comprises biomolecules, viruses, bacteria, cells, engineered cells, tissues or microtissues.

19. The biological composition of claim 11, wherein the amorphous solid matrix containing the biological material is stored under an atmosphere having less than 50% relative humidity.

20. The biological composition of claim 11, wherein the amorphous solid matrix containing the biological material is stored under an atmosphere having less than 15% relative humidity.

* * * * *